US009758573B2

(12) United States Patent
Vartanian et al.

(10) Patent No.: US 9,758,573 B2
(45) Date of Patent: Sep. 12, 2017

(54) METHODS TO PROTECT AGAINST AND TREAT MULTIPLE SCLEROSIS

(71) Applicants: Cornell University, Ithaca, NY (US); The Rockefeller University, New York, NY (US)

(72) Inventors: Timothy Vartanian, New York, NY (US); Kareem Rashid Rumah, New York, NY (US); Vincent A. Fischetti, Hempstead, NY (US)

(73) Assignees: Cornell University, Ithaca, NY (US); The Rockefeller University, New York, NY (US)

( * ) Notice: Subject to any disclaimer, the term of this patent is extended or adjusted under 35 U.S.C. 154(b) by 0 days.

(21) Appl. No.: 14/826,476

(22) Filed: Aug. 14, 2015

(65) Prior Publication Data

US 2016/0017022 A1    Jan. 21, 2016

Related U.S. Application Data

(63) Continuation of application No. PCT/US2014/016522, filed on Feb. 14, 2014.

(60) Provisional application No. 61/764,836, filed on Feb. 14, 2013, provisional application No. 61/805,788, filed on Mar. 27, 2013.

(51) Int. Cl.
*A61K 31/7048* (2006.01)
*A61K 38/47* (2006.01)
*A61K 39/00* (2006.01)
*C07K 16/12* (2006.01)
*A61K 35/741* (2015.01)
*A61K 35/742* (2015.01)
*C12Q 1/68* (2006.01)
*G01N 33/569* (2006.01)

(52) U.S. Cl.
CPC ...... *C07K 16/1282* (2013.01); *A61K 31/7048* (2013.01); *A61K 35/741* (2013.01); *A61K 35/742* (2013.01); *A61K 38/47* (2013.01); *A61K 39/00* (2013.01); *C12Q 1/689* (2013.01); *G01N 33/56911* (2013.01); *A61K 2039/505* (2013.01); *C07K 2317/76* (2013.01); *C12Q 2600/118* (2013.01); *C12Q 2600/142* (2013.01); *C12Y 302/01017* (2013.01); *G01N 2333/33* (2013.01); *G01N 2469/20* (2013.01); *G01N 2500/04* (2013.01); *G01N 2500/10* (2013.01); *G01N 2800/285* (2013.01)

(58) Field of Classification Search
CPC ............ A61K 39/00; A61K 2039/505; A61K 31/7048; A61K 35/741; A61K 35/742; A61K 38/47; A61K 31/724; A61K 39/08; A61K 2039/55566; A61K 31/00; A61K 31/09; A61K 31/409; C07K 16/1282
See application file for complete search history.

(56) References Cited

U.S. PATENT DOCUMENTS

| 6,287,563 B1 | 9/2001 | Williams et al. |
| 6,869,600 B1 | 3/2005 | Sadoul et al. |
| 7,740,861 B2 | 6/2010 | Ostroff |

OTHER PUBLICATIONS

Weindel et al. (2002, Biodrugs: 16(3):183-200 ).*
Ulzheimer et al. (2010, Biodrugs: 24(4):249-274 ).*
Hughes et al 2007 Journal of Bacteriology, 189, No. 21; 7531-7538.*
Knapp et al 2009, Biochimica et Biophysica Acta 1788 : 2584-2593).*
McClain et al 2007, Infection and Immunity, 75, No. 4, p. 1785-1793.*
European Supplementary Search Report for EP Application No. 14751390 dated Jun. 16, 2016 (6 pages).
Roarer et al., "The Production and Evaluation of Monoclonal Antibodies to Clostridium perfringens type D Epsilon Toxin," The International Association of Biological Standardization, 1988, 16:207-218.
Borrmann et al., "Development of a Cell Culture Assay for the Quantitative Determination of Vaccination-Induced Antibodies in Rabbit Sera Against Clostridium perfringens Epsilon Toxin and Clostridium novyi Alpha Toxin," Veterinary Microbiology, 2006, 114:41-50.
Szeto et al., "Minocycline Suppresses Activation of Nuclear Factor of Activated T Cells 1 (NFAT1) in Human CD4+ T Cells", Journal of Biological Chemistry, 2011, 286(13):11275-11282.
PCT International Search Report and Written Opinion for PCT Application No. PCT/US2014/016522 dated Aug. 27, 2014 (13 pages).
Enzinger et al., "Accelerated Evolution of Brain Atrophy and 'Black Holes' in MS Patients with APOE-•4," Annals of Neurology, 2004, 55(4):563-569.
Rumah et al., "Isolation of Clostridium perfringens Type B in an Individual at First Clinical Presentation of Multiple Sclerosis Provides Clues for Environmental Triggers of the Disease," Plos One, 2013, 8(10):1-9.

(Continued)

*Primary Examiner* — Padma V Baskar
(74) *Attorney, Agent, or Firm* — Eversheds Sutherland (US) LLP

(57) ABSTRACT

The invention provides epsilon toxin (ETX) produced by *Clostridium perfringens* type B or type D as a causative toxin for human multiple sclerosis (MS). The invention further identifies ETX binding receptor MAL for ETX mediated cell death and other toxin-logical activities in MS. Methods and compositions to prevent humans from multiple sclerosis (MS) and/or treating MS by directly or indirectly interfering with epsilon toxin (ETX), its binding receptor (e.g., MAL), or ETX-receptor interactions so as to inhibit or suppress downstream ETX mediated receptor signaling activities are provided. Also provided are various methods to detect, diagnose, monitor, assess multiple sclerosis (MS) by determining an expression level of ETX gene or its encoding protein in human patient suspected for and/or at risk for multiple sclerosis (MS).

5 Claims, 20 Drawing Sheets

(56) References Cited

OTHER PUBLICATIONS

European Office Action for EP Application No. 14751390 dated Mar. 9, 2017 (5 pages).
Nikodemova et al., "Minoclycline Down-Regulates MHC II Expression in Microglia and Macrophages Through Inhibition of IRF-1 and Protein Kinase C (PKC) alpha/beta11," The Journal of Biological Chemistry, 2007, 282 (20):15208-15216.

\* cited by examiner

FIGURE 19

METHODS TO PROTECT AGAINST AND TREAT MULTIPLE SCLEROSIS

CROSS REFERENCES TO RELATED APPLICATIONS

This application is a continuation of PCT Application No. PCT/US2014/016522 filed Feb. 14, 2014 which claims priority to U.S. Provisional Application No. 61/764,836, filed Feb. 14, 2013, and U.S. Provisional Application No. 61/805,788, filed Mar. 27, 2013, the entire contents of which are incorporated by reference herewith.

SEQUENCE LISTING

The instant application contains a Sequence Listing which has been submitted electronically in ASCII format and is hereby incorporated by reference in its entirety. Said ASCII copy, created on Aug. 10, 2015, is named 31305-0038_SL.txt and is 14,944 bytes in size.

FIELD OF THE INVENTION

The invention relates to a method of detecting, diagnosing, monitoring, assessing, protecting against, and treating multiple sclerosis.

BACKGROUND OF THE INVENTION

How multiple sclerosis (MS) begins remains unknown. The earliest lesions studied, fixed hours after onset of symptoms, exhibit oligodendrocyte apoptosis, blood-brain barrier (BBB) permeability, and early microglial activation.[1-6] In these nascent lesions, demyelination is not yet apparent, there are no lipid-laden macrophages and there is the conspicuous absence of infiltrating lymphocytes.[1-8] The absence of an inflammatory infiltrate in nascent lesions argues against MS beginning as an autoimmune phenomenon and instead favors a toxin or viral etiology. Hence it seems reasonable that the environmental trigger for initial lesion formation in MS might be a soluble toxin based on the histopathologic features of the nascent lesion.

*Clostridium perfringens* is a gram positive, spore forming anaerobe that is sub-categorized into five toxinotypes based on combinatorial carriage of α, β, ε and ι toxins[9-11] (Table 1).

TABLE 1

*Clostridium perfringens* toxinotypes and known associated human diseases.

| Toxinotype | Toxin Carriage | Human Diseases |
|---|---|---|
| A | α | Food-born illness, diarrhea, toxic enteritis, gangrene |
| B | α, β, ε | None known |
| C | α, β | Necrotic enteritis (Pig-bel. Darmbrand) |
| D | α, ε | Rare toxic enteritis |
| E | α, ι | None known |

*C. perfringens* types B and D carry the epsilon toxin (ETX) gene, which encodes a 33 kD protoxin of the epsilson toxin. With log phase growth, protoxin is secreted and cleaved by trypsin and chymotrypsin in the gastrointestinal (GI) tract or by the *C. perfringens* encoded λ-protease, yielding an active epsilon toxin (ETX) which is ~1,000× more potent than the protoxin.[11]

The natural hosts for *C. perfringens* toxinotypes B and D are ruminant animals in whom ETX-mediated neurologic symptoms occur when carbohydrate rich feed or over grazing favors exponential growth of the bacilli.[11] ETX is absorbed via the intestine, enters the blood stream and permeabilizes the BBB, resulting in MS like symptoms (e.g. visual dysfunction, incoordination and spastic paralysis). Murrell and colleagues, because of these effects on the CNS,[12,13] first suggested ETX as a potential MS trigger in animals, such as sheep, although humans are not natural hosts for types B or D.[11,14]

ETX binds to a previously unknown receptor present both in the brain vasculature and myelinated brain regions, e.g., corpus callosum.[15-17] Once bound to its receptor, ETX integrates into the plasma membrane as a heptameric pore, leading to osmolysis.[11,14] When ETX is administered to rodents, BBB disruption occurs and white matter vasculature is especially vulnerable.[16,17] Interestingly, intraperitoneal administration of protoxin in rats results in the formation of focal ovoid lesions within the corpus callosum, in which the long axis of the ovoid is oriented perpendicular to the surface of the lateral ventricle.[18] Dawson first described this specific lesion morphology and the radiographic equivalent of demyelination surrounding a central vennule is pathognomonic for clinically definite multiple sclerosis.[19]

SUMMARY OF THE INVENTION

The invention provides that epsilon toxin (ETX) produced by *Clostridium perfringens* types B or type D, or ETX produced by other bacteria that have acquired it through mechanisms of horizontal plasmid transfer, is a causative toxin for nascent lesion formation in multiple sclerosis (MS) and required for the initiation of MS. The invention further provides that ETX interacts with the tetraspan integral membrane protein MAL (Myelin and Lymphocyte Protein) as its cognate receptor and that MAL is both necessary and sufficient for the actions of ETX. In view of these discoveries, the invention provides various methods to detect, diagnose, monitor, and assess multiple sclerosis (MS) by determining an expression level of ETX gene or its encoding protein in a subject suspected for and/or at risk for multiple sclerosis (MS). The invention further provides various methods to protect a person from having multiple sclerosis (MS) or to treat a person with MS by a) directly or indirectly interfering with epsilon toxin (ETX) of *Clostridium perfringens* type B or type D; b) directly or indirectly interfering with ETX interacting receptor, such as MAL and/or a virus cellular receptor-1 (HAVcR-1); c) directly and/or indirectly interfering with the interaction of ETX with its linking receptor, as well as downstream signaling activities; and d) directly or indirectly interfering, inhibiting or killing *Clostridium perfringens*.

In certain embodiments, the invention provides a method to protect a person from developing multiple sclerosis (MS) or to treat a person for MS by administering to the person in need thereof a composition comprising an effective amount of an inhibitor of epsilon toxin. One such inhibitors are antibodies against epsilon toxin (ETX), either monoclonal or polyclonal antibodies. Monoclonal antibodies to this toxin have been reported[33-35] and shown to neutralize the in vivo effect of this toxin in animal models.[35]

In other embodiments, the invention provides a method to protect a human subject from suffering multiple sclerosis (MS) or to treat a person for MS by administering to the subject in need thereof a composition comprising an effective amount of an inhibitor of a receptor to which epsilon toxin (ETX) binds. In certain embodiments, the invention discovers MAL receptor as the ETX linking receptor, and inhibitors/antagonists of this receptor are therapeutic candidates for protecting and/or treating MS. In other embodiments, the invention provides that inhibitors of the receptor on the blood brain barrier (BBB), such as MAL or the Hepatitis A virus cellular receptor-1 (HAVcR-1), which has been reported to be involved in the control of tight junctions of endothelial cells,[36-37] can also be therapeutic candidates for protecting and/or treating MS. Compounds that have been found to potentially inhibit ETX binding to MAL or HAVcR-1 include, but are not limited to, the mutant epsilon toxins (ETX-Y29E, ETX-Y30E, ETX-Y36E and ETX-Y196E).[37] In certain embodiments, the ETX-H106P mutant[41] is another candidate for an ETX receptor antagonist.

Furthermore, the invention provides a method to protect a subject from developing multiple sclerosis (MS) or to treat a subject for MS by administering to the subject in need thereof a composition comprising an effective amount of vaccine against *Clostridium perfringens* type B or D, or the epsilson toxin produced therefrom. Several such vaccines have been developed and employed to protect animals from *Clostridium perfringens* infections, and recombinant forms are in development.[38-39]

The invention further provides a method to protect a subject from developing multiple sclerosis (MS) or to treat a subject for MS by administering to the subject in need thereof an effective amount of probiotic supplement which contains a bacterial strain that outcompetes *C. perfringens* type B. In certain embodiments, the probiotic supplement contains *C. perfringens* type A bacterial strain since its toxinotype has been shown to outcompete *C. perfringens* type B. Typical bacteria strains included in probiotic supplement preparations include, but are not limited to, *Lactobacillus acidophilus, L. bulgaricus, L. casie, L. fermentum, L. Plantarum, Rhodoseudomonas palustris, Saccharomyces cerevisiae*, and *Steptococcus thermophiles*. These strains are common in various human foods and are ubiquitously used in manufacturing of probiotic dietary supplement products for human, animal and aquaculture health.

The invention also provides a method to treat a subject for MS by administering to the subject in need thereof a composition comprising an effective amount of a course of antibiotics, sufficient to kill off *C. perfringens* type B and/or D bacterial strains. Antibiotics found to be effective against *C. perfringens* include, but are not limited to, penicillin, ampicillin, amoxicillin, metronidazole, erythromycin, and tylosin.

The invention also provides a method to prevent MS or treat a subject for MS through bacteriophage therapy. *C. perfringens* specific bacteriophages eliminate *C. perfringens* in the host with little or no consequence on the healthy microbiota. *C. perfringens* specific bacteriophages include, but are not limited to, Siphoviridae, and with short noncontractile tails, members of the family Podoviridae. Several bacteriophage genes were identified that encoded N-acetylmuramoyl-1-alanine amidases, lysozyme-endopeptidases, and a zinc carboxypeptidase domain that has not been previously reported in viral genomes. Putative phage lysin genes (ply) were cloned and expressed in *Escherichia coli*. The recombinant lysins were amidases capable of lysing both parental phage host strains of *C. perfringens*, as well as other strains of the bacterium in spot and turbidity reduction assays, but did not lyse any clostridia beyond the species. Consequently, bacteriophage gene products can eventually be used to target bacterial pathogens, such as *C. perfringens* via a species-specific strategy, to control animal and human diseases without having deleterious effects on beneficial probiotic bacteria.

In certain embodiments, the bacteriophage is bacteriophage ΦCPV1 and multivalent bacteriophage cocktail designated. In other embodiments, the bacteriophage comprises a phage lytic enzyme, e.g., a lysin, that is specific for *C. perfringens* types B and/or D. One such lysin, a muramidase from strain ATCC 13124 (termed PlyCM) has been identified.[32] Lysins specific for *Clostridium perfringens* can also be delivered to subjects through genetically engineered probiotics. Probiotic strains expressing lysin genes that specifically hydrolyze the peptidoglycan or other components of the *Clostridium perfringens* cell wall can be utilized to kill *Clostridium perfringens*.

In certain embodiments, one or more agents used in the above-discussed methods for protecting and/or treating MS can be administered separatedly in a separately formulated composition each comprising a pharmaceutically suitable and acceptable carrier or adjuvant mixed with the agents. In other embodiments, one or more such agents can be combined and/or formulated together in a composition further comprising a pharmaceutically suitable and acceptable carrier or adjuvant mixed with these agents. The composition of the invention can be formulated in any pharmaceutically suitable and/or acceptable formulations for any suitable and/or acceptable administration routes, including, but not limited to, oral tablet or capsule, parental injectable solution or suspension, or subcutaneous patches. The composition of the invention can be administered alone, or in combination with any suitable agent or compound to enhance the effect for prevention and treatment of MS, and/or reduce any syndroms directed or indirected associated with MS disease and/or side effects resulted from the treatment.

The invention also provides a method for diagnosing and/or prognosing the course and risk of a patient with MS by determining levels or activity of epsilon toxin (ETX) gene, and/or its encoding protein in a biological sample of a patient at risk, wherein an elevated level and/or activity of ETX gene or protein suggests the patient is at risk of MS. A kit, a device, and/or a research tool used for the diagnosis and/or prognosis of MS in a tissue of a patient, comprising at least one or more reagents for determining levels or activity of ETX gene, and/or its encoding protein in a patient sample, and an instruction on how to conduct the diagnosis and/or prognosis method is also provided in the invention.

The invention further provides a method to screen for an agent, a compound (peptides or small molecules), or a drug that targets ETX gene or its encoding protein itself, ETX binding receptor, such as MAL and HAVcR-1, or interaction between ETX and its binding receptor, and useful therapeutics for predicting, preventing, ameliorating, and/or treating MS. Such screening method comprises the steps of exposing a candidate agent with ETX or its binding receptor MAL, determining an binding affinity of the candidate agent to ETX or its binding receptor MAL, and identifying the candidate agent as a ETX or MAL modulator when the candidate agent binds to ETX or MAL gene or protein or modulates its activity in the downstream signaling pathways or resulting in evidence of ETX mediated cell death. As used herein, the term "modulating" or "modulator" means "inhibiting" or "inhibitor," "antagonizing" or "antagonist" wherein after exposing the candidate agent to ETX or MAL, the level and activity of ETX or MAL is reduced or decreased. In certain embodiments, the candidate agent is a ETX or MAL inhibitor, antagonist, antisense, or antibody.

BRIEF DESCRIPTION OF THE DRAWINGS

The invention may be more readily understood with reference to the figures which are briefly described below. References to colors shown in the figures correspond to grey scales shown in the attached drawings.

FIG. 13A provides representative images (top rows) and quantitation (bottom panel) of MBP-immunostaining (green) with slices exposed to PBS (vehicle control, first column) or 5 nM ETX (columns 2-4) for 20 hours. ETX-neutralizing monoclonal antibody 4D7 was omitted (column 1 and 2) or added in slice culture at two different time points: 2 hours prior to (column 3) and concurrent with (column 4) ETX treatment. DAPI (blue) is counterstained to identify cell nuclei. n=5-6 slices for each condition, normalized to respective controls (100%); * p<0.001, two-tailed t-test. Similar results were obtained in three independent experiments. Scale bar represents 500 µm. FIG. 13B provides representative images (top rows) and quantitation (bottom panels) of MBP (row 1 and 2, bottom left panel, green)- and CNPase (row 3 and 4, bottom right panel, green)-immunostaining with slices exposed to PBS (vehicle control, first column) or 5 nM ETX (columns 2-4) for 20 hours. ETX-neutralizing monoclonal antibody 5B7 was omitted (column 1 and 2) or added in slice culture at two different time points: 2 hours prior to (column 3) and concurrent with (column 4) ETX treatment. DAPI (blue) is counterstained to identify cell nuclei. n=5-6 slices for each condition, normalized to respective controls (100%); * p<0.001, two-tailed t-test. Similar results were obtained in two independent experiments. Scale bar represents 500 µm.

FIG. 19. ε-toxin kills oligodendrocytes. 19A. Mixed primary glia culture grown in media to promote oligodendrocyte maturation were identified by live O1 staining. Cultures were treated with the indicated ε-toxin doses for 1 and 4 hours. Cell viability was evaluated by PI inclusion. % dead cells was calculating by dividing the number of PI positive O1+ cells by the total number of O1+ cells. Results are mean±STEDV. 19B. Typical micrographs of live mixed primary glia culture stained with A2B5 and O1 antibodies on left side. Cultures were treated with 100 nM of ε-toxin for 4 hours and cell viability was evaluated by PI inclusion. Arrows point to PI positive O1+ cells. Quantification of the percentage of dead A2B5+ cells and O1+ cells after 1 hour of ε-toxin 100 nM treatment on right side.

DETAILED DESCRIPTION OF THE INVENTION

Figure 1:
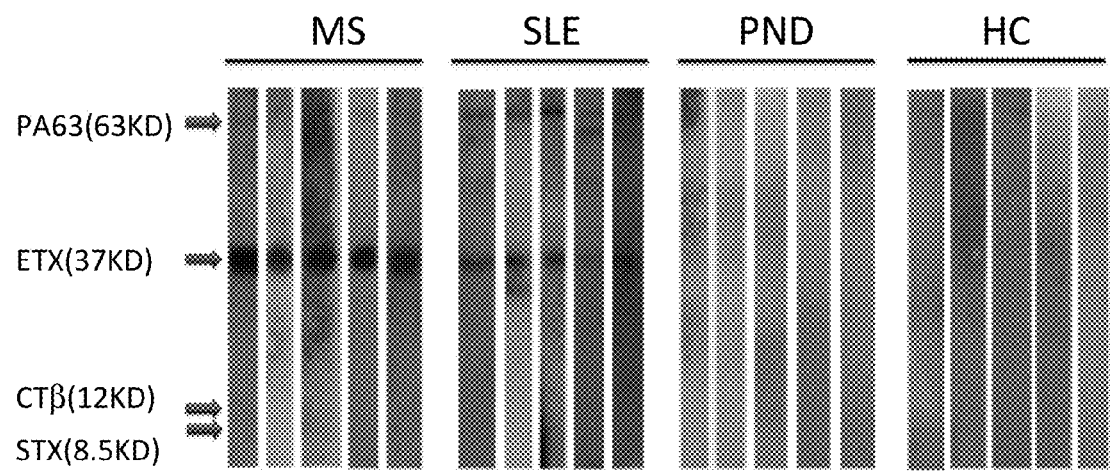
FIG. 1. Immunoreactivity to ETX in people with MS, SLE, paraneoplastic disease (PND) and healthy controls (HC). Upper panel shows Western blots. The two MS blots shown are characteristic for true positives: immunoreactivity to the *C. perfringens* proETX protein at 37 kD but not to the other toxins present on the blot including PA63 at 63 kD. The two blots probed with SLE sera are characteristic of false positives in that immunoreactivity is also present for PA63. Paraneoplastic disease (PND) and healthy controls (HC) shown are true negatives with no immunoreactivity to any of proteins present on the blot. Note that the proETX gene encodes a protein with a predicted MW of 33 kD, which runs on SDS-PAGE with an apparent MW of 37 kD. The lower panel shows prevalence of immunoreactivity to ETX in serum and/or CSF of people with MS (N=118) and healthy controls (N=100).
Figure 1:
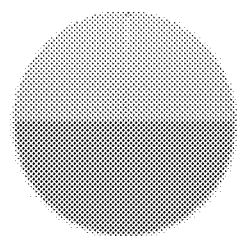
Figure 1:
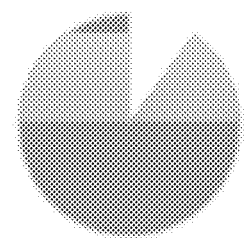

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention for the first time identifies epsilon toxin (ETX) produced by *Clostridium perfringens* type B or type D bacterial strain as a causative toxin for nascent lesion formation in multiple sclerosis (MS) in human. The invention further provides that ETX binds to the tetraspan integral membrane MAL receptor expressed in myelin and lymphocytes for ETX mediated cell death and other toxlogical activities in human MS.

In view of these discoveries, the invention provides various methods to detect, diagnose, monitor, assess multiple sclerosis (MS) by determining an expression level of ETX gene or its encoding protein in a human subject suspected for and/or at risk for multiple sclerosis (MS). The invention further provides various methods to protect a person from having multiple sclerosis (MS) or to treat a person with MS by a) directly or indirectly interfering with epsilon toxin (ETX) of *Clostridium perfringens* type B or type D; b) directly or indirectly interfering with ETX interacting receptor, such as MAL and/or a hepatitis A virus cellular receptor-1 (HAVcR-1); and c) directly and/or indirectly interfering with the interaction of ETX with its linking receptor, as well as downstream signaling activities.

In certain embodiments, the invention provides a method for preventing or treating multiple sclerosis (MS) in a human subject in need comprising: administering to said human subject a composition comprising an effective amount of an agent that directly or indirectly interferes with epsilon toxin (ETX) produced by *Clostridium perfringens* type B or type D bacterial strain, an ETX-binding receptor, or an interaction of ETX with its binding receptor so as to inhibit or suppress ETX modulated receptor signaling pathway. In certain embodiments, said agent is an inhibitor of ETX or its binding receptor expressed on endothelial cells of blood brain barrier (BBB), blood retinal barrier (BRB), oligodendrocytes, or myelin for which ETX is a ligand. In certain embodiments, the ETX-binding receptor is a tetraspan integral membrane receptor MAL, which is expressed in myelin, and by CNS endothelial cells, oligodendrocytes, intestinal epithelium lymphocytes. In other embodiments, the ETX-binding receptor is HAVcR-1 receptor.

In certain embodiments, the inhibitor is an antibody against ETX, or its binding receptor, such as MAL and/or HAVcR-1, or a functional fragment thereof, e.g., antigen binding fragment or antigen-binding portion. Methods of generating antibodies against ε-toxin of *C. perfringens* are well known in the art and are contemplated in the scope of this invention. Examples of antibodies and antibody responses against ε-toxin of *C. perfringens* are described, for instance, by Bentancor et al. (J Infect Dev Ctries 2009, 3(8):624-627); Laine et al. (Veterinary Immunology and Immunopathology 125, 2008, 198-202); Uzal et al. (Veterinary Research Communications, 23, 1999, 143-150); Percival et al. (Infection and Immunity, 1990, 2487-2492), the entire contents of each of which are incorporated by reference herewith.

As used herein, the term "antibody" includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. "Inactivating antibodies" refers to antibodies that do not induce the complement system.

The term "hypervariable region," "HVR," or "HV," when used herein refers to the regions of an antibody-variable domain that are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. See, e.g., Xu et al. Immunity 13:37-45 (2000); Johnson and Wu in Methods in Molecular Biology 248:1-25 (Lo, ed., Human Press, Totowa, N. J., 2003). Indeed, naturally occurring camelid antibodies consisting of a heavy chain only are functional and stable in the absence of light chain. See, e.g., Hamers-Casterman et al., Nature 363:446-448 (1993) and Sheriff et al., Nature Struct. Biol. 3:733-736 (1996).

"Framework" or "FR" residues are those variable-domain residues other than the HVR residues as herein defined. The term "Fc region" is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daeron, Annu. Rev. Immunol. 15:203-234 (1997). FcRs are reviewed in Ravetch and Kinet, Annu. Rev. Immunol. 9: 457-92 (1991); Capel et al., Immunomethods 4: 25-34 (1994); and de Haas et al., J. Lab. Clin. Med. 126: 330-41 (1995). Other FcRs, including those to be identified in the future, are encompassed by the term "FcR" herein.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," 5.sup.th Edition, U.S. Department of Health and Human Services, 1992; Chothia et al., J. Mol. Biol., 1987, 196: 901; and MacCallum et al., J. Mol. Biol., 1996, 262: 732, each of which is incorporated by reference in its entirety).

As used herein, the term "antigen-binding portion" of an antibody (or simply "antibody portion"), refers to one or more fragments of an antibody that retain the ability to specifically bind to an antigen (e.g., ETX, or its binding receptor, such as MAL). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_H$, $V_L$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_H$ and $V_L$ domains of a single arm of an antibody, (v) a dAb fragment (Ward et al., (1989) Nature 341:544 546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423 426; and Huston et al. (1988) Proc. Natl. Acad. Sci. USA 85:5879 5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

In certain embodiments, antibodies are isolated antibodies selected from polyclonal or monoclonal; xenogeneic, allogeneic, or syngeneic; or modified forms thereof (e.g., humanized, chimeric, recombinant etc.). Antibodies may also be fully human. Preferably, antibodies of the invention bind specifically or substantially specifically to ETX polypeptide or its binding protein, such as MAL. The term "monoclonal antibody" as used herein, refers to an antibody which displays a single binding specificity and affinity for a particular epitope. Accordingly, the term "human monoclonal antibody" refers to an antibody which displays a single binding specificity and which has variable and constant regions derived from human germline or non-germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term an "isolated antibody" is intended to refer to an antibody which is substantially free of other antibodies having different antigenic specificities (e.g., an isolated antibody that specifically binds to ETX or its binding receptor, such as MAL or HAvR-1, respectively, is substantially free of antibodies that do not bind to ETX or its binding receptor, respectively). An isolated antibody that specifically binds to an epitope of ETX and/or its binding receptor may, however, have cross-reactivity to other ETX protein or its binding receptor, respectively, from different bacterial strains. In addition, an isolated antibody is typically substantially free of other cellular material and/or chemicals.

As used herein, the term "humanized antibody" refers to an antibody that consists of the CDR of antibodies derived from mammals other than human, and the FR region and the constant region of a human antibody. A humanized antibody is useful as an effective component in a therapeutic agent according to the present invention since antigenicity of the humanized antibody in human body is lowered.

As used herein, the term "composite antibody" refers to an antibody which has variable regions comprising germline or non-germline immunoglobulin sequences from two or more unrelated variable regions. Additionally, the term "composite, human antibody" refers to an antibody which has constant regions derived from human germline or non-germline immunoglobulin sequences and variable regions comprising human germline or non-germline sequences from two or more unrelated human variable regions. A composite, human antibody is useful as an effective component in a therapeutic agent according to the present invention since the antigenicity of the composite, human antibody in human body is lowered.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, the term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

In certain embodiments, the antibody is any known or later developed neutralizing antibody against ETX protein. Examples of such ETX antibodies are describe by Bentancor et al., Percival et al., Uzal et al., and Veschi et al., the entire content of each of which references is incorporated by reference herewith. In certain embodiments, the neutralizing antibody against ETX protein comprises an amino acid sequence at least about 71%, 75%, 80%, 85%, 90%, 91%, 92%, 93%, 94%, 95%, 96% 97%, 98%, 99%, 99.5%, or 99.9% or more identical to a polypeptide(s) of any known or later developed ETX antibodies.

Antibodies to ETX or its binding receptor described herein may be produced using any methods described herein or known in the art. Monoclonal antibodies (e.g., human antibodies) that specifically binds to ETX or its binding protein, such as MAL protein, respectively, can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes. One method for generating hybridomas which produce monoclonal antibodies against ETX or its binding receptor, such as MAL, respectively, is the murine system. Hybridoma production in the mouse is well known in the art, including immunization protocols and techniques for isolating and fusing immunized splenocytes.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) Nature 256:495-497) (see also Brown et al. (1981) J. Immunol. 127:539-46; Brown et al. (1980) J. Biol. Chem. 255:4980-83; Yeh et al. (1976) Proc. Natl. Acad. Sci. 76:2927-31; and Yeh et al. (1982) Int. J. Cancer 29:269-75), the more recent human B cell hybridoma technique (Kozbor et al. (1983) Immunol. Today 4:72), the EBV-hybridoma technique (Cole et al. (1985) Monoclonal Antibodies and Cancer Therapy, Alan R. Liss, Inc., pp. 77-96) or trioma techniques. The technology for producing monoclonal antibody hybridomas is well known in the art. Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, such as ETX or its binding receptor, e.g., MAL protein, preferably specifically.

Any of the many well known protocols used for fusing lymphocytes and immortalized cell lines can be applied for the purpose of generating an anti-ETX, or anti-MAL or anti-HAvR-1 monoclonal antibody. Moreover, one ordinary skilled in the art will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody against ETX or its binding receptor, respectively, are detected by screening the hybridoma culture supernatants for antibodies that bind a given polypeptide, e.g., ETX or its binding receptor, respectively, using a standard ELISA assay.

As an alternative to preparing monoclonal antibody-secreting hybridomas, a monoclonal specific for ETX or its binding receptor polypeptide, respectively, can be identified and isolated by screening a recombinant combinatorial immunoglobulin library (e.g., an antibody phage display library) with the appropriate polypeptide to thereby isolate immunoglobulin library members that bind said appropriate polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening an antibody display library are known in the art.

Additionally, recombinant anti-ETX, anti-MAL, or anti-HAvR-1 antibodies, such as chimeric, composite, and humanized monoclonal antibodies, which can be made using standard recombinant DNA techniques, can be generated. Such chimeric, composite, and humanized monoclonal antibodies can be produced by recombinant DNA techniques known in the art.

In addition, humanized antibodies can be made according to standard protocols known in the art. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art. The use of intracellular antibodies to inhibit protein function in a cell is also known in the art.

In another embodiment, human monoclonal antibodies directed against ETX or its binding receptor, such as MAL or HAvR-1, respectively, can be generated using transgenic or transchromosomal mice carrying parts of the human immune system rather than the mouse system. In one embodiment, transgenic mice, referred to herein as "HuMAb mice" which contain a human immunoglobulin gene mini-loci that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg, N. et al. (1994) Nature 368(6474): 856 859). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal antibodies (Lonberg, N. et al. (1994), supra; reviewed in Lonberg, N. (1994) Handbook of Experimental Pharmacology 113:49 101; Lonberg, N. and Huszar, D. (1995) Intern. Rev. Immunol. Vol. 13: 65 93, and Harding, F. and Lonberg, N. (1995) Ann. N.Y Acad. Sci 764:536 546). The preparation of HuMAb mice is known in the art.

In another embodiment, an antibody for use in the invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Bispecific antibodies have been constructed by chemical means known in the art. Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to ETX and its binding receptor polypeptide. In one embodiment, the bispecific antibody could specifically bind to both ETX and its binding receptor polypeptide, MAL or HAvR-1.

Yet another aspect of the invention pertains to anti-ETX, anti-MAL, or anti-HAvR-1 antibodies that are obtainable by a process comprising, immunizing an animal with an immunogenic ETX, MAL or HAvR-1 polypeptide, respectively, or an immunogenic portion thereof; and then isolating from the animal antibodies that specifically bind to the polypeptide.

In still another aspect of the invention, partial or known antibody sequences can be used to generate and/or express new antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. Such framework sequences can be obtained from public DNA databases that include germline or non-germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody. Partial heavy and light chain sequence spanning the CDR regions is typically sufficient for this purpose. The partial sequence is used to determine which germline and/or non-germline variable and joining gene segments contributed to the recombined antibody variable genes. The germline and/or non-germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons. The process can also be used to screen libraries of particular immunoglobulin encoding sequences in one species (e.g., human) to design cognate immunoglobulin encoding sequences from known antibody sequence in another species (e.g., mouse).

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266L19867019870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for this use are known in the art. Fully human and chimeric antibodies against ETX or its binding receptor, respectively, also include IgG2, IgG3, IgE, IgA, IgM, and IgD antibodies. Similar plasmids can be constructed for expression of other heavy chain isotypes, or for expression of antibodies comprising lambda light chains. Thus, the structural features of known, non-human or human antibodies (e.g., a mouse anti-human anti-ETX or anti-MAL antibody) are used to create structurally related human anti-human anti-ETX or anti-MAL antibodies that retain at least one functional property of the antibodies, such as binding to ETX or MAL, respectively. Another functional property includes inhibiting binding of anti-ETX to ETX or anti-MAL to MAL in a competition ELISA assay. In addition, one or more CDR or variable regions of these antibodies can be combined recombinantly with known human framework regions and CDRs to create additional, recombinantly-engineered, human anti-ETX or anti-MAL antibodies.

Since it is well known in the art that antibody heavy and light chain CDR3 domains play a particularly important role in the binding specificity/affinity of an antibody for an antigen, the recombinant anti-ETX or anti-MAL or anti-HAvR-1 antibodies prepared as set forth above preferably comprise the heavy and light chain CDR3s of variable regions. In certain embodiments, the antibodies further can comprise the CDR2s of variable regions. In other embodiments, the antibodies further can comprise the CDR1s of variable regions. The antibodies can further comprise any combinations of the CDRs.

The CDR1, 2, and/or 3 regions of the engineered antibodies described above can comprise the exact amino acid sequence(s) as those of variable regions of the present invention disclosed herein. However, the ordinarily skilled artisan will appreciate that some deviation from the exact CDR sequences may be possible while still retaining the ability of the antibody to bind ETX and/or its binding receptor, MAL or HAvR-1 effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of these antibodies.

In addition to simply binding ETX and/or its binding receptor, engineered antibodies such as those described above may be selected for their retention of other functional properties, such as: (1) binding to human ETX or its binding receptor, e.g., MAL or HAvR-1; (2) inhibiting binding of anti-ETX to ETX, anti-MAL to MAL, or anti-HAvR-1 to HAvR-1; (3) binding to MAL and inhibiting the ability of the bound MAL to bind to ETX; (4) binding to HAvR-1 and inhibiting the ability of the bound HAvR-1 to bind to ETX.

Antibodies' activity in inhibiting binding of ETX to its binding receptor can be determined by testing the ability of the antibody from blocking the binding of ETX to its binding receptor. A competition ELISA assay in the presence of a labeled ligand and/or the antibody may be used. For example, to determine if an anti-ETX antibody could block the interaction between ETX and MAL or HAcR-1, a competitive binding experiment is performed. Cells expressing MAL or HAvR-1 is preincubated with the anti-ETX antibody followed by the addition of biotinylated MAL-Ig fusion protein. If the anti-ETX antibody blocks the binding of MAL-Ig in a dose-dependent manner and with high avidity, the anti-ETX antibody is considered as being effective in inhibiting the interaction between ETX and MAL. Similar tests may be carried out to test antibodies that are effective in inhibiting the interaction of ETX and HAvR-1.

One aspect of the invention pertains to isolated polypeptides of ETX, its binding receptor, MAL or HAvR-1, and antibodies and antigen-binding fragments thereof described herein ("the polypeptides of the invention"), and biologically active portions thereof. In one embodiment, the polypeptides of the invention, and biologically active portions thereof can be isolated from cells or tissue sources by an appropriate purification scheme using standard protein purification techniques. In another embodiment, the polypeptides of the invention, and biologically active portions thereof are produced by recombinant DNA techniques. Alternatively, the polypeptides of the invention, and biologically active portions thereof can be chemically synthesized using standard peptide synthesis techniques.

An "isolated" or "purified" polypeptide or biologically active portion thereof is substantially free of cellular material or other contaminating proteins from the cell or tissue source from which the polypeptides of the invention are derived, or substantially free from chemical precursors or other chemicals when chemically synthesized. The language "substantially free of cellular material" includes preparations of the polypeptide(s) of the invention, and biologically active portions thereof, in which the polypeptide is separated from cellular components of the cells from which it is isolated or recombinantly produced. In one embodiment, the language "substantially free of cellular material" includes preparations of the polypeptide(s) of the invention, and biologically active portions thereof having less than about 30%, 20%, 10%, 5% (by dry weight) of other "contaminating protein." When the polypeptides of the invention or biologically active portion thereof are recombinantly produced, it is also substantially free of culture medium, i.e., culture medium represents less than about 20%, 10%, 5% of the volume of the protein preparation.

The language "substantially free of chemical precursors or other chemicals" includes preparations of the polypeptide(s) of the invention or biologically active portion thereof in which the polypeptide is separated from chemical precursors or other chemicals which are involved in the synthesis of the polypeptide. In one embodiment, the language "substantially free of chemical precursors or other chemicals" includes preparations of polypeptide(s) of the invention or biologically active portion thereof having less than about 30%, 20%, 10% or 5% (by dry weight) of chemical precursors or of proteins not of the invention.

As used herein, a "biologically active portion" of polypeptide(s) of the invention include polypeptides which participates in an interaction between ETX and its binding receptor, such as MAL or HAvR-1, or anti-ETX to ETX, or anti-MAL to MAL, or anti-HAvR-1 to HAvR-1. Biologically active portions of a polypeptide(s) of the invention include peptides comprising amino acid sequences sufficiently identical to or derived from the amino acid sequence of polypeptide(s) of the invention, which include fewer amino acids than the respective, full length polypeptide(s) of the invention, and exhibit at least one activity of the respective polypeptide(s) of invention. In one embodiment, biologically active portions comprise a domain or motif with the ability to specifically bind ETX or its binding receptor according to the antigen, respectively, to which it was raised or designed to bind. Biologically active portions of polypeptide(s) of the invention can be used as targets for developing agents which modulate an activity mediated by ETX or its binding receptor, MAL, e.g., immune cell activation or suppression.

In certain embodiments, the ETX polypeptide of the invention has an amino acid sequence as set forth in SEQ ID NOs:1 (amino acid sequence) and 2 (nucleotide sequence). In other embodiments, the MAL protein of the invention has at least four isoforms (a, b, c, and d), each isoform has an amino acid sequence as set forth in SEQ ID NOs: 3, 4, 5, and 6. In other embodiments, the HAvR-1 protein has an amino acid sequence as set forth in SEQ ID NO: 7. In other embodiments, the polypeptide of the invention is substantially identical to the amino acid sequences of the above polypeptide(s), and retains the functional activity of the respective polypeptide(s). Accordingly, in another embodiment, a polypeptide(s) of the invention is a polypeptide which comprises an amino acid sequence at least about 71%, 75%, 80%, 85%, 90%, 91%, 92%, 93%, 94%, 95%, 96% 97%, 98%, 99%, 99.5%, or 99.9% or more identical to a polypeptide(s) as set forth in the above SEQ ID NOs: 1, 3, 4, 5, 6, and 7.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In one embodiment, the length of a reference sequence aligned for comparison purposes is at least 30%, 40%, 50%, 60%, 70%, 80%, 90%, 95%, 96%, 97%, 98%, 99%, 99.5%, or 99.9% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also provides chimeric or fusion proteins. As used herein, a "chimeric protein" or "fusion protein" comprises a polypeptide(s) of the invention operatively linked to a polypeptide not of the invention. A "polypeptide(s) of the present invention" refers to a polypeptide having an amino acid sequence corresponding to a polypeptide of ETX, MAL, or HAvR-1, and their antibody or antigen-binding portion thereof, whereas a "polypeptide not of the present invention" refers to a polypeptide not having an amino acid sequence corresponding to a polypeptide which is not substantially homologous to a polypeptide shown in SEQ ID NOs.:1-7, e.g., a polypeptide which is different from a polypeptide mentioned above, and which is derived from the same or a different organism. Within the fusion protein, the term "operatively linked" is intended to indicate that the polypeptide(s) of the invention and the polypeptide(s) not of the invention are fused in-frame to each other. The polypeptide(s) not of the invention can be fused to the N-terminus or C-terminus of the polypeptide(s) of the invention and corresponds to a moiety that alters the solubility, binding affinity, stability, or valency of the polypeptide(s) of the invention.

For example, in one embodiment, the fusion protein is a GST fusion protein with a polypeptide(s) of the invention.

Such fusion proteins can facilitate the purification of recombinant polypeptides of the invention. In another embodiment, the fusion protein contains a heterologous signal sequence at its N-terminus. In certain host cells (e.g., mammalian host cells), expression and/or secretion of polypeptide(s) of the invention can be increased through use of a heterologous signal sequence.

A chimeric or fusion polypeptide(s) of the invention can be produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, Ausubel et al., eds., John Wiley & Sons: 1992). Moreover, many expression vectors are commercially available that already encode a fusion moiety (e.g., a GST polypeptide).

The amino acid sequences of polypeptide(s) of the invention identified herein will enable those of skill in the art to produce polypeptides corresponding to polypeptide(s) of the invention. Such polypeptides can be produced in prokaryotic or eukaryotic host cells by expression of polynucleotides encoding a polypeptide(s) of the invention. Alternatively, such peptides can be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N. Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu. Rev. Biochem. 57:957; and Offord, R. E. (1980) Semisynthetic Proteins, Wiley Publishing, which are incorporated herein by reference).

In certain embodiments, the invention provides that inhibitors of the receptor on the blood brain barrier (BBB), such as HAVcR-1, can also be therapeutic candidates for protecting and/or treating MS. Compounds that have been found to potentially inhibit HAVcR-1 include, but not limited to, the mutant epsilon toxins, such as ETX-Y29E, ETX-Y30E, ETX-Y36E and ETX-Y196E. In certain embodiments, the ETX-H106P mutant is another candidate for an ETX receptor antagonist. Inhibitors of other receptors on the BBB are also contemplated in the invention. As used herein, the term "inhibitor" or "antagonist" refer to an agent or molecule that decrease, limit, or block, for example, a particular action, function, or interaction. In certain embodiments, the inhibitors are small molecule inhibitors of C. perfringens ϵ-tocin cytotoxicity, such inhibitors are now known in the art or later developed. Examples of such inhibitors are described in Lewis et al. (Toxins 2010, 2, 1825-1847), the entire content of which is incorporated by reference herewith.

In certain embodiments, the inventive method comprises an agent that is a phage lytic enzyme specific for *Clostridium perfringens* Type B or D bacterial strain. In one embodiment, such phage lytic enzyme is a muramidase PlyCM derived from strain ATCC 13124. In certain embodiments, the agent of the invention for protecting or treating MS in human is a probiotic supplement comprising *C. perfringens* type A or other bacteria type that can effectively outcompete *Clostridium perfringens* type B or D, with no other *C. perfringens* toxinotype. In certain embodiments, the probiotic supplement contains *C. perfringens* type A bacterial strain since its toxinotype has been shown to outcompete *C. perfringens* type B. The probiotic approach is being developed in various markets. Typical bacteria strains included in probiotic supplement preparations include, but are not limited to, *Lactobacillus acidophilus, L. bulgaricus, L. casie, L. fermentum, L. Plantarum, Rhodoseudomonas palustris, Saccharomyces cerevisiae*, and *Steptococcus thermophiles*. These strains are common in various human foods and are ubiquitously used in manufacturing of probiotic dietary supplement products for human, animal and aquaculture health. The invention encompasses any bacterial phage lytic enzymes and/or probiotic supplement, now known or later developed, that specific for and/or outcompete *Clostridium perfringens* type B or D bacterial strain. In some cases the bacteriophage lytic enzyme can be delivered in a probiotic organism by genetically engineering that organism to expressed enzymes specifically lytic to *Clostridium perfringens*.

In certain embodiments, the invention method comprises an agent is a vaccine against *Clostridium perfringens* type B or type D bacterial strain, or the epsilon toxin (ETX) produced therefrom. Biological preparation for a vaccine that improves immunity to a particular disease is well known in the art. Several such vaccines have been developed and employed to protect animals from *Clostridium perfringens* infections, and recombinant forms are in development. More specifically, vaccines and/or methods of making thereof, for *Clostridium perfringens* bacterial strains are well known in the art and/or described, for example, in U.S. Pat. No. 6,403,094 to Titball et al.; Titball (Vaccine 27, 2009, D44-D47); and other literatures, for instance, Chandran et al. (Clinical and Vaccine Immunology, 2010, p. 1013-1016); and de la Rosa et al. (J ANIM Sci 1997, 75: 2328-2334), the entire contents of each of which are incorporated by reference in its entirety.

The invention method further comprises an antibiotic sufficient to kill off *C. perfringens* type B or D bacterial strain. Antibiotics found to be effective against *C. perfringens* include, but are not limited to, penicillin, ampicillin, amoxicillin, metronidazole, erythromycin, and tylosin. The invention encompasses any known and currently available or any later developed antibiotics that are effective against *C. perfringens* type B or D bacterial strain.

In certain embodiments, one or more agents used in the inventive methods for protecting and/or treating MS in human can be administered separatedly in a separately formulated composition each comprising a pharmaceutically suitable and acceptable carrier or adjuvant mixed with the agents. In other embodiments, one or more such agents can be combined and/or formulated together in a composition further comprising a pharmaceutically suitable and acceptable carrier or adjuvant mixed with these agents. The composition of the invention can be formulated in any pharmaceutically suitable and/or acceptable formulations for any suitable and/or acceptable administration routes, including, but not limited to, oral tablet or capsule, parental injectable solution or suspension, or subcutaneous patches. The composition of the invention can be administered alone, or in combination with any suitable agent or compound to enhance the effect for prevention and treatment of MS in human, and/or reduce any syndroms directed or indirected associated with MS disease and/or side effects resulted from the treatment.

The invention further provides a composition, e.g., a pharmaceutical composition, containing one or a combination of the monoclonal antibodies, or antigen-binding portion(s) thereof (such as antigen-binding fragments), of the invention, formulated together with a pharmaceutically acceptable carrier. In one embodiment, the compositions include a combination of multiple (e.g., two or more) isolated antibodies of the invention, each of the antibodies of the composition binds to a distinct, pre-selected epitope of ETX, or its binding receptor, such as MAL or HAvR-1. The invention further provides a composition for preventing or treating multiple sclerosis (MS) in a human subject in need comprising an effective amount of an agent that directly or indirectly interferes with epsilon toxin (ETX) produced by *Clostridium perfringens* type B or type D bacterial strain, an ETX-binding receptor, or an interaction of ETX with its binding receptor so as to inhibit or suppress ETX modulated receptor signaling activities.

Pharmaceutical compositions of the invention also can be administered in combination therapy, i.e., combined with other agents. For example, the combination therapy can include a composition of the invention with at least one or more additional therapeutic agents. The pharmaceutical compositions of the invention can also be administered in conjunction with any other therapy. Co-administration with other antibodies are also encompassed by the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the human antibodies of the invention may be administered once or twice weekly by subcutaneous injection or once or twice monthly by subcutaneous injection. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In one embodiment, an agent of the invention is an antibody. As defined herein, a therapeutically effective amount of antibody (i.e., an effective dosage) ranges from about 0.001 to 30 mg/kg body weight, or about 0.01 to 25 mg/kg body weight, or about 0.1 to 20 mg/kg body weight, or about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. It will also be appreciated that the effective dosage of antibody used for treatment may increase or decrease over the course of a particular treatment. Changes in dosage may result from the results of diagnostic assays.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, alternatively from about 0.005 percent to about 70 percent, or alternatively from about 0.01 percent to about 30 percent.

Formulations of the invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the invention are administered as pharmaceuticals, to humans, they can be given alone or as a pharmaceutical composition containing, for example, 0.001 to 90% (e.g., 0.005 to 70%, such as 0.01 to 30%) of active ingredient in combination with a pharmaceutically acceptable carrier.

Regardless of the route of administration selected, the compounds of the invention, which may be used in a suitable hydrated form, and/or the pharmaceutical compositions of the invention, are formulated into pharmaceutically acceptable dosage forms by conventional methods known to those of skill in the art.

Actual dosage levels of the active ingredients in the pharmaceutical compositions of the invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician having ordinary skill in the art can readily determine and prescribe the effective amount of the pharmaceutical composition required. For example, the physician could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in one embodiment, a therapeutic composition of the invention can be administered with a needleless hypodermic injection device. Examples of well-known implants and modules useful in the invention include an implantable micro-infusion pump for dispensing medication at a controlled rate; a therapeutic device for administering medicants through the skin; a medication infusion pump for delivering medication at a precise infusion rate; a variable flow implantable infusion apparatus for continuous drug delivery; an osmotic drug delivery system having multi-chamber compartments; and an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. methods of manufacturing liposomes are well known in the art. The liposomes may comprise one or more moieties which are selectively transported into specific cells or organs, thus enhance targeted drug delivery. Exemplary targeting moieties include folate or biotin; mannosides; antibodies; surfactant protein A receptor, different species of which may comprise the formulations of the inventions, as well as components of the invented molecules. In one embodiment of the invention, the therapeutic compounds of the invention are formulated in liposomes; in another embodiment, the liposomes include a targeting moiety. In yet another embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

The antibodies (including derivatives and conjugates of the antibodies) and/or inhibitors or antagonists described herein and compositions containing the antibodies and/or inhibitors or antagonist can be used in a variety of in vitro and in vivo diagnostic and therapeutic applications. For example, anti-ETX binding to ETX transmits an inhibitory signal via its interaction with its binding receptor MAL or HAvR-1. Thus, modulation of the interaction between ETX and its binding receptor (e.g., MAL or HAvR-1), results in modulation/inhibition of the downstream signaling activities. In particular, antibodies described herein are useful for diagnostic, prognostic, prevention, and therapeutic applications related to MS in human mediated by ETX produced by the *C. perfringens* type B and/or D bacterial strain.

A human subject is treated if one or more beneficial or desired results, including desirably clinical results, are obtained. For purposes of this invention, beneficial or desired clinical results include, but are not limited to, one or more of the following: decreasing one or more symptoms resulting from the disease, increasing the quality of life of those suffering from the disease, decreasing the dose of other medications required to treat the disease, delaying the progression of the disease, and/or prolonging survival of individuals.

In one aspect, the invention relates to a method for preventing in a human subject from MS. Human subjects at risk for MS that would benefit from treatment with the claimed antibodies or methods can be identified, for example, by any or a combination of diagnostic or prognostic assays known in the art. Administration of a prophylactic antibody or vaccine can occur prior to the manifestation of symptoms associated with MS. The appropriate antibody and/or inhibitors or antagonists used for prevention or treatment can be determined based on clinical indications and can be identified, e.g., using screening assays described herein.

The invention further provides a method for diagnosis or prognosis of a human subject at risk of multiple sclerosis (MS) comprising: a) obtaining a biological sample from said subject; b) detecting an expression or activity level of ETX gene or protein, or presence of *C. perfringens* type B or D bacterial strain in the biological sample from said subject, and c) diagnosing the subject at risk for MS when an elevated expression or activity level of ETX gene or protein or the presence of *C. perfringens* type B or D bacterial strain is detected as compared to the referenced level. In certain embodiments, biological sample is a biological fluid selected from the group consisting of whole blood, plasma, serum, tears, saliva, mucous, cerebrospinal fluid, urine, and stool.

Kits for diagnosing a human subject at risk for or providing a prognosis of a human subject with multiple sclerosis (MS) are also encompassed by the invention. The kit comprises: a) a capture reagent comprising one or more detectors specific for ETX gene or protein, or for *C. perfringens* type B or D bacterial strain; b) a detection reagent;

and c) an instruction for using the kit to diagnose said subject at risk for or provide a prognosis of said subject with MS when an elevated expression or activity level of ETX gene or protein or the presence of *C. perfringens* type B or D bacterial strain is detected as compared to the referenced level.

As discussed above, the invention provides *Clostridium Perfringens* epsilon toxin (ETX) is a causative agent for Multiple Sclerosis. An important step in the pathophysiologic mechanism by which *Clostridium Perfringens* epsilon toxin (ETX) causes new lesion formation in MS requires entry of toxin from the gastrointestinal tract into the bloodstream. Lymphocytes express the *Clostridium Perfringens* epsilon toxin receptor (Myelin and Lymphocyte Protein: MAL) and thus toxin within the blood binds to human lymphocytes with high affinity. Accordingly, in certain embodiments, the invention provides a method to detect *Clostridium Perfringens* epsilon toxin (ETX) bound to lymphocytes through the use of specific antibodies directed against *Clostridium Perfringens* epsilon toxin (ETX). Human lymphocytes or blood mononuclear cells were incubated with the *Clostridium Perfringens* epsilon toxin (ETX) specific antibodies, washed, and then incubated with a relevant fluorescently tagged secondary antibody. Fluorescence Activated Cell Sorting or Flow Cytometry can be used to detect cells binding both *Clostridium Perfringens* epsilon toxin (ETX) specific antibodies and human lymphocyte specific antibodies (such as but not limited to anti-CD3). In addition to detecting the binding of *Clostridium Perfringens* epsilon toxin (ETX) specific antibodies to lymphocytes, the invention further provides a method to detect alterations in lymphocyte volume and membrane characteristics induced by epsilon toxin.

The invention further provides a method of screening for a candidate agent that is capable of inhibiting or suppressing gene or protein expression or activity level of ETX or ETX-binding receptor, or inhibiting binding capability of ETX to its binding receptor so as to inhibit or suppress ETX-receptor signaling function. The screening method comprises the steps of: a) exposing a candidate agent with gene or protein of ETX or ETX-binding receptor, b) determining an binding affinity of said candidate agent to said gene or protein of ETX or ETX-binding receptor; and c) identifying said candidate agent as an inhibitor or suppressor for ETX or ETX-binding receptor when the candidate agent binds to said gene or protein of ETX or ETX-binding receptor or modulates their activities.

One aspect of the invention relates to methods that utilize screening assays, including cell based and non-cell based assays. In one embodiment, the assays provide a method for identifying antibodies which modulate the interaction of ETX and its binding receptor, such as MAL or HAvR-1. In one embodiment, the invention relates to assays for screening candidate or antibodies which bind to, or modulate the activity of, ETX e.g., modulate the ability of the polypeptide to interact with (e.g., bind to) its cognate binding partner or receptor, e.g., MAL or HAvR-1.

In one embodiment, an assay is a cell-based assay, comprising contacting a cell expressing ETX or its binding receptor, with a candidate compound or antibody and determining the ability of the candidate compound or antibody to modulate (e.g. inhibit) the binding of ETX to its binding receptor MAL or HAvR-1. Determining the ability of ETX to bind to, or interact with, its binding receptor MAL or HAvR-1 can be accomplished, e.g., by measuring direct binding or by measuring a parameter of downstream signaling activities.

For example, in a direct binding assay, the ETX, its binding receptor (or their respective target polypeptides) can be coupled with a radioisotope or enzymatic label such that binding of the candidate compound or antibody binding to ETX or its binding receptor MAL or HAvR-1 can be determined by detecting the labeled protein in a complex. For example, EXT or its binding receptor MAL or HAvR-1 can be labeled with $^{125}I$, $^{35}S$, $^{14}C$, or $^{3}H$, either directly or indirectly, and the radioisotope detected by direct counting of radioemission or by scintillation counting. Alternatively, EXT or its binding receptor MAL or HAvR-1 can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound or antibody to modulate the interaction between ETX and its binding receptor MAL or HAvR-1, without the labeling of any of the interactants. For example, a microphysiometer can be used to detect the interaction of ETX and its binding receptor MAL or HAvR-1. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In another embodiment, determining the ability of the antibody to antagonize the interaction between a given set of polypeptides can be accomplished by determining the activity of one or more members of the set of polypeptides. For example, the activity of ETX or its binding receptor can be determined by detecting induction of a cellular second messenger, detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by ETX or its binding receptor. Determining the ability of the antibody to bind to or interact with said polypeptide can be accomplished, for example, by measuring the ability of a compound to modulate immune cell costimulation or inhibition in a proliferation assay, or by interfering with the ability of said polypeptide to bind to antibodies that recognize a portion thereof.

Antibodies that block or inhibit interaction of ETX with its binding receptor can be identified by their ability to inhibit immune cell proliferation, and/or effector function, or to induce anergy when added to an in vitro assay. For example, cells can be cultured in the presence of an agent that stimulates signal transduction via an activating receptor. A number of recognized readouts of cell activation can be employed to measure, cell proliferation or effector function (e.g., antibody production, cytokine production, phagocytosis) in the presence of the activating agent. The ability of a test antibody to block this activation can be readily determined by measuring the ability of the antibody to affect a decrease in proliferation or effector function being measured, using techniques known in the art.

In other embodiments, an assay of the invention is a cell-free assay in which ETX, its binding receptor, or a biologically active portion thereof, is contacted with a candidate compound or antibody, and the ability of the candidate compound or antibody to bind to the ETX or its binding receptor polypeptide, or biologically active portion thereof, is determined. Binding of the candidate compound or antibody to the ETX or its binding receptor polypeptide can be determined either directly or indirectly as described above. In still another embodiment, the assay includes contacting the polypeptide, or biologically active portion thereof, with its binding partner to form an assay mixture, contacting the assay mixture with a candidate compound or antibody, and determining the ability of the candidate compound or antibody to interact with the polypeptide in the assay mixture, wherein determining the ability of the candidate compound or antibody to interact with the polypeptide comprises determining the ability of the candidate compound or antibody to preferentially bind to the polypeptide or biologically active portion thereof, as compared to the binding partner.

For example, ETX or its binding receptor polypeptide can be used to form an assay mixture and the ability of a candidate compound or antibody to block this interaction can be tested by determining the ability of ETX binding to its binding receptor and determining the ability of ETX to bind its binding receptor, by one of the methods described above for determining binding. Determining the ability of ETX to bind its binding receptor MAL or HAvR-1 can also be accomplished using a technology such as real-time Biomolecular Interaction Analysis (BIA) (Sjolander, S. and Urbaniczky, C. (1991) Anal. Chem. 63:2338-2345 and Szabo et al. (1995) Curr. Opin. Struct. Biol. 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. ETX or its binding receptor polypeptide can be immobilized on a BIAcore chip and antibodies can be tested for binding to ETX or its binding receptor. An example of using the BIA technology is described by Fitz et al. (1997) Oncogene 15:613.

The cell-free assays of the invention are amenable to use of both soluble and/or membrane-bound forms of proteins (e.g., ETX or its binding receptor MAL or HAvR-1, or biologically active portions thereof). In the case of cell-free assays in which a membrane-bound form protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton™ X-100, Triton™ X-114, Thesit™, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl, N,N-dimethyl-3-ammonio-1-propane sulfonate.

In one or more embodiments of the above described assay methods, it may be desirable to immobilize either ETX or its binding receptor MAL or HAvR-1, or an appropriate target polypeptide, to facilitate separation of complexed from uncomplexed forms of one or both of the proteins, as well as to accommodate automation of the assay. Binding of a candidate compound or antibody to ETX or its binding receptor can be accomplished in any vessel suitable for containing the reactants. Examples of such vessels include microtiter plates, test tubes, and micro-centrifuge tubes. Binding of a candidate compound or an antibody to ETX can be accomplished by fluorescent detection using FACS. For example, ETX bound to lymphocytes derived from an MS patient can be detected using an antibody directed against ETX and a flourescently tagged secondary antibody directed against the primary anti-ETX antibody. Detection of flourescently tagged cells is then accomplished by FACS. In one embodiment, a fusion protein can be provided which adds a domain that allows one or both of the proteins to be bound to a matrix. For example, glutathione-S-transferase/ETX, /MAL, or /HAvR-1 polypeptide fusion proteins, or glutathione-S-transferase/candidate fusion proteins, can be adsorbed onto glutathione sepharose beads (Sigma Chemical, St. Louis, Mo.) or glutathione derivatized microtiter plates, which are then combined with the test compound or antibody, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of ETX or its binding receptor polypeptide binding or activity determined using standard techniques.

In an alternative embodiment, determining the ability of the candidate compound or antibody to modulate the activity of ETX or its binding receptor can be accomplished by determining the ability of the candidate compound or antibody to modulate the activity of a polypeptide that functions downstream of ETX-receptor signaling, e.g., a polypeptide that interacts with ETX, or a polypeptide that functions downstream of ETX-receptor binding. For example, levels of second messengers can be determined, the activity of the interactor polypeptide on an appropriate target can be determined, or the binding of the interactor to an appropriate target can be determined as previously described.

This invention further pertains to novel inhibitors, antagonists, and/or antibodies identified by the above-described screening assays. Accordingly, it is within the scope of this invention to further use the candidate inhibitor, antagonist, and/or antibody identified as described herein in an appropriate animal model. For example, an antibody identified as described herein can be used in an animal model to determine the efficacy, toxicity, or side effects of treatment with such an antibody. Alternatively, an antibody identified as described herein can be used in an animal model to determine the mechanism of action of such an antibody. Furthermore, this invention pertains to uses of novel candidate inhibitors, antagonists, and/or antibodies identified by the above-described screening assays for treatments as described herein.

EXAMPLES

The present description is further illustrated by the following examples, which should not be construed as limiting in any way. The contents of all cited references (including literature references, issued patents, published patent applications as cited throughout this application) are hereby expressly incorporated by reference.

Example 1

General Methods

Fluorescent Labeling of ETX and Immunofluorescence

His tagged protoxin was procured from BEI Resources and 1 mg was fluorescently labeled using Alexa Fluor 594 Protein labeling Kit (Invitrogen) as per manufacturer's instructions. Fixed frozen coronal sections were permeabilized in a 1% sodium cholate, 1% BSA, 10% donkey serum, PBST solution overnight at 4° C.[20]. Sections were then incubated with rabbit anti-PLP (ThermoScientific) at 1:1000 overnight at 4° C. Following three washes with PBS, sections were then incubated with Donkey anti-rabbit Alexa 488 (Jackson ImmunoResearch) at 1:1000, and Alexa 594 labeled His-tagged protoxin (50 nM) for 2 hrs at RT. The stained tissue was washed 3× in PBS and prepared for microscopy at the Rockefeller Bio-Imaging facility.

Sample Collection/Fecal Culture/PCR Analysis

Stool specimens were self-collected by patients and healthy controls in a clean single use vessel and stored at −20° C. until returned to the MS Center. Approximately one gram of stool was collected and stored in a fecal collection tube (Sarstedt) containing 9 ml of buffered glycerin-salt solution (10% glycerin, 71.2 mM $K_2HPO_4$, 29.4 mM $KH_2PO_4$, 71.9 mM NaCl made in distilled water, adjusted to pH 7.2 and autoclaved) under IRB protocol no. 1003010940. Upon receipt, samples were resuspended in 40 ml of modified rapid *perfringens* media[21]; D-cycloserine (400 mg/L) was substituted for neomycin/polymyxin B and litmus milk was omitted to improve DNA extraction. The resuspended samples were cultured in 50 ml falcon tubes with tightly closed caps at 47° C. ON.

DNA was extracted from 1 ml of culture supernatant using a Qiagen blood and tissue kit. Isolated DNA was used as template for the following PCR reactions; the following primers were used:

```
1) 16S rRNA (positive control) fwd primer:
                                     (SEQ ID NO: 8)
AGAGTTTGATCCTGGCTCA, reverse primer:
                                     (SEQ ID NO: 9)
GGTTACCTTGTTACGACTT 2) Alpha toxin (pan C. perfringens marker)
fwd primer:
                                     (SEQ ID NO: 10)
GCTAATGTTACTGCCGTTGA reverse primer:
                                     (SEQ ID NO: 11)
CCTCTGATACATCGTGTAAG 3) Beta toxin fwd primer:
                                     (SEQ ID NO: 12)
GCGAATATGCTGAATCATCTA, reverse primer:
                                     (SEQ ID NO: 13)
GCAGGAACATTAGTATATCTTC 4) Epsilon toxin fwd primer:
                                     (SEQ ID NO: 14)
GCGGTGATATCCATCTATTC, reverse primer:
                                     (SEQ ID NO: 15)
CCACTTACTTGTCCTACTAAC 5) B1RBB5 phage gene fwd primer:
                                     (SEQ ID NO: 16)
AAATGGACAAGAGGGATAAGGAT, reverse primer:
                                     (SEQ ID NO: 17)
TTTTCATCACAAATACCAGCCTC 6) B1RAA6 phage gene fwd primer:
                                     (SEQ ID NO: 18)
TTACAATAAAACCACATGAGCTT, reverse primer:
                                     (SEQ ID NO: 19)
TTTTATTTAACATACTCCGTTTT 7) Q8SBN7 phage gene fwd primer:
                                     (SEQ ID NO: 20)
GGGTGTCAAAGAAGATTTTAAAG, reverse primer:
                                     (SEQ ID NO: 21)
TTCTATCTTGCAACATTATATTT.
```

Serum and CSF Collection

CSF and sera from people with MS and healthy controls were collected at the Weill Cornell MS Center (IRB protocol no. 1003010940). Additional MS and Stroke CSF and sera were obtained from the Brain Research Institute, UCLA. SLE sera were purchased from Vital Products Inc.

Statistical Analysis

A two-tailed Chi squared test was performed to (1) compare the prevalence of commensal *Clostridium perfringens* type A in MS patients vs. healthy controls and (2) to compare the seroreactivity towards *C. perfringens* of MS patients to that of healthy controls.

Example 2

ETX Immunoreactivity in MS and Healthy Controls

Western blots were performed using human sera/CSF as primary antibody. SDS page electrophoresis was run and each well was loaded with a mixture of 100 ng of His tagged proETX (BEI Resources) and molar equivalents of PA63 (EMD Millipore) 190 ng, Cholera toxin beta FITC (Sigma Aldrich) 36 ng, His tagged Shiga toxin 1 beta (BEI Resources) 26 ng and His tagged Shiga toxin 2 beta (BEI Resources) 26 ng. Proteins were transferred to an Immobilon P membrane (Millipore) and probed with diluted sera/CSF. All serum and CSF samples were diluted 10,000 fold and 27 fold respectively, while SLE sera were diluted 100,000 fold to normalize background. HRP conjugated Donkey anti-human IgG 1:10,000 (Jackson Immunoresearch) was used to visualize human antibody binding.

Humoral immunity to epsilon toxin in mammals is transient and incomplete. For example, when vaccinated at t=0 and t=6 weeks with epsilon toxoid, only 50% of goats have protective anti-toxin titers at week nine[22]. By week 30, at the time of the 3$^{rd}$ vaccination only 2% of the goats maintain protective titers. At week 32 (2 weeks after the 3$^{rd}$ vaccination), 100% have protective titers, but by week 56 only 11% show protective titers[22]. Thus, in mammals exposed to epsilon toxin, seronegativity and seroreversion are common even when the toxin is administered with an adjuvant.

The sera and CSF from a cohort of MS patients, healthy controls and other diseases was screened for immunoreactivity to ETX by Western blot using the proETX protein. The Western blot assay was developed to rigorously exclude the likelihood of false positives. A sample was scored positive if there was clear immunoreactivity for ETX in conjunction with no immunoreactivity to four control toxins. Three of the controls were chosen to represent known gut derived toxins: Cholera toxin beta, Shiga toxin 1 beta and Shiga toxin 2 beta; no cross-reactions ever occurred with these control toxins. A fourth control, protective antigen 63 (PA63) from *Bacillus anthracis* was chosen because like ETX, PA63 is a pore-forming toxin with a hydrophobicity map similar to epsilon toxin[23]. PA63 was also chosen because most humans should be seronegative. Seroreactivity to PA63 would occur only in instances of vaccination or exposure to Anthrax. Most humans are not vaccinated against Anthrax and in this study; none of the patients or controls was vaccinated. Seroreactivity to PA63 could also be observed in people who have been infected with *Bacillus anthracis* and survived. Since pulmonary and gastrointestinal Anthrax is usually fatal or because like ETX, PA63 is a pore-forming toxin with a hydrophobicity map similar to epsilon toxin[23]. Seroreactivity to PA63 could also be observed in people who have been infected with debilitating, and since cutaneous Anthrax results in a characteristic black eschar, it is unlikely that prior Anthrax would be missed on a directed health questionnaire. Thus, positive immune reactivity to PA63 would strongly suggest non-specific interaction of host antibodies with PA63 or prior exposure to an antigen with a shared epitope. Thus, samples that showed immunoreactivity against ETX and PA63 were excluded since these indicated equivocal results. In SLE, where there is heightened humoral immunity, cross-reactions were common (FIG. 1). Since hydrophobic proteins are more likely to show non-specific interactions with antibodies, it is assumed that immunoreactivity to PA63 is nonspecific in nature.

It was found that 10% of MS patients and 1% of healthy controls, in a cross-sectional analysis, possessed ETX specific antibodies (p=0.0044) (FIG. 1). Based on the known low rates of seropositivity following immunization, and the common seroreversion rates[22], this 10% positivity presumably underestimates the true value of ETX exposure.

Example 3

Figure 2:
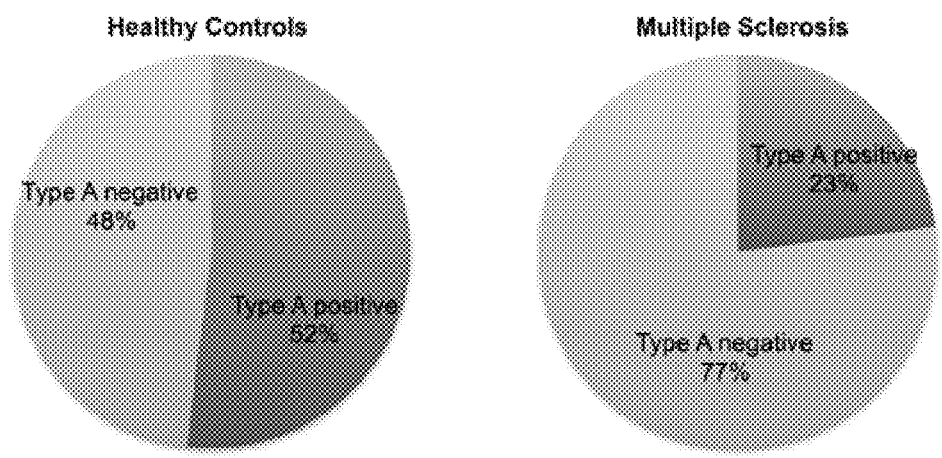
FIG. 2. The prevalence of *C. perfringens* type A, a human commensal, was determined in MS patients and healthy controls. Culture of stool in *C. perfringens* compatible growth medium revealed that 52% of healthy controls harbor *C. perfringens* type A in the gastrointestinal tract, whereas only 23% of people with MS harbor type A.

Reduced Prevalence of *C. perfringens* Type A in MS Compared to Healthy Controls Soil studies have identified that the presence of *C. perfringens* type A is coincident with the absence of other toxinotypes, suggesting that toxinotype A may compete with other *C. perfringens* toxinotpes for resources.[24] For these reasons the prevalence of Type A, a human commensal, was assessed in MS and healthy controls. Feces from 30 individuals with MS and 31 health controls were cultured. The bacteria were lysed, the DNA isolated and toxinotypes were determined by PCR analysis[10]. Prior published studies have demonstrated that type A is present in approximately 50% of healthy humans[25]. Consistent with this, this study found that 52% of the healthy controls (n=31) carried detectable type A (FIG. 2). However, only 23% *C. perfringens* type A carriage was found in individuals with MS (n=30), $\chi^2$p=0.0227 (FIG. 2). This finding supports that MS susceptibility may, in part, be due to host-microbiome influences and that the commensal *C. perfringens* type A may be protective.

Example 4

Figure 3:
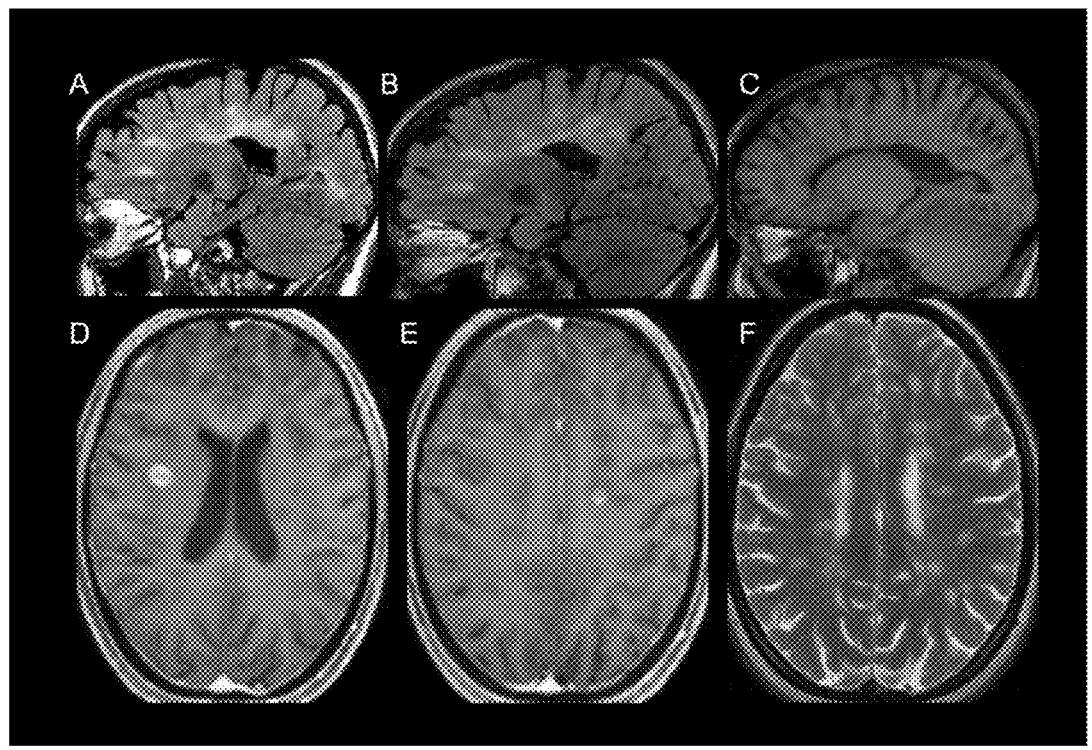
FIG. 3. Brain MRI of patient 73F. (3A) FLAIR image from September 2011 showing characteristic lesions in a parasagittal plane. (3B-3F) MRI from May 2012 revealing characteristic lesions on FLAIR imaging as before (3B), T1 hypointensities (3C), characteristic contrast enhancing lesions post IV Gadolinium (3D, 3E), and characteristic lesions on T2 weighted axial image (3F).

Identification of *Clostridium perfringens* Type B in a Woman with Multiple Sclerosis A 21-year old woman (patient 73F) developed left lower extremity dyscoordination, and imbalance that evolved to its maximum deficit over three days. Two weeks after onset she was referred to a neurologist due to persistent symptoms and neuroimaging of the brain revealed multiple foci of increased T2/flair signal in the deep and subcortical white matter, with several ovoid lesions within the corpus callosum characteristic of MS. Following administration of IV gadolinium, several lesions enhanced. CSF analysis revealed five IgG bands on isoelectric focusing that were not present in the corresponding serum sample. She met revised criteria for clinically definite relapsing remitting MS at the earliest clinical presentation termed a clinically isolated syndrome (CIS). She received five days of IV methylprednisolone, 1 gram per day, and her symptoms resolved to normal neurological function within three weeks. She was referred to the Weill Cornell MS Center for confirmation of diagnosis and treatment planning. Repeat neuroimaging at Weill Cornell revealed lesions characteristic in morphology and location for Multiple Sclerosis (FIG. 3). Approximately three months after onset of symptoms, she was enrolled in the HITMS (Harboring the Initial Trigger of Multiple Sclerosis) study, IRB protocol no. 1003010940, and a self-collected stool sample was obtained. Disease modifying treatment was initiated. Eight months after initiation of treatment she remained asymptomatic and her first treatment assessment MRI was performed which revealed several new contrast enhancing lesions (FIG. 3).

Figure 4:
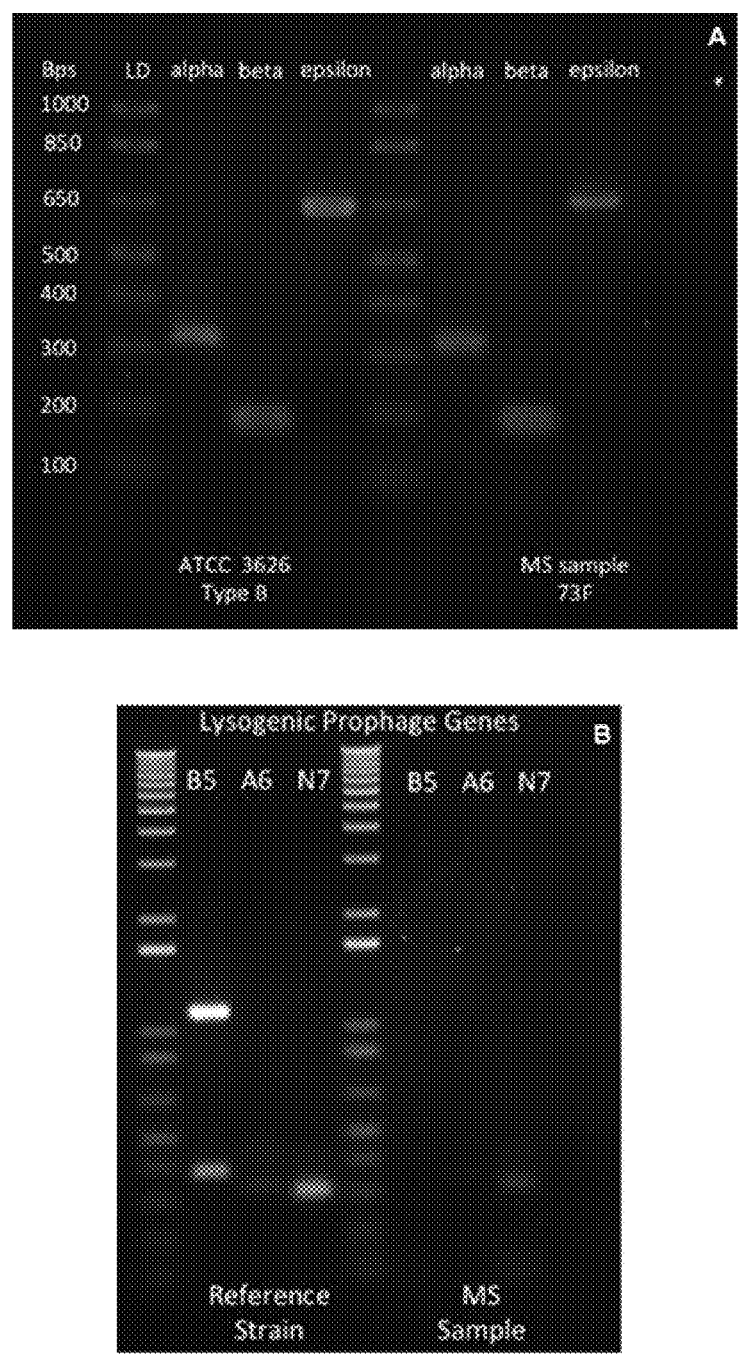
FIG. 4. *C. perfringens* type B in a woman with relapsing-remitting MS (RRMS), and the prevalence of *C. perfringens* type A in MS and healthy controls. (4A) Left panel shows PCR based genotyping of ATCC 3626 type B strain and from patient 73F. PCR products for α, β, and ε toxin are identified in both. (4B) To exclude the possibility that the type B strain identified in the stool of patient 73F was a contaminant, the profile of lysogenic prophage genes was determined in the laboratory strain and in the patient isolate (right panel). ATCC 3626 reference strain possesses all three prophage insertions, whereas the patient's strain possesses only the A6 (weakly) and N7 prophage insertions. Phage genes and PCR product size: B1RBB5, 1000 bps; B1RAA6, 300 bps; Q8SBN7, 300 bps.

Three months after onset of her first symptoms, patient 73F was found to harbor *C. perfringens* type B in her GI tract. PCR analysis revealed carriage of genes encoding $\alpha$, $\beta$, and $\epsilon$ toxins (FIG. 4A). This represents the first human known to carry type B and the first MS patient found to carry an ETX producing *C. perfringens*. To exclude a possible laboratory-derived contaminant, a lysogenic bacteriophage footprint analysis was performed of the laboratory (ATCC 3626) and patient-derived *C. perfringens* strains. Three lysogenic bacteriophage insertions were identified in the laboratory strain, which matched the known whole genome sequence (FIG. 4B). The patient's strain contained just two lysogenic bacteriophage insertions, thus confirming that the patient-derived ETX amplicon was not a laboratory contaminant (FIG. 4B). Since a combination of toxinotypes C and D would also result in identification of $\alpha$, $\beta$, and $\epsilon$ toxin genes, the patient-derived ETX gene was sequenced confirming that it was derived from a type B ETX plasmid[9]. Interestingly, eight months after detection of *C. perfringens* type B in patient 73F, repeat analysis showed her to be negative, highlighting the dynamic nature of *C. perfringens* type B colonization.

Example 5

Specificity of *C. perfringens* Epsilon Toxin for White Matter, Oligodendrocytes, and Meninges in the CNS ETX binding to CNS vasculature and white matter has been previously reported[15-17]. However, these studies both lack relevant controls to prove that ETX binding to these structures was specific and report findings that markedly teach away from a pathophysiology whereby ETX could cause MS. These studies only showed ETX binding to white matter and did not show binding to the myelin forming cell of the CNS, the oligodendrocyte. Further, these studies do not teach or suggest a relationship between ETX and MS. First, these studies showed binding of ETX to cerebellar neurons, a finding that teaches away from ETX being an environmental agent responsible for MS lesion formation since cerebellar neurons are not cellular targets in MS. Second, these studies report that ETX binds both myelin of the CNS and PNS.

Using the MAL loss-of-function mutant mouse, the invention shows that all ETX binding to CNS vasculature and to white matter is abolished thus providing unequovical proof that these neuroanatomic sites are specific targets of the toxin. The invention further provides clear evidence that epsilon toxin neither binds to nor kills cerebellar neurons (see e.g., FIGS. 18a-18d below), and that ETX does not kill neurons supporting its specificity in MS nascent lesion formation. The invention further confirms that this finding of ETX binding to the CNS myelin and the peripheral nervous system (PNS) myelin is true. However, MS is defined as a disease characterized specifically by involvement of CNS but not PNS myelin. An agent that targets both CNS and PNS myelin unquestionably teaches away from any relationship to MS.

The pathophysiologic mechanism for ETX mediated demyelination involves (but is not limited to) the following key steps: toxin production in the GI tract or other body habitat; toxin activation by proteases in the gut or other body habitats; entry of ETX into the blood/intravascular compartment from the gut or other body habitat; binding of ETX to the apical (luminal) surface of CNS but not other but not other endothelial cells; entry of ETX into the CNS parynchyma where it binds to and injures/kills oligodendrocytes leading to demyelination. Since ETX does not bind to endothelial cells of the PNS, ETX can not enter the PNS compartment and thus even though PNS myelin binds ETX, the toxin never encounters PNS myelin because it can not enter leave the intravascular compartment of the PNS. This remarkable specificity of Multiple Sclerosis affecting CNS but not PNS myelin is so characteristic of the disease that binding of epsilon to PNS myelin all but excluded epsilon as a possible cause of the disease. One rational explanation is that epsilon binds to the apical surface of CNS but not PNS endothelial cells and that the blood nerve barrier, unlike the blood-brain and blood-retina barriers, is insensitive to epsilon.

Figure 12:
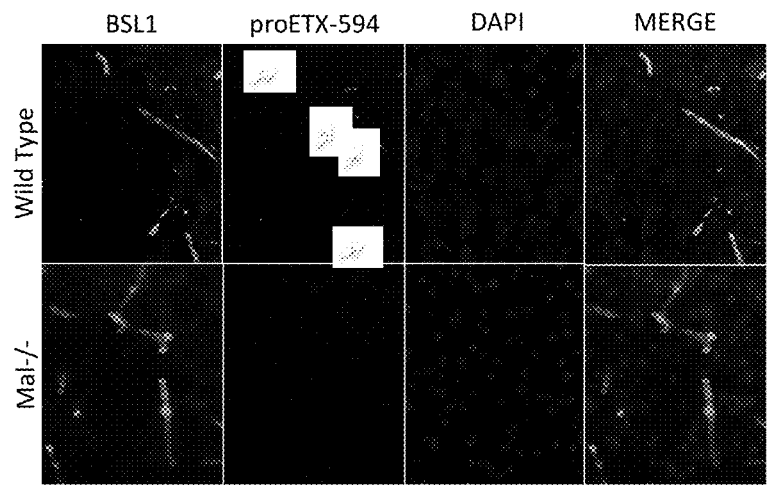
FIG. 12. ETX specifically binds to the luminal (apical) surface of CNS endothelial cells. Wild-type mice (n=4) and MAL KO mice (n=3) were administered Alexa594 conjugated pro-ε-toxin (red) via tail vein injection, followed by a tail vein injection of Alexa488 conjugated BSL1 (green). After ten minuets, anesthetized animals were perfused with PBS then sacrificed. 12 micron frozen sections of the brain were examined for coincidence of BSL1 and pro-ε-toxin staining. Microvasculature within the brain revealed coincident labeling of pro-ε-toxin with BSL1. Most but not all segments of BSL1 positive vessels were pro-ε-toxin positive raising the question of heterogeneity of ε-toxin receptor expression versus kinetics of binding. Importantly, MAL KO mice show no binding of pro-ε-toxin binding to microvasculature in the brain both demonstrating the specificity of binding in wild-type animals and requirement for MAL. ETX=ε-toxin.

Thus, once in the blood stream, ETX makes its way to the CNS and initiates the process of blood-brain barrier disruption by first binding to CNS endothelial cells and second disrupting physiologic barrier function due to reversible and/or irreversible endothelial cell injury. Experiments show that ETX binds to the luminal surface of brain endothelial cells and in conjunction with the published literature this provides compelling evidence in support that ETX targets the blood brain barrier. Fluorescently tagged proETX was injected into the tail vein of mice and following perfusion with PBS, histologic sections were examined within brain to assess luminal binding of ETX. Within the brain unequivocal robust binding of ETX to the apical (luminal) surface of endothelial cells was observed (FIG. 12). Binding of ETX to CNS microvasculature requires MAL as MAL KO mice fail to show ETX binding (FIG. 12). The fact that MAL KO mice fail to show any ETX binding to microvasculature confirms the specificity of ETX binding in wild-type animals and provides evidence that MAL is the ETX receptor.

Figure 5:
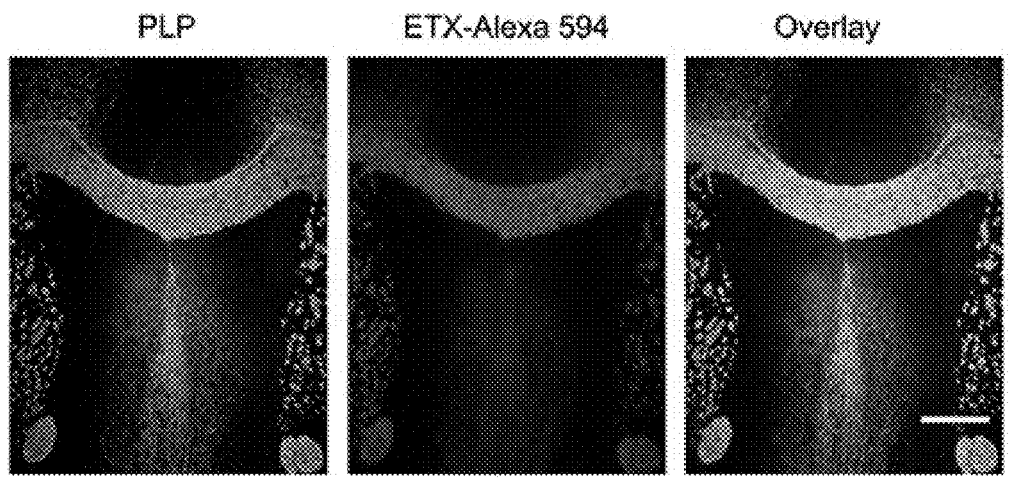
FIG. 5. ETX binds specifically to myelin. Fixed frozen coronal sections from adult mouse brain through the corpus callosum were stained for proteolipid protein (PLP, green), and Alexa 594-ETX (red). Intense staining with ETX is observed in all PLP-positive white matter tracts. Merged PLP and ETX images reveal essentially complete overlapping fluorescent signal. Bar=500 μm.

To verify that ETX binding in the CNS localizes to myelin, fluorescently labeled ETX was developed to stain mouse brain cryosections. Myelin was identified by immunoreactivity against the proteolipid protein (PLP). ETX binding in the mouse CNS showed essentially complete overlap with CNS myelin (FIGS. 5 and 24). Taken together with prior published reports of ETX binding to brain vasculature and disruption of the BBB, binding of ETX to white matter presents a clear mechanistic link between ETX, BBB disruption and oligodendrocyte/myelin injury. To prove that ETX binding was specific to oligodendrocytes, primary cell cultures were generated from mouse or rat CNS (see e.g., FIGS. 11A-11F below). In mixed cultures, it was found ETX binding to cells in the oligodendrocyte lineage but not to astrocytes or microglia (see e.g., FIG. 17, FIGS. 19A-19B, and FIGS. 23A-23C) but not to astrocytes or microglia (see e.g., FIGS. 21A-21B and FIGS. 22A-22B).

In addition ETX staining of CNS meninges and microvasculature within the meninges were identified. The significance of meningeal binding of epsilon toxin is that focal meningeal inflammation is known to occur in MS, but the mechanism initiating this process is unknown. This work provides a unique and clear mechanism for meningeal inflammation whereby ETX within the blood binds to meningeal vessels; endothelial injury ensues leading to extravisation of ETX into the meningeal tissue; ETX binds to and injures/kills meningeal cells; injured meningeal cells release well described danger associated molecular patterns (DAMPS) leading to a secondary inflammatory response through activation of a host of pattern recognition receptors. In addition ETX leak through the meningeal vessels provides a mechanism for subpial cortical MS lesions that have defied prior mechanistic explanation.

Figure 16:
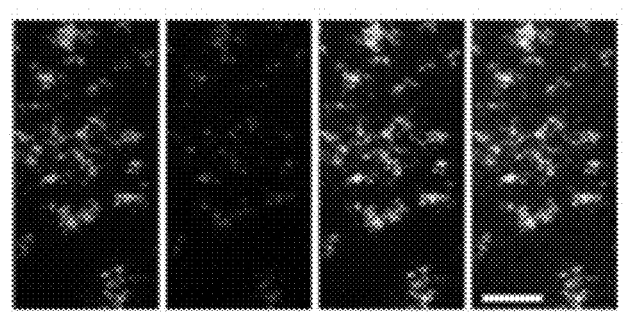
FIG. 16. Inactive pro-ETX-Alexa 594 conjugate selectively binds to MBP-positive cells on cerebellar slices. Cerebellar slice cultures were stained with flourescently conjugated ETX and for MBP. A randomly chosen field with low MBP-immunostaining (green) density shows that pro-ETX (red) colocalizes with MBP-positive cells/structures, indicating ETX selectively binds MBP-producing mature oligodendrocytes. The majority of cells (identified by DAPI counterstain, blue) are negative for both MBP immunostaining and pro-ETX binding. Note that pro-ETX labeling does not completely overlap with MBP immunostaining, suggesting ETX targets subcellular sites that are different, at least partially, from the sites of MBP expression. Scale bar represents 100 µm.
Figure 17:
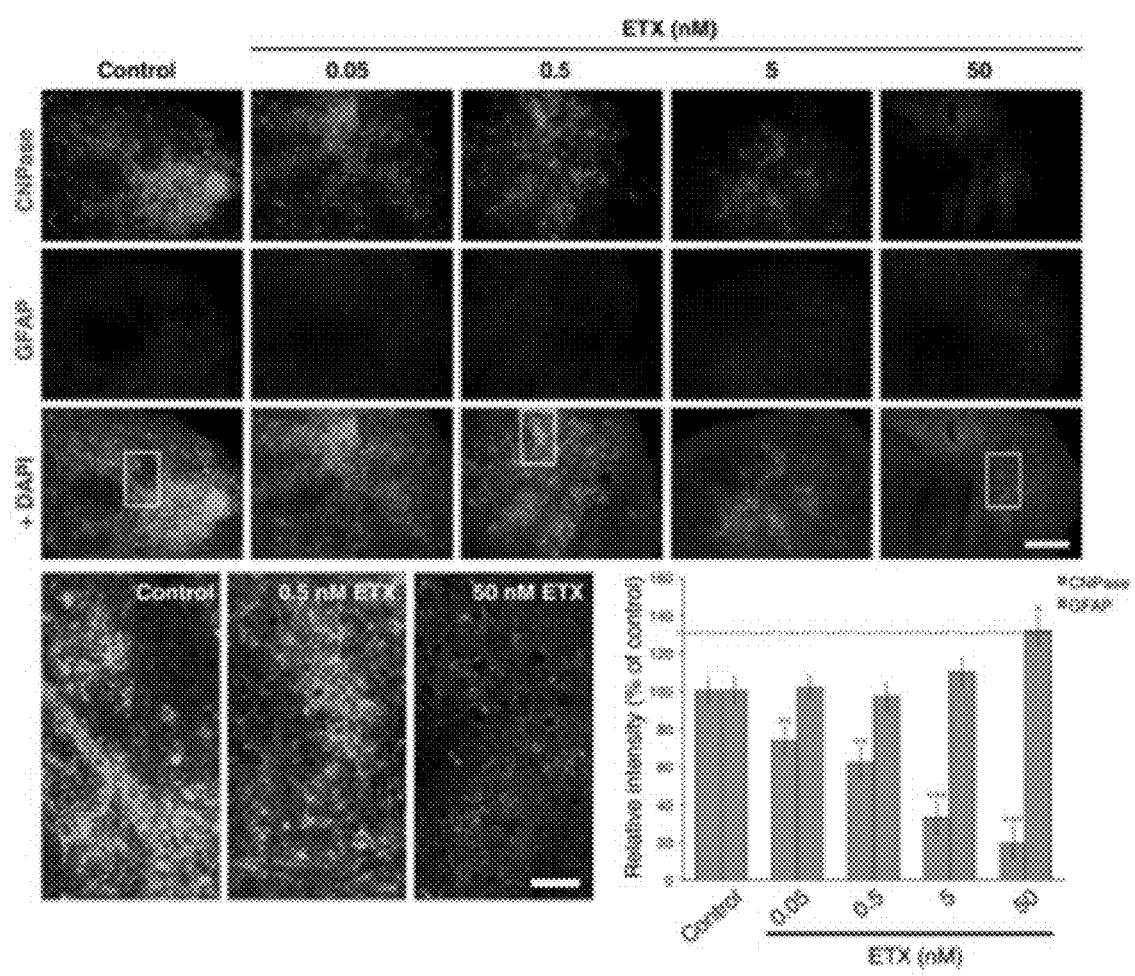
FIG. 17. GFAP expression is modestly upregulated in cerebellar slices exposed to higher doses of ETX stimulation, as a secondary response to ETX-induced effect on oligodendrocytes. Top rows provide representative images and bottom right panel provides quantitation of immunostaining against CNPase (oligodendrocyte marker, green) and GFAP (astrocyte marker, red) on slices exposed to PBS (vehicle control) or ETX at indicated doses for 20 hours. DAPI (blue) is counterstained to identify cell nuclei. Regions framed in low-magnification images (third row) are shown in higher magnification (bottom left panels) to illustrate immunostaining details in respective conditions. Quantitation on CNPase and GFAP immunofluorescence intensity indicates concentration-dependent decrease of CNPase in response to ETX, contrasting to GFAP increase only in higher concentration (50 nM). n=6-8 slices for each condition, normalized to respective controls (100%); *p<0.05, p<0.01, * p<0.001, two-tailed t-test. Similar results were obtained in two independent experiments. Scale bars represent 500 µm in low magnification (rows 1-3) and 100 µm in high magnification (bottom left panels).
Figure 19:
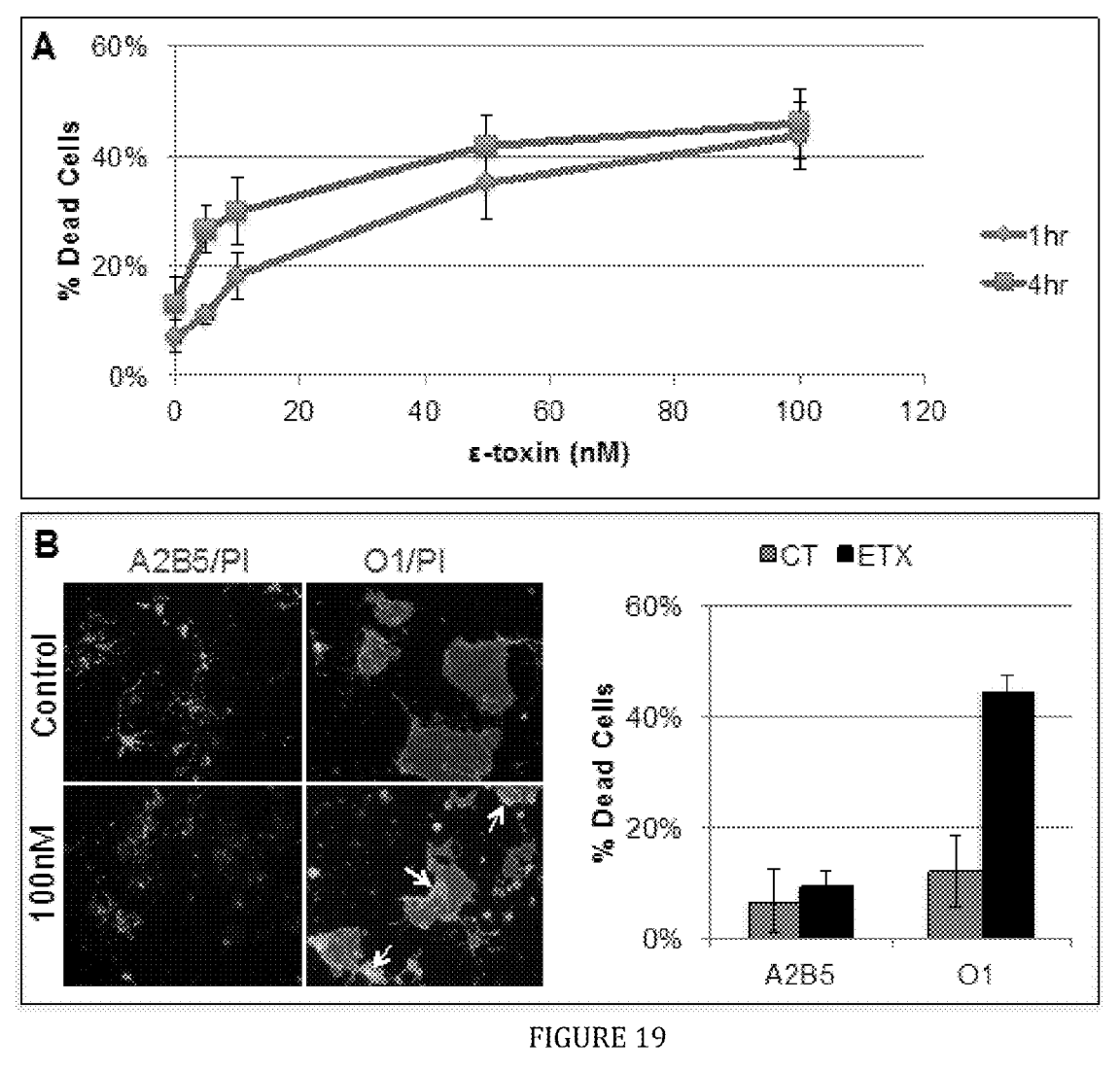
Figure 20:
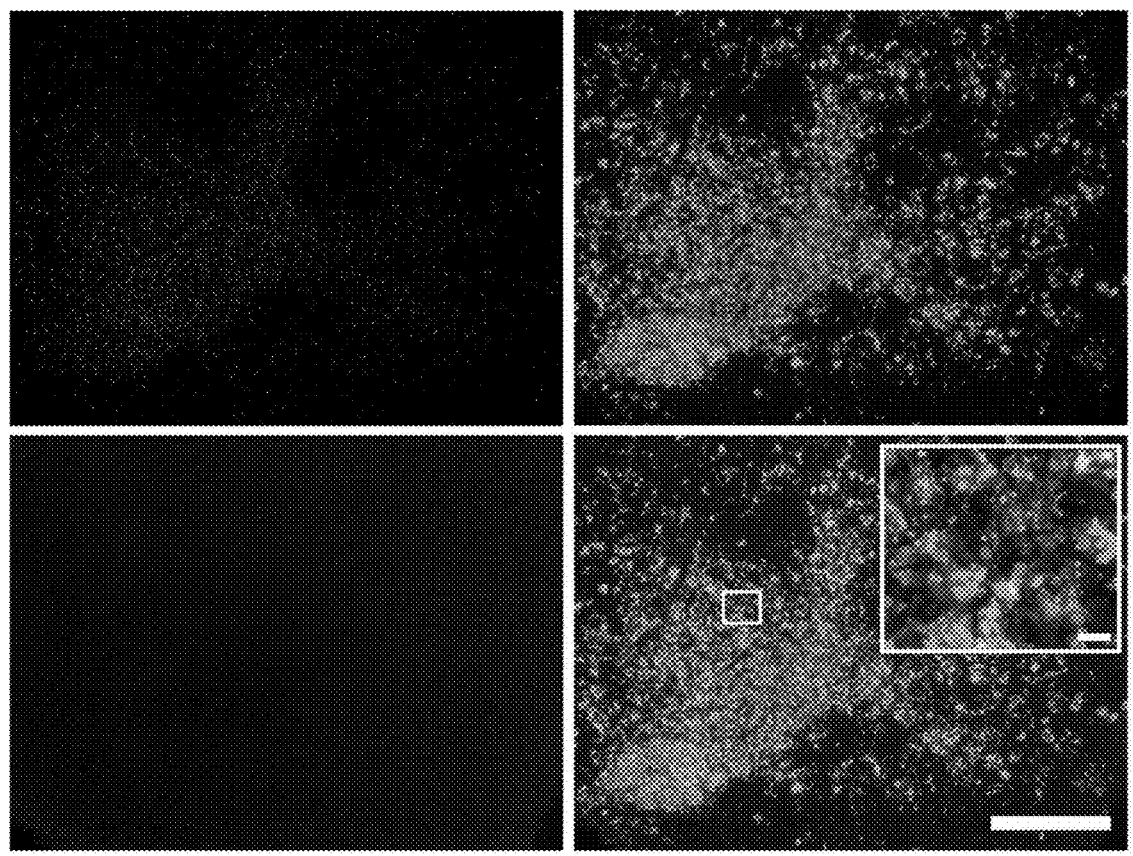
FIG. 20. Olig2-positive cells in cerebellar slices are MBP positive. Cerebellar slices were double labeled with antibodies specific to olig2 (red) and MBP (green). As shown in the micrographs, the vast majority of olig2 positive cells are also MBP positive.

To determine what cells ε-toxin specifically binds to in CNS, mixed glial cells were grown in media to promote oligodendrocyte maturation and probed with Alexaflour-594 conjugated protoxin (proETX-594). No difference has been observed between protoxin and active ε-toxin binding[27]. Binding to specific glial populations was determined by colocalization of ε-toxin and cell specific markers (see e.g., FIGS. 11A-11F; FIG. 16; FIG. 17, and FIGS. 19A-19B to FIGS. 23A-23C). ε-toxin did not colocalize with the astrocyte markers GFAP or the microglial marker CD68 (see e.g., FIGS. 11A and 11B; FIG. 17; and FIGS. 21A; 22A; and 23A). Bound ε-toxin could be seen surrounding some Olig2 positive cells and colocalized with the oligodendrocyte markers MAG, MBP, and PLP (see e.g., FIGS. 11C-11F; FIG. 20). This suggests that ε-toxin binds only to cells of the oligodendrocyte lineage in mixed primary culture.

Because ε-toxin was only observed binding to oligodendrocytes, it was determined if ε-toxin could kill oligodendrocytes in mixed glial culture. Live cells were stained with an O1 antibody to identify oligodendrocytes and treated with active ε-toxin for 1 and 4 hours (see e.g., FIGS. 19A-19B). Cell viability was evaluated by promidium iodine (PI) inclusion. ε-toxin treatment significantly increased the percentage of dead, O1+ cells when compared to untreated controls. After 1 hour of treatment, 18.1%, 35.1%, 41.8% and 45.7% of O1+ cells were dead when treated with 10 nM, 50 nM, and 100 nM of ε-toxin, respectively. Untreated controls only exhibited 7.0% dead cells. Increasing treatment time from 1 hour to 4 hours also significantly increased the percentage of dead O1+ cells for 5 nM and 10 nM ε-toxin treatments; 11.1% to 26.5% and 18.1% to 29.9%, respectively. ε-toxin dependent oligodendrocyte cell death is dose and time dependent.

To ensure that ε-toxin specifically kills oligodendrocytes, enriched cultures of astrocytes, microglia, and oligodendrocytes were treated with ε-toxin. Enriched astrocyte cultures are primarily GFAP positive with some contaminating CD68 positive microglial cells and oligodendrocyte debris (see e.g., FIGS. 21A-21B; 22A-22B; and 23A-23C). Enriched astrocytes were treated with 5 nM, 10 nM, and 50 nM ε-toxin for 24 hours and cell viability evaluated by PI staining. No difference was observed between the untreated controls and ε-toxin treated astrocytes (see e.g., FIGS. 21A-21B; 22A-22B; and 23A-23C). Enriched microglia cultures exhibited similar results (see e.g., FIGS. 21A-21B). Enriched cultures were primarily CD68 positive (see e.g., FIGS. 22A-22B) and exhibited no significant increase in cell death after 24 hours of ε-toxin treatment compared to untreated controls (see e.g., FIGS. 21A, 22A, and 23A). To obtain enriched oligodendrocyte cultures, OPC were isolated from mixed cultures and grown in oligodendrocyte differentiation media. Enriched oligodendrocyte cultures were primarily MPB positive with a few GFAP and CD68 positive contaminating cells (see e.g., FIGS. 21A, 22A, and 23A and 23B). The majority of MBP positive cells also bound proETX-594 (see FIG. 23B). Live enriched oligodendrocyte cultures were stained with O1 and treated with 50 nM ϵ-toxin for 1 and 6 hours. Cell death was evaluated by PI staining. After 1 hour of treatment, ϵ-toxin significantly increased the percentage of PI positive O1 cells compared to untreated controls, 48.2% versus 25.9%, respectively (see FIG. 23C). After 6 hours of ϵ-toxin treatment, 58% of O1+ cells were PI positive compared to only 25.6% for the positive controls (see FIG. 23C). Taken together, this indicates that ϵ-toxin specifically and rapidly kills oligodendrocytes, and ϵ-toxin mediated cell death is dependent on oligodendrocyte maturation.

Although the newly forming MS lesion is characterized by oligodendrocyte cell death, OPC do not appear to be harmed. To determine if ϵ-toxin binds to OPC, mixed primary glia cell cultures were stained for OPC markers and probed with ϵ-toxin. No colocalization of ϵ-toxin and the OPC marker PDGFR were observed in vitro, although robust colocalzation of proETX-594 and the mature oligodendrocyte marker O1 was observed (see e.g., FIGS. 23B and 23C). These results were confirmed using immunohistochemistry (IHC) of tissue sections from postnatal day 17 (p17) pups. Although there was robust colocalization of MPB and ϵ-toxin (see e.g., FIGS. 11E; 14a-14b; 16; 20; 21A, 22A and 23B), there is a complete lack of colocalization of ϵ-toxin and the OPC marker NG2 (see e.g., FIGS. 22A and 23A), indicating that ϵ-toxin only binds to mature oligodendrocytes.

More specifically, FIGS. 11A-11F illustrate that ϵ-Toxin specifically binds to oligodendrocytes in the CNS. Mixed murine glial cells were harvested from p0-6 pups and cultured for 10 days in media promoting oligodendrocyte differentiation. Cells were fixed in 4% PFA and stained with antibodies specific for different glial populations including GFAP for astrocytes (A), CD68 for microglial (B), Olig2 for all oligodendrocyte lineages (C), and MAG (D), MPB (E), and PLP (F) for mature oligodendrocytes. To determine specificity of e-toxin binding, cells were probed with Alexaflour 598 conjugated ϵ-protoxin (proETX). Nuclei were visualized with DAPI.

To demonstrate that ETX specifically targets oligodendrocytes in the CNS, mixed glial cultures were probed with flourescently tagged pro-ETX. Mixed glial cultures contain oligodendrocytes, oligodendrocyte progenitor cells, astrocytes, microglia, menengial cells, and scarce other cell types. It was found the fluorescently tagged pro-ETX labeled only oligodendrocytes thus showing its specificity for this cell type. Mixed murine glial cells were harvested from p0-6 pups and cultured for 10 days in media promoting oligodendrocyte differentiation. Cells were fixed in 4% PFA and stained with antibodies specific for different glial populations including GFAP for astrocytes (FIG. 11A), CD68 for microglial (FIG. 11B), Olig2 for all oligodendrocyte lineages (FIG. 11C), and MAG (FIG. 11D), MPB (FIG. 11E), and PLP (FIG. 11F) for mature oligodendrocytes. To determine specificity of ϵ-toxin binding, cells were probed with Alexaflour 598 conjugated ϵ-protoxin (proETX). Nuclei were visualized with DAPI.

FIG. 12 illustrates that ETX specifically binds to the luminal surface of CNS endothelial cells. The absence of ETX labeling in MAL KO mice substantiates the specificity of the interaction between ETX and wild-type endothelial cells. Binding of ETX to CNS endothlial cells provides a mechanism for ETX entry into the CNS to target oligodendrocytes and myelin.

Figure 14:
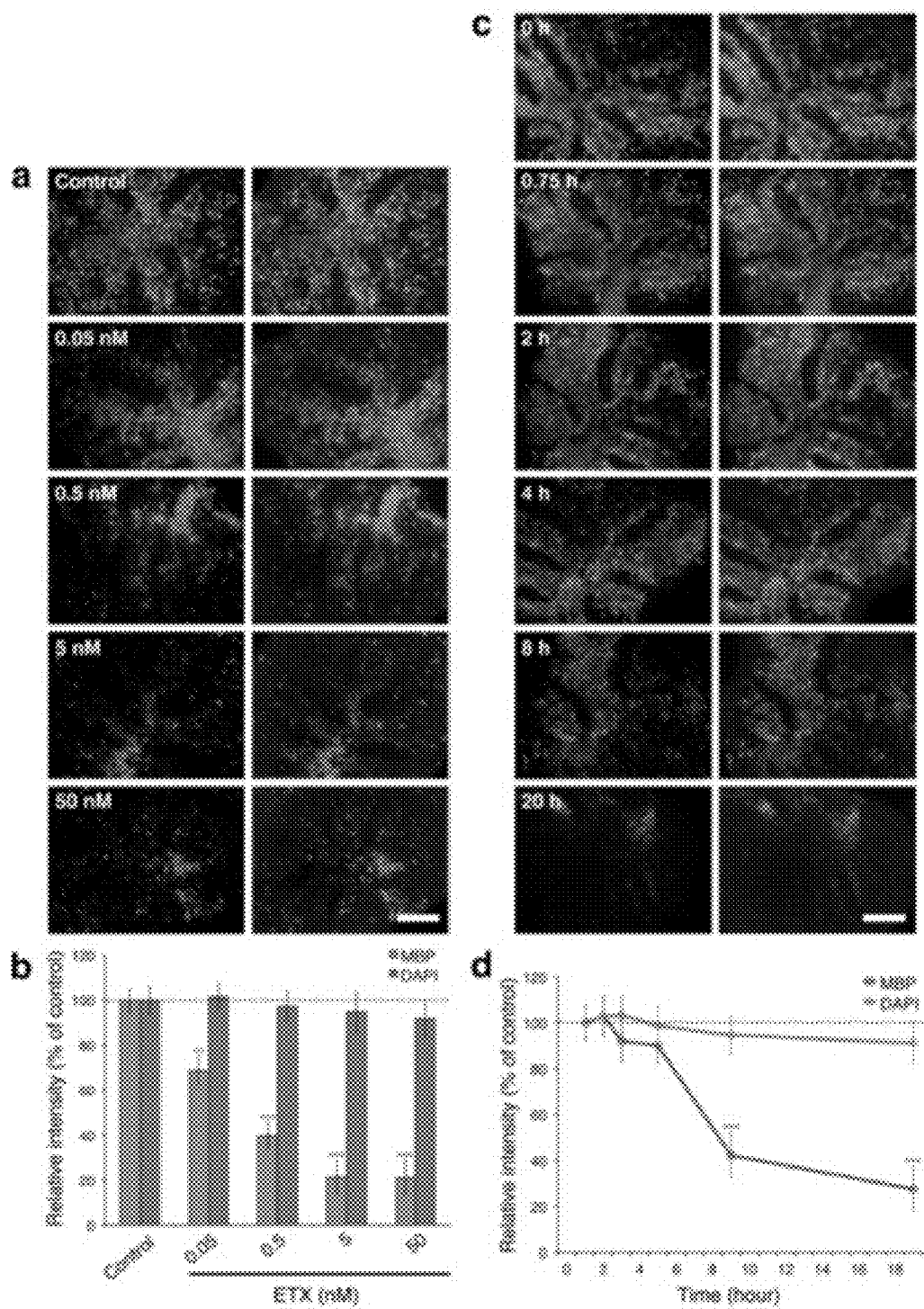
FIG. 14. ETX exposure leads to concentration and time-dependent reduction of MBP expression in cerebellar slice culture. 14A and 14B provide representative images (14A) and quantitation (14B) of MBP-immunostaining (green) with slices exposed to PBS (vehicle control) or ETX at indicated doses for 20 hours. 14C and 14D provide representative images (14C) and quantitation (14D) of MBP-immunostaining (green) with slices treated with 5 nM ETX at indicated time points. DAPI (blue) is counterstained to identify nuclei of all cells. Quantitation of MBP immunofluorescence intensity against that of DAPI (14B, 14D) shows that ETX does not affect overall cell survival but instead impinges on MBP-expressing cells. n=6-8 (14A, 14B) and 5-6 (14C, 14D) slices for each condition, normalized to respective controls (100%); p<0.01, * p<0.001, two-tailed t-test. Note that slices in (14A, 14B) and (14C, 14D) were from independent preparations. Similar results were obtained in at least three independent experiments. Scale bars represent 500 µm.

FIGS. 14A-14D provide that ETX exposure leads to concentration- and time-dependent reduction of MBP expression in cerebellar slice culture. To determine if ETX induced demyelination in dose and time dependent manner, fully myelinated organotypic cerebellar slice cultures were treated with escalating doses of ETX or with a single concentration of ETX for increasing times. In both instances there is a clear concentration and time dependent effect of ETX on inducing demyelination. Myelin content was assessed by MPB immunofluorescence using Image J for quantification. FIGS. 14A and 14B provide representative images (a) and quantitation (b) of MBP-immunostaining (green) with slices exposed to PBS (vehicle control) or ETX at indicated doses for 20 hours. FIGS. 14C and 14D provide representative images (c) and quantitation (d) of MBP-immunostaining (green) with slices treated with 5 nM ETX at indicated time points. DAPI (blue) is counterstained to identify nuclei of all cells. Quantitation of MBP immunofluorescence intensity against that of DAPI (b, d) shows that ETX does not affect overall cell survival but instead impinges on MBP-expressing cells. Similar results were obtained in at least three independent experiments. Scale bars represent 500 μm.

Figure 15:
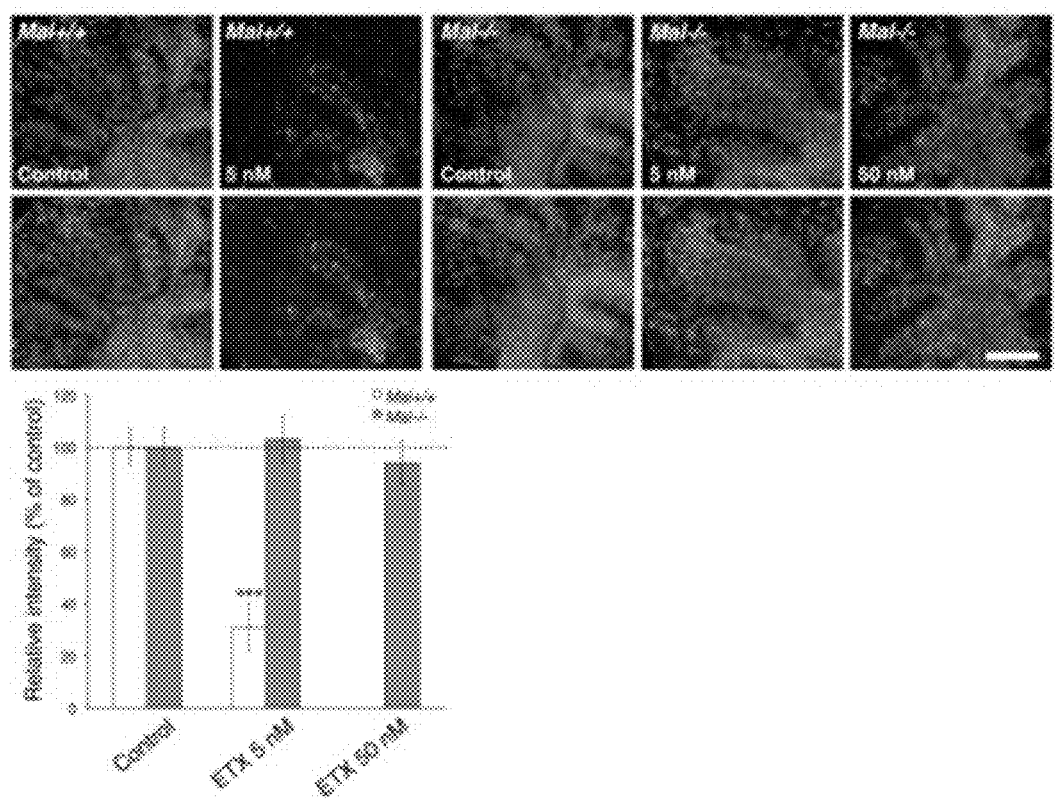
FIG. 15. MAL deletion renders cerebellar slices resistant to ETX-induced MBP reduction. Top rows provide representative images and bottom row provides quantitation of MBP-immunostaining (green) with slices prepared from wild-type (Mal+/+) and Mal-deleted (Mal−/−) mice. Slices were exposed to either PBS (vehicle control) or ETX at indicated doses for 20 hours. DAPI (blue) was counterstained to identify cell nuclei. n=5-6 slices for each condition, normalized to respective controls (100%); *** p<0.001, two-tailed t-test. Similar results were obtained in three independent experiments. Scale bar represents 500 µm.

FIG. 15 illustrates that MAL deletion renders cerebellar slices resistant to ETX-induced MBP reduction. To determine if MAL is required for the effects of ETX on inducing demyelination, fully myelinated cerebrellar slices were generated from wild-type (Mal+/+) and MAL KO (Mal−/−) mice. While wild-type mice show near complete demyelination with ETX treatment, MAL KO mice were in contrast completely resistant to the effects of ETX. These results support two important discoveries. First, MAL is required for the effects of ETX; and second, ETX is highly specific toxin that does not cause non-specific cell injury even at high concentrations.

FIG. 16 illustrates that inactive pro-ETX-Alexa 594 conjugate selectively binds to MBP-positive cells on cerebellar slices. To verify that ETX only binds to oligodendrocytes, cerebellar slice cultures were stained with flourescently conjugated ETX and for MBP. A randomly chosen field with low MBP-immunostaining (green) density shows that pro-ETX (red) colocalizes with MBP-positive cells/structures, indicating ETX selectively binds MBP-producing mature oligodendrocytes. The majority of cells (identified by DAPI counterstain, blue) are negative for both MBP immunostaining and pro-ETX binding. Note that pro-ETX labeling does not completely overlap with MBP immunostaining, suggesting ETX targets subcellular sites that are different, at least partially, from the sites of MBP expression. Scale bar represents 100 μm.

FIG. 17 illustrates that GFAP expression is modestly upregulated in cerebellar slices exposed to higher doses of ETX stimulation, as a secondary response to ETX-induced effect on oligodendrocytes. To verify the specificity of ETX for oligodendrocytes and myelin, representative images (top rows) and quantitation (bottom right panel) of immunostaining against CNPase (oligodendrocyte marker, green) and GFAP (astrocyte marker, red) on slices exposed to PBS (vehicle control) or ETX at indicated doses for 20 hours. DAPI (blue) is counterstained to identify cell nuclei. Regions framed in low-magnification images (third row) are shown in higher magnification (bottom left panels) to illustrate immunostaining details in respective conditions. Quantitation on CNPase and GFAP immunofluorescence intensity indicates concentration-dependent decrease of CNPase in response to ETX, contrasting to GFAP increase only in higher concentration (50 nM). This suggests astrocytes is not directly involved in mediating the effect of ETX on oligodendrocytes.

Figure 18:
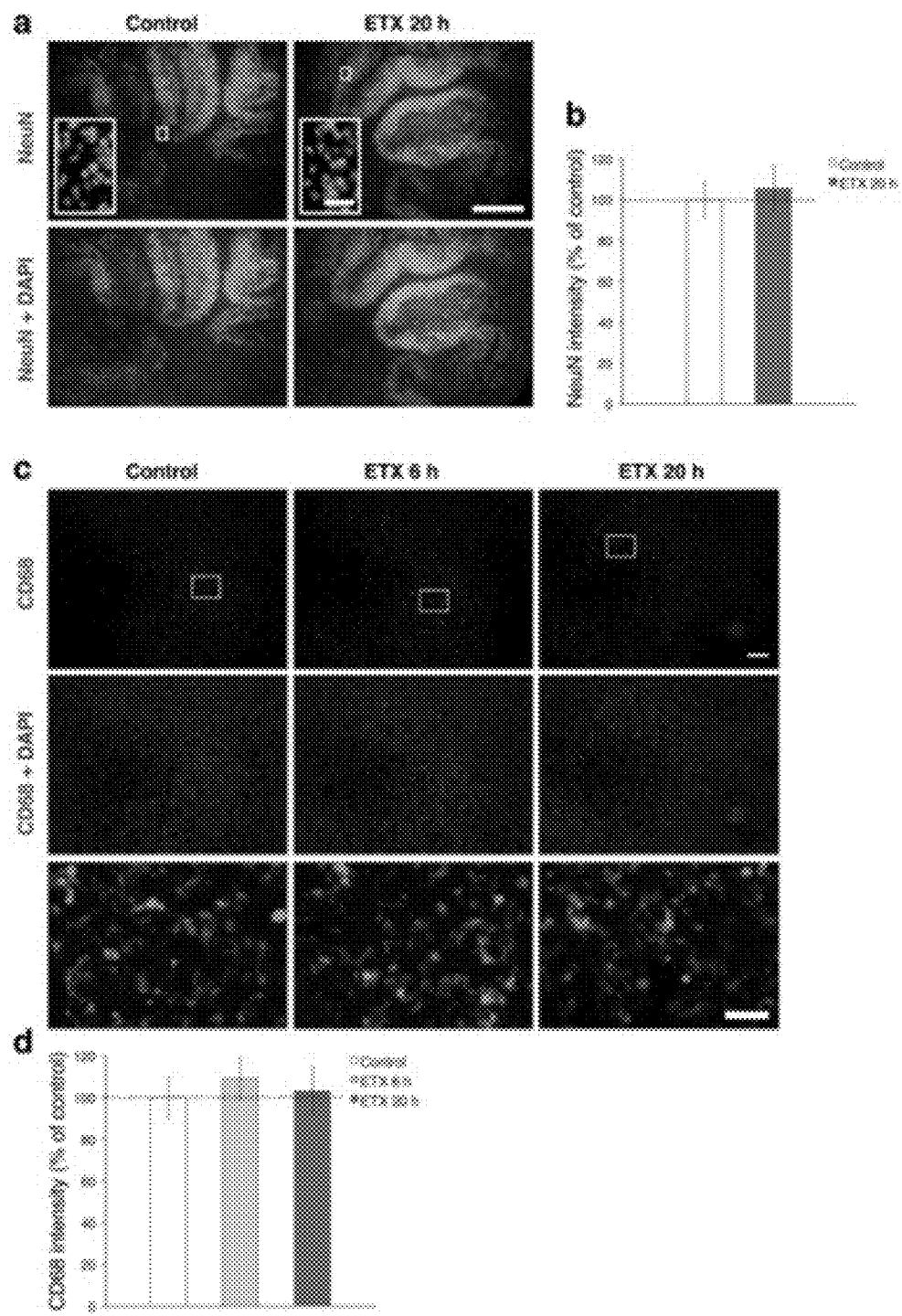
FIG. 18. ETX exposure has no effect on neurons and microglia in cerebellar slices. 18A and 18B provide representative images (left panels) and quantitation (right panel) of NeuN-immunostaining (green) with slices exposed to PBS (vehicle control) or 10 nM ETX for 20 hours. Inserts (top row) show the regions framed in low-magnification in corresponding conditions at a higher magnification to illustrate nuclear staining pattern of NeuN, a neuronal marker. 18C and 18D provide representative images (top rows) and quantitation (bottom panel) of CD68-immunostaining (green) with slices exposed to PBS (vehicle control) or 5 nM ETX at indicated time points. Bottom row in (18C) shows the regions framed in low-magnification (top row) in corresponding conditions at a higher magnification to illustrate immunostaining patterns of CD68, a microglial marker. DAPI (blue) was counterstained to identify cell nuclei. n=5-6 slices for each condition, normalized to respective controls (100%); two-tailed t-test. Similar results were obtained in two (18A, 18B) or three (18C, 18D) independent experiments. Scale bars represent 500 µm (18A, low magnification), 10 µm (18A, inserts), 500 µm (18C, the first and second rows), and 20 µm (18C, bottom row).

FIGS. 18A-18D demonstrate that ETX exposure has no effect on neurons and microglia in cerebellar slices. To further verify the specificity of ETX for oligodendrocytes and myelin the CNS, the effects of ETX on neurons and microglia were assessed in cerebellar slices. Using Image J to quantify immunofluorescence images, no effect of ETX on neuronal or microglial numbers was observed. FIGS. 18A and 18B provide representative images (left panels) and quantitation (right panel) of NeuN-immunostaining (green) with slices exposed to PBS (vehicle control) or 10 nM ETX for 20 hours. Inserts (top row) show the regions framed in low-magnification in corresponding conditions at a higher magnification to illustrate nuclear staining pattern of NeuN, a neuronal marker. FIGS. 18C and 18D provide representative images (top rows) and quantitation (bottom panel) of CD68-immunostaining (green) with slices exposed to PBS (vehicle control) or 5 nM ETX at indicated time points. Bottom row in (c) shows the regions framed in low-magnification (top row) in corresponding conditions at a higher magnification to illustrate immunostaining patterns of CD68, a microglial marker. DAPI (blue) was counterstained to identify cell nuclei.

FIGS. 19A-19B illustrate that ϵ-toxin kills oligodendrocytes. FIG. 19A shows that mixed primary glia culture grown in media to promote oligodendrocyte maturation were identified by live O1 staining. FIG. 19B provides typical micrographs of live mixed primary glia culture stained with A2B5 and O1 antibodies on left side. Cultures were treated with 100 nM of ϵ-toxin for 4 hours and cell viability was evaluated by PI inclusion. Quantification of the percentage of dead A2B5+ cells and O1+ cells after 1 hour of ϵ-toxin 100 nM treatment are presented on right side.

FIG. 20 illustrates that Olig2-positive cells in cerebellar slices are MBP positive. To demonstrate that the majority of olig2-positive cells in cerebellar slice explants also label for the myelin marker MBP, cerebellar slices were double labeled with antibodies specific to olig2 (red) and MBP (green). As shown in the micrographs, the vast majority of olig2 positive cells are also MBP positive (FIG. 20).

Figure 21:
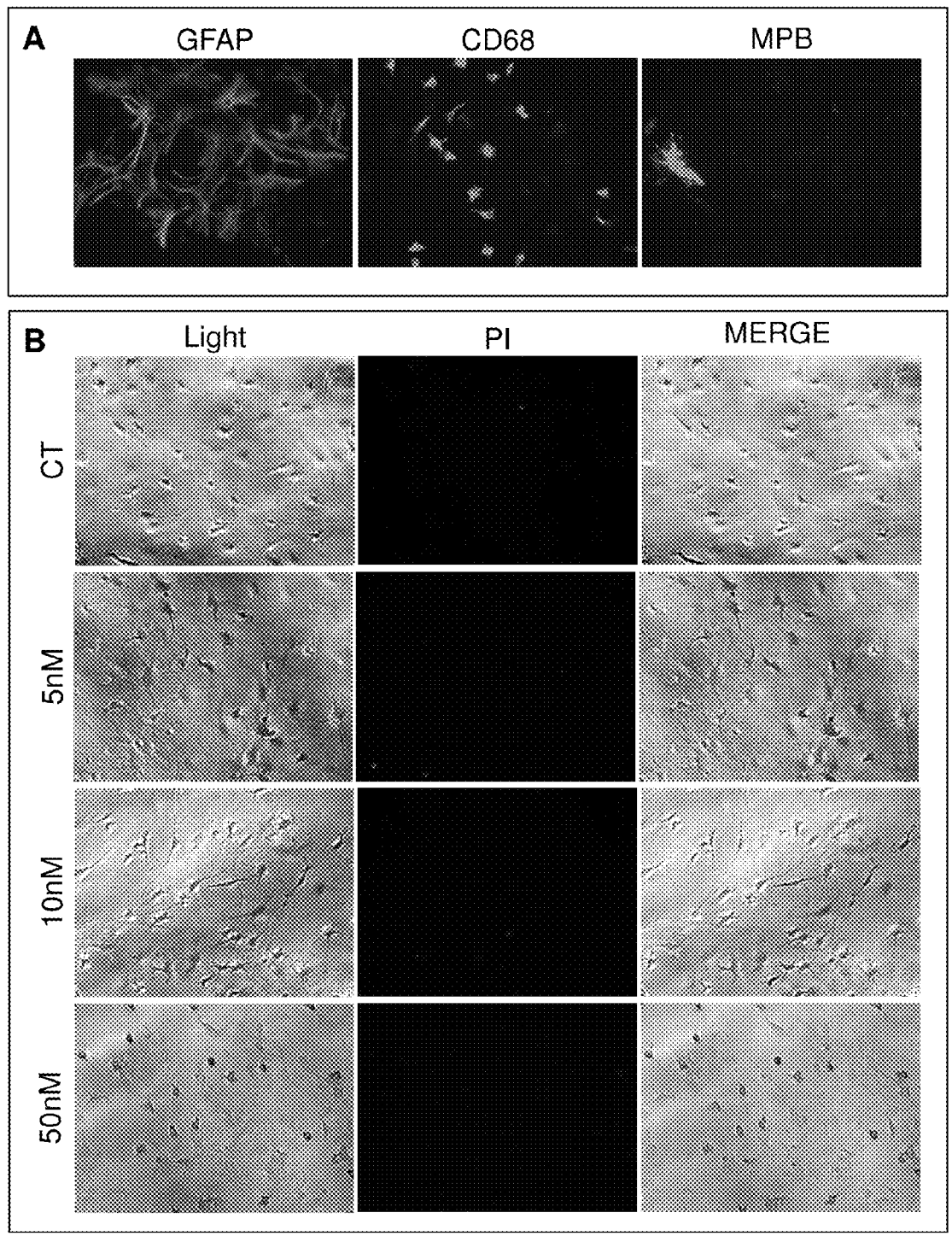
FIG. 21. ε-toxin does not kill enriched astrocytes. Astrocytes were enriched from mixed primary glia cultures. 21A. Purity of cultures was determined by staining fixed cells with antibodies against astrocyte marker GFAP, microglia marker CD68, and oligodendrocyte marker MBP. 21B. Enriched astrocytes were treated with the indicated doses of ε-toxin for 24 hours. Cell viability was evaluated by PI inclusion.

FIGS. 21A-21B illustrate that ϵ-toxin does not kill enriched astrocytes. Microglia cells were enriched from mixed primary glia cultures. FIG. 21A shows that purity of cultures was determined by staining fixed cells with antibodies against astrocyte marker GFAP, microglia marker CD68, and oligodendrocyte marker MBP, and FIG. 21B shows that enriched astrocytes were treated with the indicated doses of ϵ-toxin for 24 hours. Cell viability was evaluated by PI inclusion.

Figure 22:
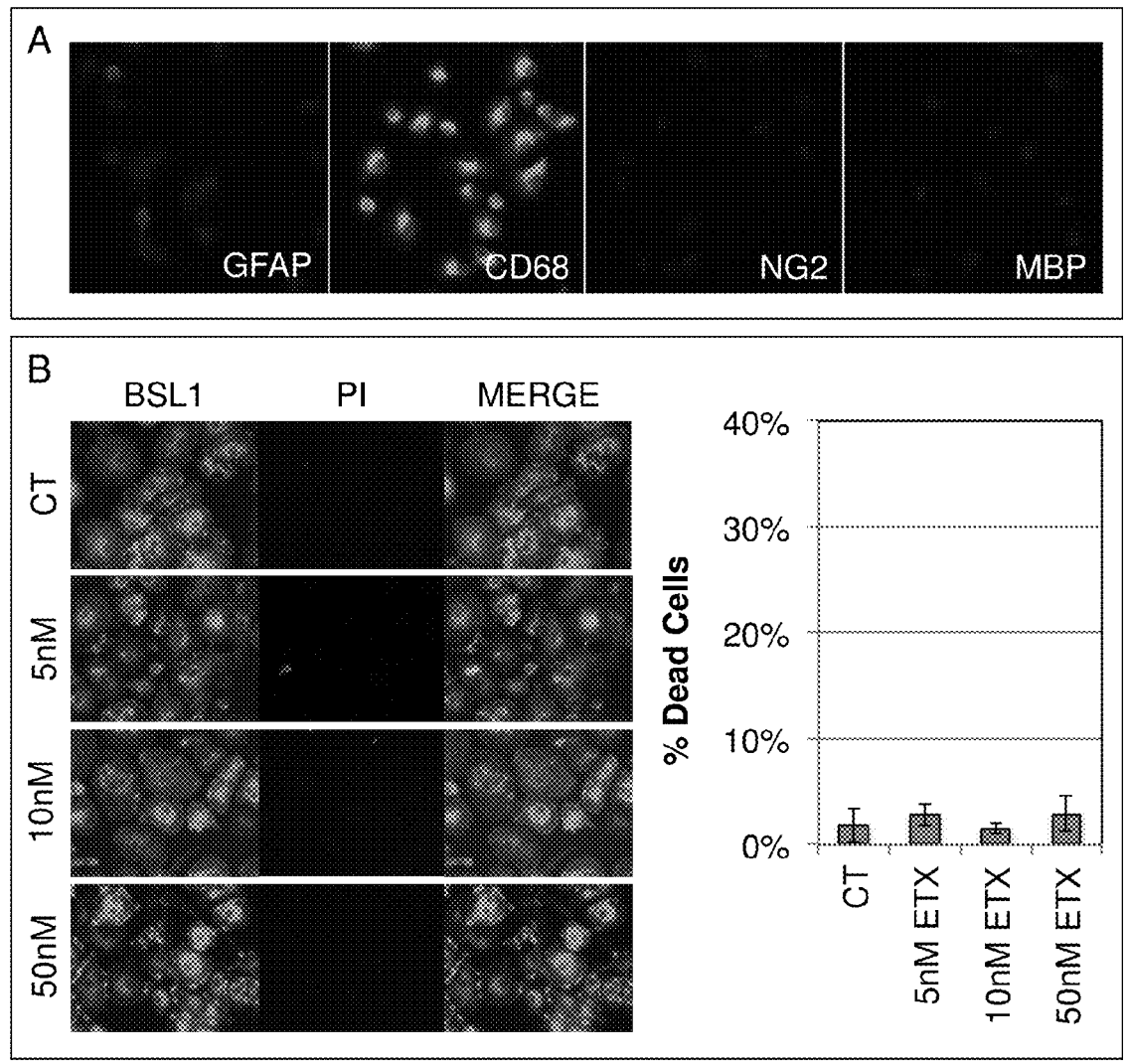
FIG. 22. ε-toxin does not kill enriched microglia cells. Microglia cells were enriched from mixed primary glia cultures. 22A. Purity of cultures was determined by staining fixed cells with antibodies against astrocytes marker GFAP, microglia marker CD68, OPC marker NG2 and oligodendrocyte marker MBP. 22B. Live microglia cells were stained with the fluorescently labeled lectin BSL1 and treated with the indicated ε-toxin doses for 24 hours. Cell death was evaluated by PI inclusion. Typical micrographs after 24 hours of treatment on right side. Quantification of % dead cells on left side. % Dead Cells were calculated by dividing the number of BSL1+ cells that were PI positive by the total number of BSL1+ cells. Results are mean±STDEV.

FIGS. 22A-22B illustrate that ϵ-toxin does not kill enriched microglia cells. Microglia cells were enriched from mixed primary glia cultures. FIG. 22A shows that purity of cultures was determined by staining fixed cells with antibodies against astrocytes marker GFAP, microglia marker CD68, OPC marker NG2 and oligodendrocyte marker MBP, and FIG. 22B shows that live microglia cells were stained with the fluorescently labeled lectin BSL1 and treated with the indicated ϵ-toxin doses for 24 hours. Cell death was evaluated by PI inclusion. Typical micrographs after 24 hours of treatment are presented on the right side.

Figure 23:
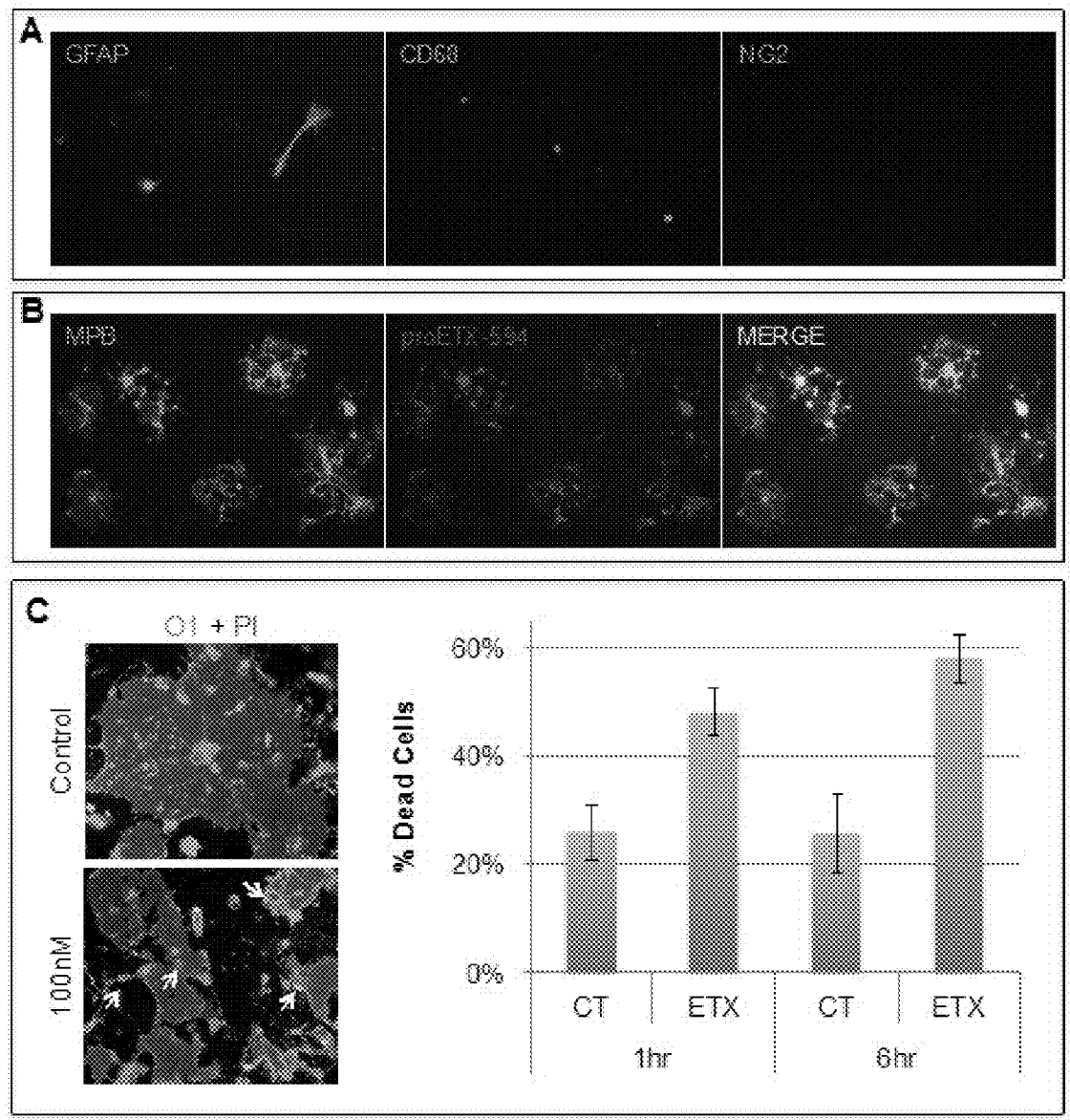
FIG. 23. ε-toxin kills enriched oligodendrocytes. 23A. To evaluate the purity of enriched oligodendrocyte culture, cells were stained with the astrocyte marker GFAP, microglia marker CD6, and OPC marker NG2. 23B. Enriched oligodendrocytes were stained with MBP and proETX-594. 23C. Typical micrograph of oligodendrocyte culture live stained with O1 antibody on right. Cells were treated with 100 nM ε-toxin and cell viability evaluated by PI inclusion. Arrows point to PI positive O1 cells. Quantification of the percent of dead O1 positive cells after ε-toxin treatment for 1 and 6 hours on left side. % Dead Cells was calculated y diving the number of PI positive O1+ cells by the total number of O1 cells. Results are mean±STDEV.
Figure 24:
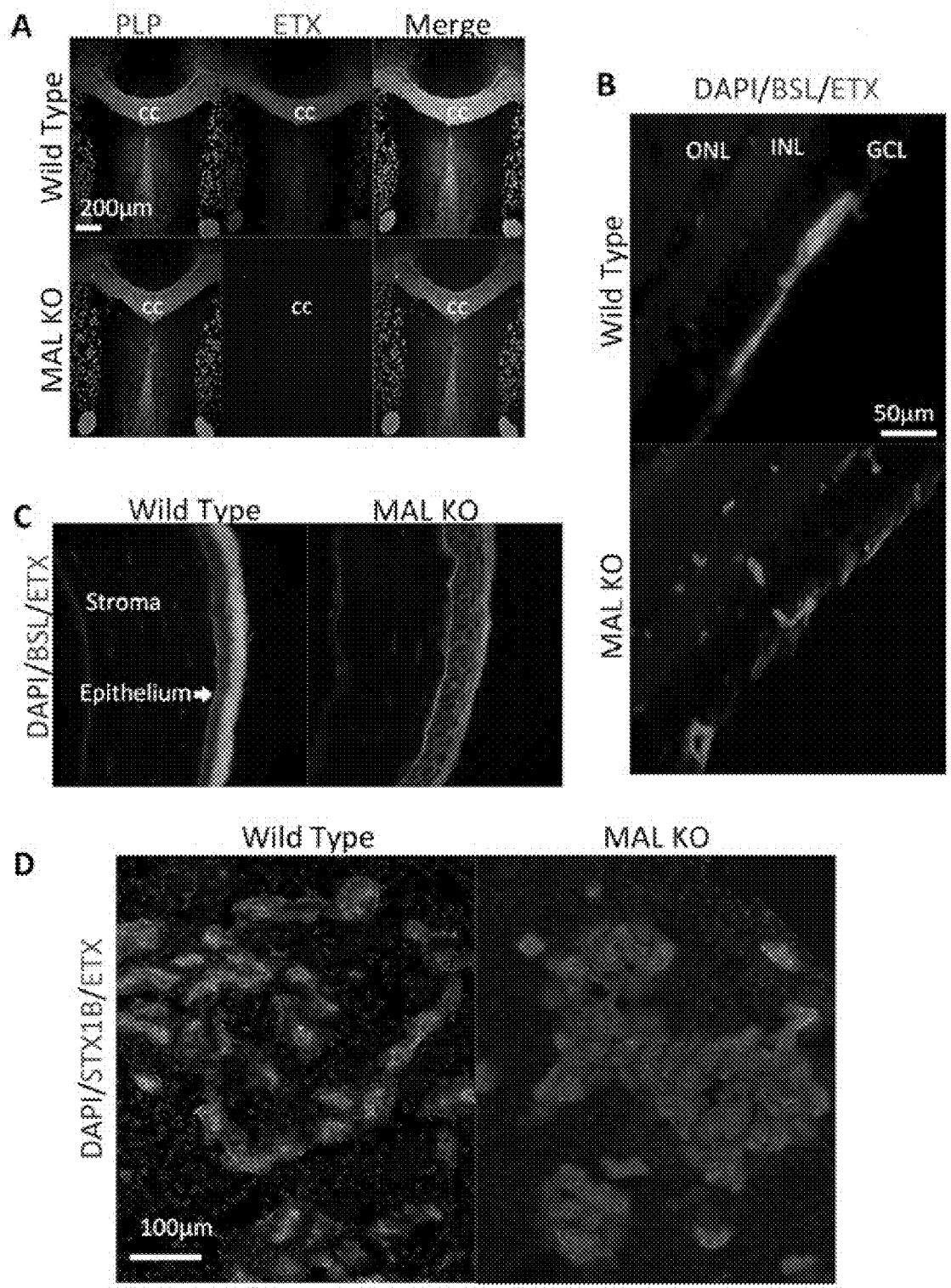
FIG. 24. 24A. MAL is necessary for ε-toxin binding to CNS white matter and CNS endothelial cells. Brain section from a wild type mouse (top panel) stains for PLP (myelin marker) and ε-toxin-594. The merged image shows almost compete overlap. A brain section from a MAL knockout mouse (bottom panel) stains for PLP, but not for ε-toxin-594. 24B. MAL is necessary for ε-toxin binding to retinal vessels. Retinal vessels from a wild type mouse stain positive for BSL (a pan endothelial cell microvasculature marker), ε-toxin-594 and DAPI. Retinal vessels from a MAL knockout mouse stain for BSL and DAPI, but fail to stain for ε-toxin-594. 24C. MAL is necessary for ε-toxin binding to the cornea. Squamous epithelium of the cornea from a wild type mouse stains positive for BSL lectin, ε-toxin-594 and DAPI. Cornea from a MAL knockout mouse stains for BSL lectin and DAPI, but fails to stain for ε-toxin-594. 24D. MAL is necessary for ε-toxin binding to renal tubules. Kidney tissue section from a wild type mouse stains positive for shiga toxin-488 (green), ε-toxin-594 (red) and DAPI (blue). Kidney tissue section from a MAL knockout mouse stains positive for shiga toxin-488 and DAPI, but is negative for ε-toxin-594 binding.

FIGS. 23A-23C illustrate that ϵ-toxin kills enriched oligodendrocytes. To evaluate the purity of enriched oligodendrocyte culture, cells were stained with the astrocyte marker GFAP, microglia marker CD6, and OPC marker NG2 (see FIG. 23A). Enriched oligodendrocytes were stained with MBP and proETX-594 (see FIG. 23B). Typical micrograph of oligodendrocyte culture live stained with O1 antibody is presented on the right side (see FIG. 23C). Cells were treated with 100 nM ϵ-toxin and cell viability evaluated by PI inclusion. Quantification of the percent of dead O1 positive cells after ϵ-toxin treatment for 1 and 6 hours is presented on the left side. % Dead Cells was calculated by dividing the number of PI positive O1+ cells by the total number of O1 cells.

Example 6

Identification of the Epsilon Toxin Receptor

Figure 6:
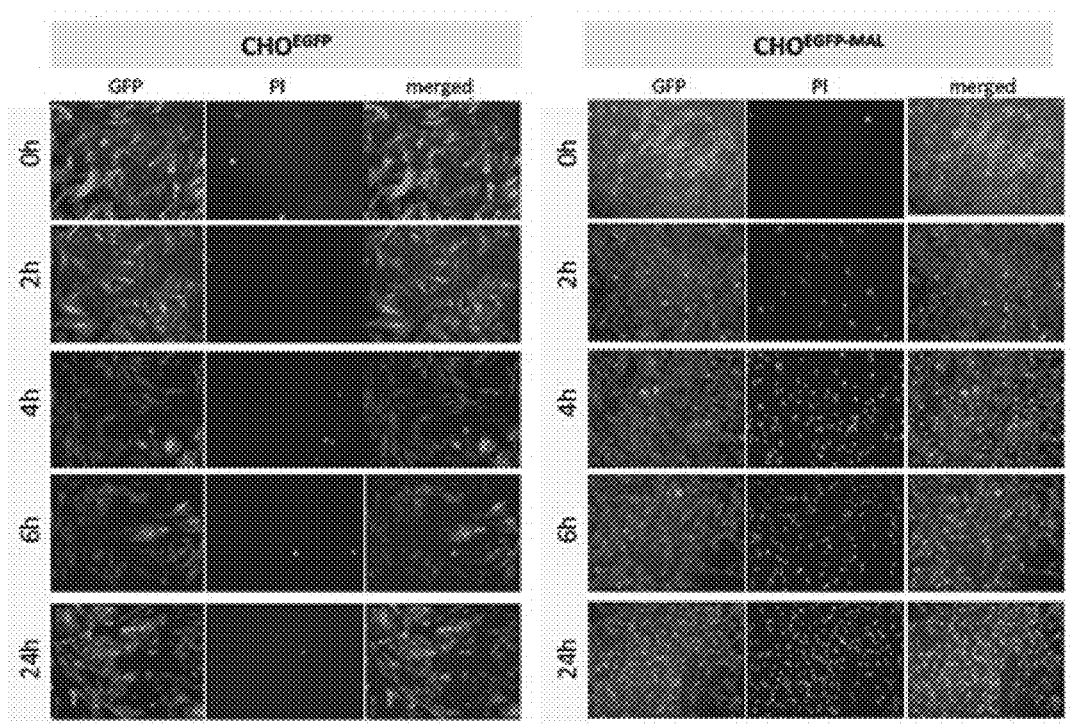
FIG. 6. MAL-1 confers sensitivity of CHO cells to ETX. $CHO^{EGFP}$ and CHOEGFP-MAL cells were incubated with 500 pM ETX for the times indicated (h=hours). Live unfixed cultures were studied by fluorescence microscopy for GFP expression and propidium iodide (PI) staining of DNA as an indicator of cell death.
Figure 7:
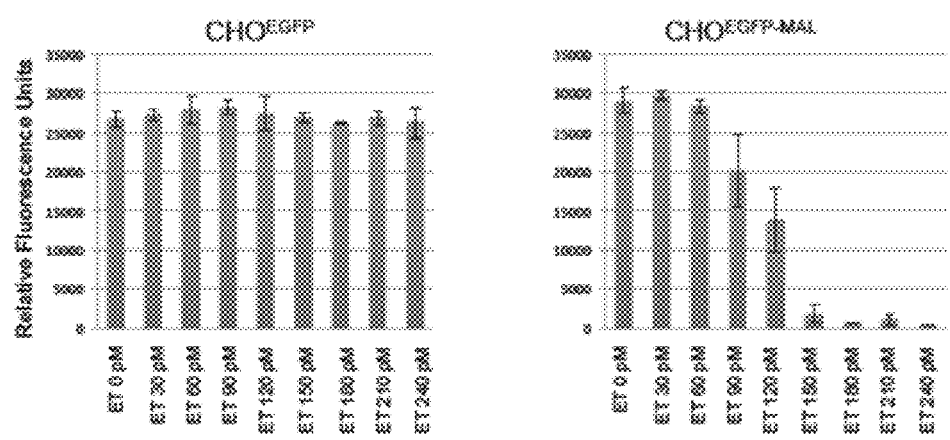
FIG. 7. Dose response analysis of ETX mediated $CHO^{EGFP-MAL}$ cell death using a PrestoBlue (resazurin-based) assay. $CHO^{EGFP-MAL}$ but not $CHO^{EGFP}$ cells are sensitive to ETX in a dose dependent fashion.

Reasoning that the ETX receptor must be encoded by a gene expressed in both BBB endothelial cells and oligodendrocytes (since these are known ETX targets) but not by endothelial cells outside the CNS; a database search of genes expressed in BBB endothelial cells, but not in liver and lung endothelial cells was performed. In addition a search for genes enriched in oligodendrocytes over neurons and astrocytes was also undertaken. Common to both searches were 19 annotated genes. Of these, MAL was the most attractive candidate because its tissue distribution paralleled known targets of ETX. MAL is a tetraspan integral membrane protein named because of its known expression in myelin and lymphocytes[42]. Stable MAL-expressing CHO cells showed marked sensitivity to ETX (FIG. 6). Like the parent CHO cell line, GFP expressing CHO controls did not confer ETX sensitivity. Similarly, as shown in FIG. 7, an analysis using a PrestoBlue assay which is fluorescent when cells are alive, the $CHO^{EGFP-MAL}$ but not $CHO^{EGFP}$ cells are sensitive to ETX in a dose dependent fashion. This further supports that MAL expression is sufficient for ETX mediated cell death, and that ETX activity follows traditional pharmacologtic patterns.

Figure 8:
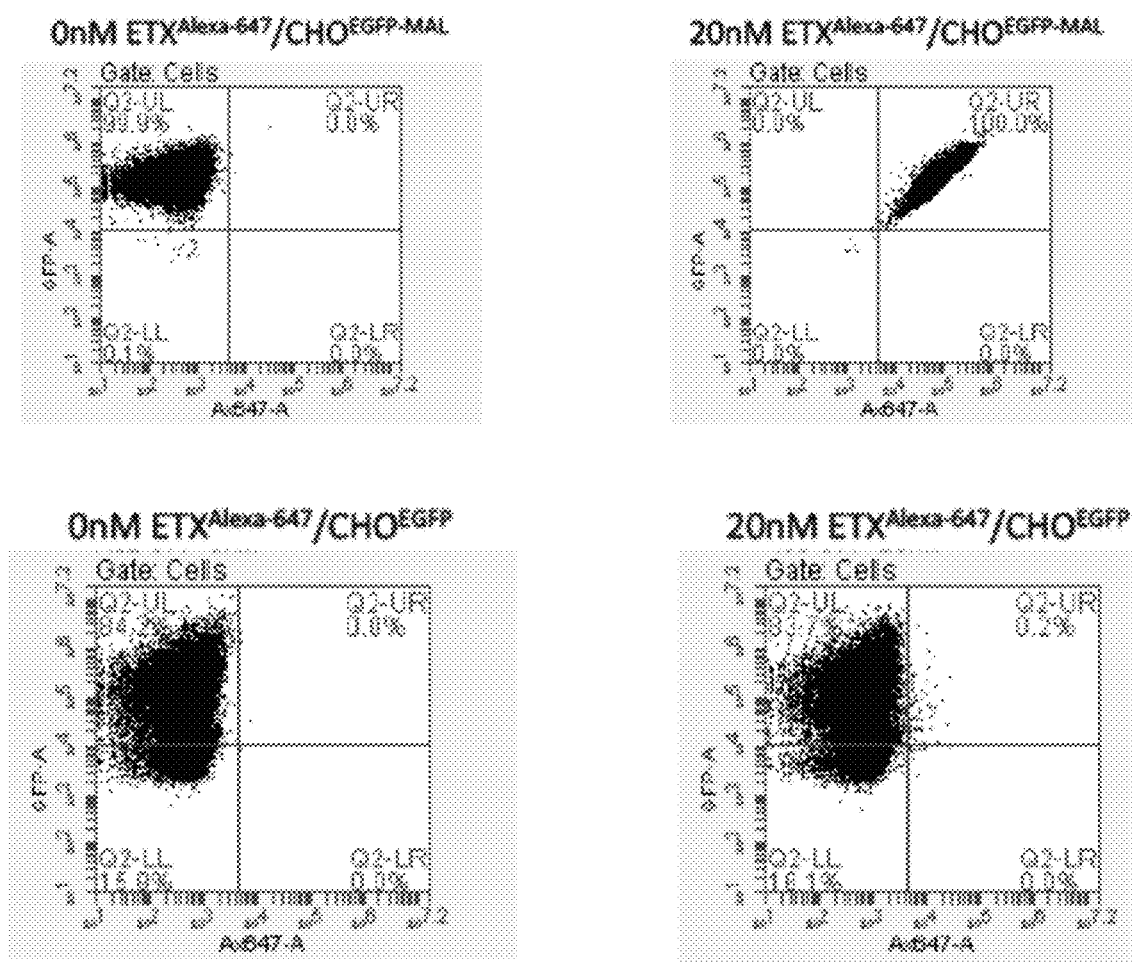
FIG. 8. Fluorescence Activated Cell Sorting (FACS) analysis of $ETX^{Alexa-647}$ binding to CHO cells stably expressing EGFP-MAL or EGFP alone. Dot plots reveal essentially 100% double labeling of EGFP-MAL expressing cells with $ETX^{Alexa-647}$ (second plot). In contrast, CHO cells expressing EGFP alone show no co-labeling with $ETX^{Alexa-647}$ (fourth plot). The first and third dot plots represent EGFP-MAL and EGFP alone expressing CHO cells without $ETX^{Alexa-647}$ FIG. 9. ETX binding to myelin requires MAL. Frozen coronal sections from adult mouse brain through the corpus callosum were stained for proteolipid protein (PLP, green) and Alexa 594-EXT (red). Intense ETX staining is observed to overlap with the PLP-positive in the white matter tracts only in the wild-type mice. Mice lacking MAL (MAL KO) do not show any ETX-594 staining.
Figure 9:
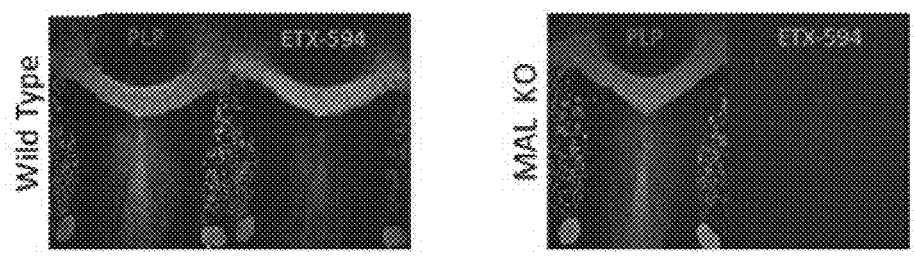

Using a fluorescently labeled ETX ($ETX^{Alexa-647}$) in a FACS study, with CHO cells with and without the MAL receptor, it was found, as shown in FIG. 8, that the $ETX^{Alexa-647}$ only bound to the CHO cells with the MAL receptor.

Pilot toxicity studies were performed in wild-type and MAL knock out (KO) mice and found that a single 50 ng IP dose of active ETX resulted in rapid neurologic deficit in wild-type but not in MAL KO mice.

To determine if MAL is required for the effects of ETX on inducing demyelination, fully myelinated cerebellar slices were generated from wild-type (Mal+/+) and MAL KO (Mal−/−) mice. FIG. 19 shows that ETX binding to myelin requires MAL. Frozen coronal sections from adult mouse brain through the corpus callosum were stained for proteolipid protein (PLP, green) and Alexa 594-EXT (red). Intense ETX staining was observed to overlap with the PLP-positive in the white matter tracts only in the wild-type mice. Mice lacking MAL (MAL KO) do not show any ETX-594 staining. While wild-type mice show near complete demyelination with ETX treatment, MAL KO mice are in contrast completely resistant to the effects of ETX. These results support two important concepts: First that MAL is required for the effects of ETX; and second, that ETX is a highly specific toxin that does not cause non-specific cell injury even at high concentrations.

In addition, FIG. 24A illustrates that MAL is necessary for ϵ-toxin binding to CNS white matter. Brain section from a wild type mouse (top panel) stains for PLP (myelin marker) and ϵ-toxin-594. The merged image shows almost compete overlap. A brain section from a MAL knockout mouse (bottom panel) stains for PLP, but not for ε-toxin-594. FIG. 24B illustrates that MAL is necessary for ε-toxin binding to retinal vessels. Retinal vessels from a wild type mouse stain positive for BSL (a pan endothelial cell microvasculature marker), ε-toxin-594 and DAPI. Retinal vessels from a MAL knockout mouse stain for BSL and DAPI, but fail to stain for ε-toxin-594. Furthermore, FIG. 24C illustrates that MAL is necessary for ε-toxin binding to the cornea. Squamous epithelium of the cornea from a wild type mouse stains positive for BSL lectin, ε-toxin-594 and DAPI. Cornea from a MAL knockout mouse stains for BSL lectin and DAPI, but fails to stain for ε-toxin-594. Moreover, FIG. 24D illustrates that MAL is necessary for ε-toxin binding to renal tubules. Kidney tissue section from a wild type mouse stains positive for shiga toxin-488 (green), ε-toxin-594 (red) and DAPI (blue). Kidney tissue section from a MAL knockout mouse stains positive for shiga toxin-488 and DAPI, but is negative for ε-toxin-594 binding.

Example 7

Screening for Inhibitors of the MAL Receptor

Since the myelin and lymphocyte MAL protein has been identified as the ETX receptor through a series of gain- and loss-of function experiments, as described in Example 2, two high throughput screens had been developed for epsilon toxicity using the stable MAL expressing CHO cells developed by the inventors. The first utilized PrestoBlue, which is sensitive and specific, and has a Z' of 0.7 to 0.85. PrestoBlue is a resazurin-based cell permeable compound converted to the fluorescently active resorufin in the reducing environment of metabolically active cells. Cells were grown on Cellstar 384 well microplates and fluorescence measured with a Perkin-Elmer Envision plate reader. The assay was optimized for cell density and ETX dose and had been used to screen of a library of pharmacologically active compounds.

The second assay utilized propridium iodide as an indicator of cell death. EGFP-, or EGFP-MAL-expressing cells were cultured overnight and then treated with ETX for 30 minutes to 4 hours. Unfixed cultures were incubated with propridium iodide. Plates were read on a IsoCyte laser scanning cytometer.

Example 8

ETX-Antibodies Inhibit Killing of Primary Oligodendrocytes in Mixed Glial Culture

Figure 10:
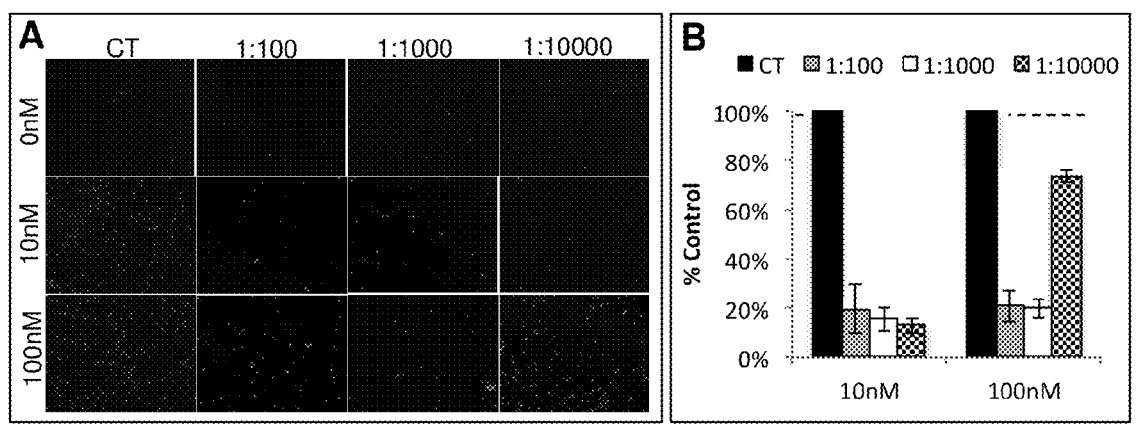
FIG. 10. Neutralizing ε-toxin antibody protects oligodendrocytes from cell death. (10A) The image on the left illustrates mixed primary glial culture being treated with the indicated dilutions of a neutralizing antibody (NAB) against ε-toxin and ε-toxin dose for 24 hours. Cell viability was evaluated by PI inclusion. (10B) Quantification of PI staining from studies shown in 10A. Neutralizing ε-toxin antibody protects oligodendrocytes from cell death. Primary mixed glial cells were treated with the indicated dilutions of a neutralizing antibody (NAB) against ε-toxin and ε-toxin was dosed for 24 hours. Cell viability, evaluated by PI staining of nuclie, was quantified by Image J. Results shown are flourescense intensity as a percent of control.
Figure 11:
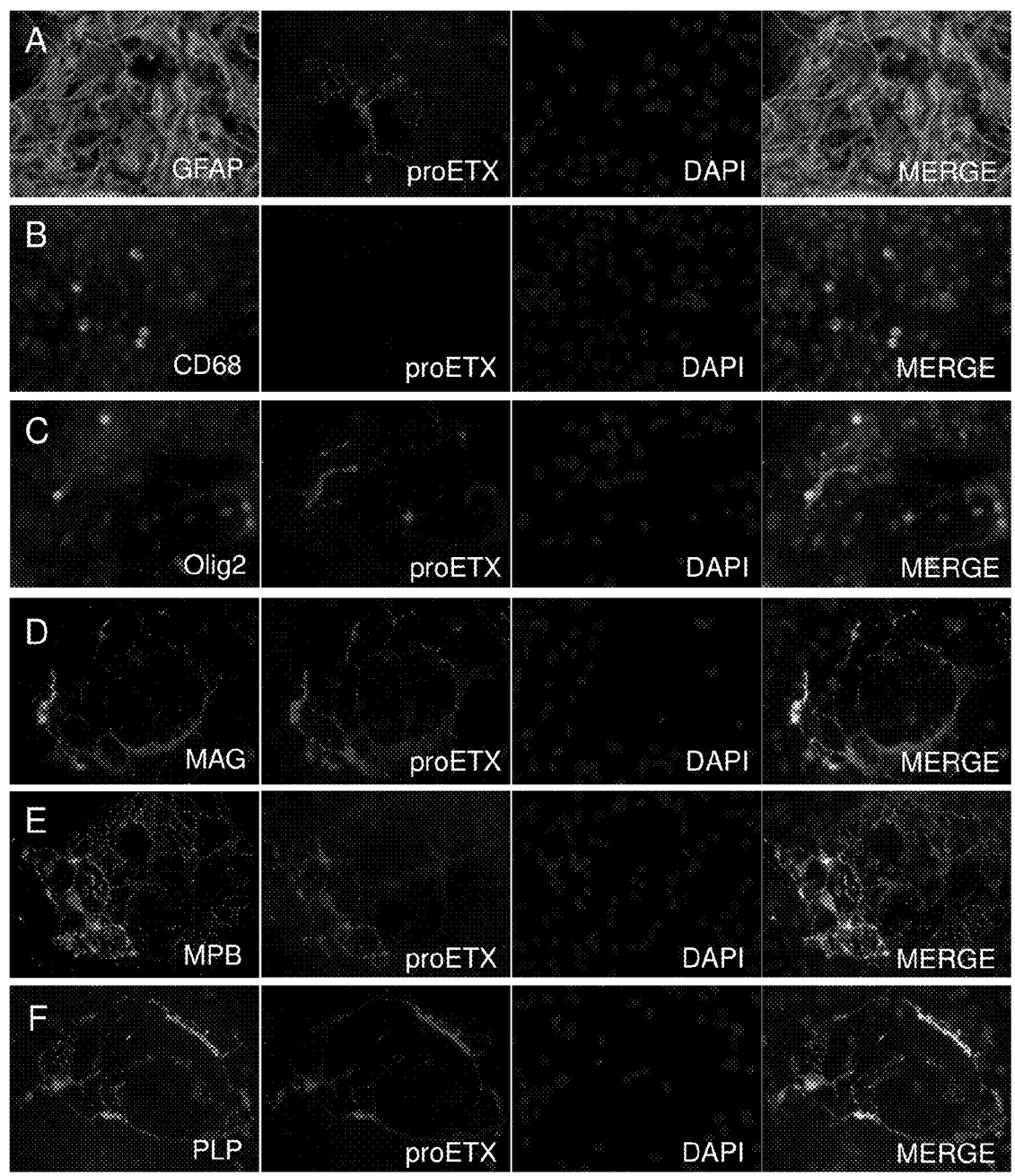
FIG. 11. ε-Toxin specifically binds to oligodendrocytes in the CNS. Mixed murine glial cells were harvested from p0-6 pups and cultured for 10 days in media promoting oligodendrocyte differentiation. Cells were fixed in 4% PFA and stained with antibodies specific for different glial populations including GFAP for astrocytes (11A), CD68 for microglial (11B), Olig2 for all oligodendrocyte lineages (11C), and MAG (11D), MPB (11E), and PLP (11F) for mature oligodendrocytes. To determine specificity of e-toxin binding, cells were probed with Alexaflour 598 conjugated ε-protoxin (proETX). Nuclei were visualized with DAPI.

*C. perfringens* epsilon toxin selectively targets CNS endothelial cells and oligodendrocytes. To determine if ε-toxin induced oligodendrocyte cell death and demyelination could be inhibited, cells were treated with a neutralizing antibody (NAB) against ε-toxin prior to toxin treatment. Primary oligodendrocytes were generated either in enriched culture or in the context of mixed CNS cultures. FIGS. 10A and 10B show that neutralizing ε-toxin antibody (NAB) protects oligodendrocytes from cell death. When mixed primary glia culture was treated with ε-toxin alone, a large amount of cell death was visible by PI staining 24 hours after treatment. If cells were treated with both the neutralizing antibody (NAB) and ε-toxin, a marked reduction in PI staining was observed.

Cells treated with a 1:100 and 1:1,000 dilution of the NAB were completely protected from treatment with 10 nM or 100 nM ε-toxin for 24 hours. Cells treated with a 1:10,000 dilution of NAB were completely protected against 10 nM ε-toxin and partially protected against 100 nM ε-toxin. Quantification was done using image J either measuring mean fluorescence intensity or the number of PI⁺ nuclei. Measurement on fluorescence intensity and cell number by Image J: Single-channel/monochromatic images taken with a SPOT cooled camera (Diagnostic Instruments) mounted on an Axiskop2 fluorescence microscope (Carl Zeiss) were directly imported in ImageJ64 (NIH) and converted into a 8-bit grey format. Adjust threshold to the image as a whole (or regions of interest) to pick up signals to be measured. For comparative analysis, the same threshold values were applied to all images taken from all experimental groups. Applied the threshold adjustment to convert the image into a binary image. For fluorescence intensity analysis, measurement was automatically performed on the binary image for mean and integrated density. For cell counts, Analyze Particles function was selected to automatically count the particle (cell, nuclei, etc) numbers, analyze particle properties (size, shape, etc) and distribution. The measurement data were exported directly into Excel (Microsoft) for statistical analysis.

These studies demonstrate that neutralizing antibodies (NAB) directed against ε-toxin are sufficient to block the cytotoxic effects of ε-toxin on oligodendrocytes. Oligodendrocytes are the myelin forming cells in the CNS and are necessary for the maintenance of myelin after it has been generated. When oligodendrocytes die in the newly forming MS lesion, they are no longer able to support and maintain myelin and thus demyelination occurs. Epsilon toxin can thus induce demyelination both be direct attack of myelin and by targeting oligodendrocytes for death. The employment of NAB against ε-toxin will this provide a method to prevent oligodendrocyte death and prevent demyelination. NAB can be administered directly to a patient, or, they can be induced by vaccination procedures. In either case protection against oligodendrocyte injury and demyelination is provided.

Example 9

Blockage of ETX-Induced Oligodendrocyte Death and Demyelination in Organotypic Cerebellar Slices by Neutralizing Antibodies New MS lesions show evidence of oligodendrocyte death, secondary demyelination due to a loss of oligodendrocytes which make and maintain the myelin internode, but an absence of neuronal, strocyte or microglial injury/death. The most effective way to test if ETX fits the specific phenotype of the new MS lesion is to test the effects of ETX in the context of the complex tissue microenvironment of the CNS. To accomplish this, organotypic cerebellar slice cultures were generated. The advantage of cerebellar slice cultures is that the complex tissue cytoarchetecture is completely maintained since cellular relationships are not disrupted by tissue disruption. In addition, organotypic cultures allow highly quantitative methodology that can not be applied to whole animal work. Finally, organotypic cultures minimize the use of vertebrate animals which is a mandate of all IACUCs and the National Institutes of health. Therefore, the cerebellar slice cultures were generated as previously described from postnatal day 8 (P8) mice and after 4 weeks cultures were treated with E or PBS. Since modeling the nascent lesion in MS was interested, cultures were treated for only 20 hours with toxin and then assessed for oligodendrocytes with olig2 and CNPase, and myelin with MBP and MAG. In control cultures there were numerous olig2 positive cells as well as extensive myelination detected with MBP and MAG staining. At a dose of 50 pM for just 20 hours, there was dramatic reduction in the number of olig2 positive cells with preservation of MBP staining. With escalating doses, there was a greater reduction in olig2 positive cells and at the highest doses there was reduction in myelin staining as well. MAL is expressed in oligodendrocyte soma, compact myelin and paranodes. Low doses of E are sufficient to cause oligodendrocyte death with preservation of myelin architecture for days before myelin degenerates due to dying back. At high doses of E, toxin kills oligodendrocytes but also binds to and forms pores in myelin leading to more rapid osmolysis. It is the former case (oligodendrocyte death with preservation of myelin) to model.

Figure 13A:
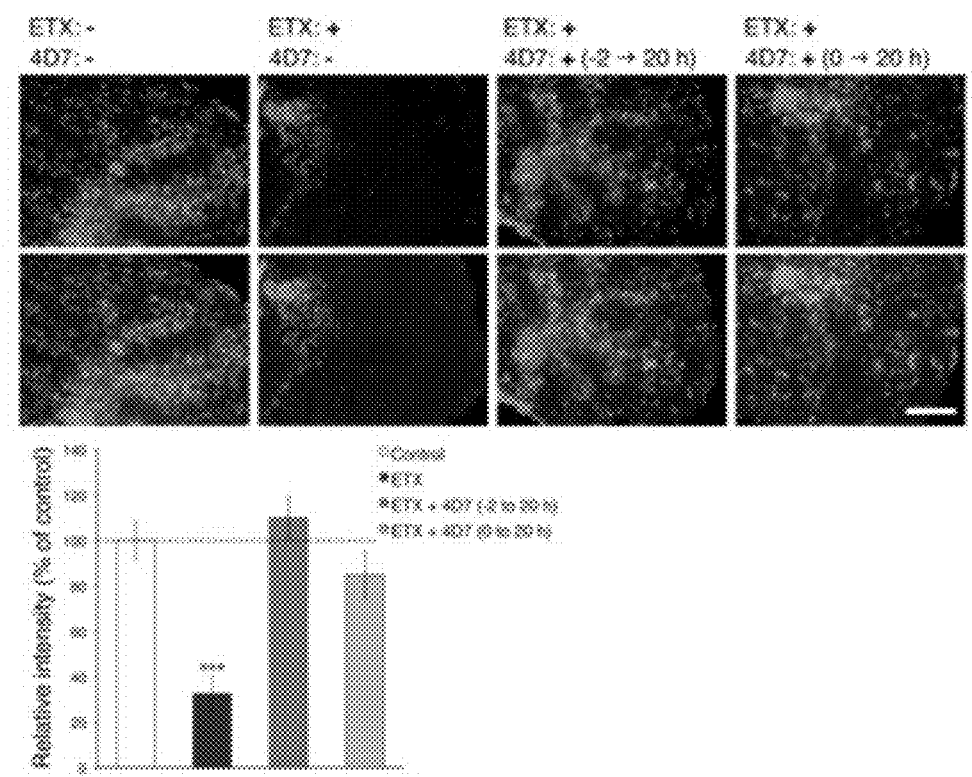
FIGS. 13A-13B. Neutralizing antibodies against ETX (4D7 and 5B7) block ETX-induced MBP reduction in cerebellar slices.
Figure 13B:
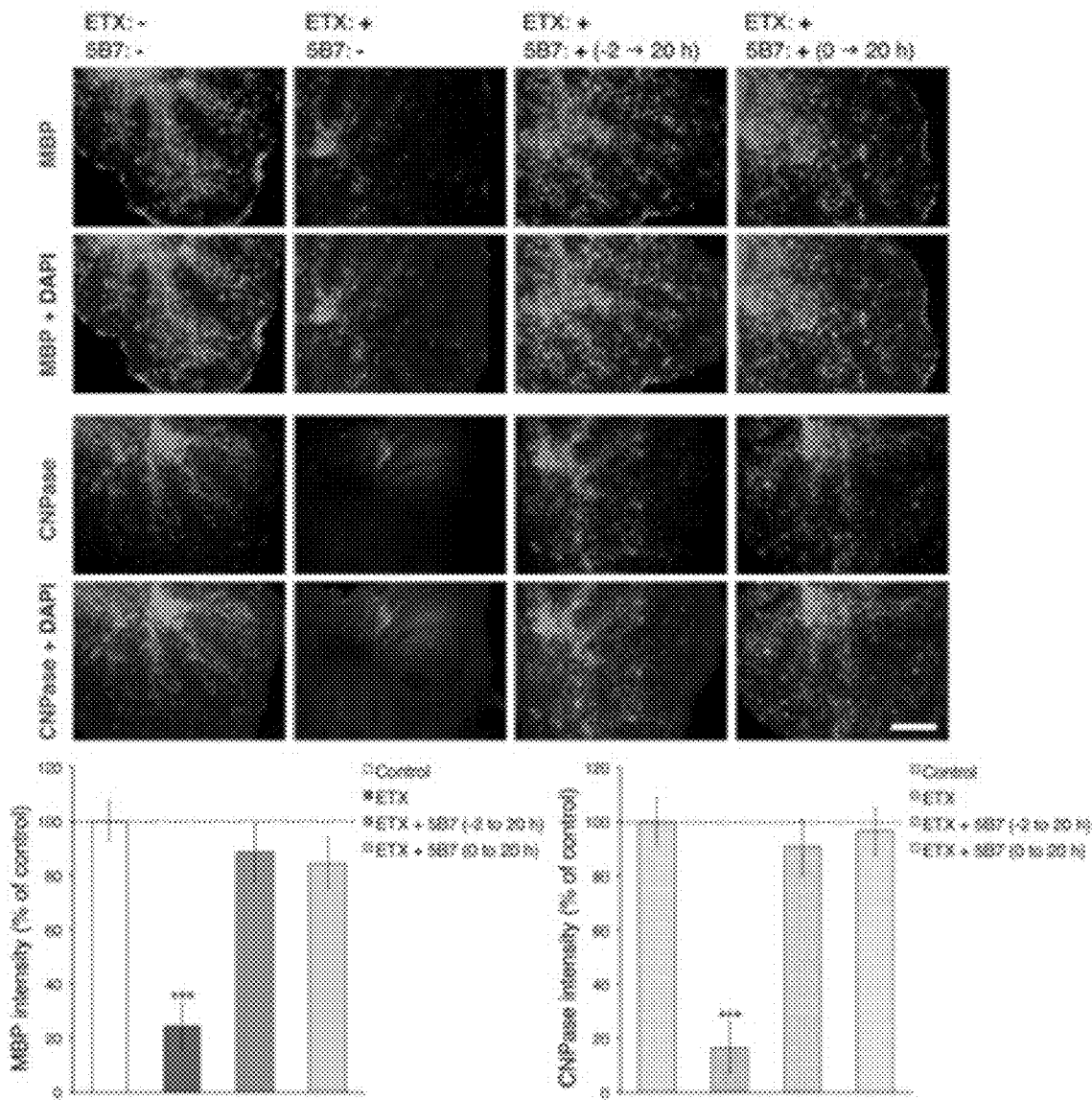

FIGS. 13A and 13B illustrate that neutralizing antibodies against ETX (4D7 and 5B7) block ETX-induced MBP reduction in cerebellar slices. Cerebellar slices were maintained in culture for 4 weeks leading to robustly myelinated explants. Epsilon toxin (ETX) was added to the explants for the times indicated without or with ETX-neutralizing antibodies. For both clones of neutralizing antibody there was robust blocade of the effects of epsilon toxin on demyelination as indicated with MBP staining. FIG. 13A provides representative images (top rows) and quantitation (bottom panel) of MBP-immunostaining (green) with slices exposed to PBS (vehicle control, first column) or 5 nM ETX (columns 2-4) for 20 hours. ETX-neutralizing monoclonal antibody 4D7 was omitted (column 1 and 2) or added in slice culture at two different time points: 2 hours prior to (column 3) and concurrent with (column 4) ETX treatment. DAPI (blue) is counterstained to identify cell nuclei. n=5-6 slices for each condition, normalized to respective controls (100%); * p<0.001, two-tailed t-test. Similar results were obtained in three independent experiments. Scale bar represents 500 µm. FIG. 13B provides representative images (top rows) and quantitation (bottom panels) of MBP (row 1 and 2, bottom left panel, green)- and CNPase (row 3 and 4, bottom right panel, green)-immunostaining with slices exposed to PBS (vehicle control, first column) or 5 nM ETX (columns 2-4) for 20 hours. ETX-neutralizing monoclonal antibody 5B7 was omitted (column 1 and 2) or added in slice culture at two different time points: 2 hours prior to (column 3) and concurrent with (column 4) ETX treatment. DAPI (blue) is counterstained to identify cell nuclei. n=5-6 slices for each condition, normalized to respective controls (100%); * p<0.001, two-tailed t-test. Similar results were obtained in two independent experiments. Scale bar represents 500 µm.

Example 10

Antibody Against Epsilon Toxin Protects Mice

To determine if neutralizing antibodies directed against ε-toxin are capable of preventing neurologic disability, mice were administered toxin and antibody via tail vein injection. Mouse#1 was injected with 100 microliters of a neutralizing antibody directed against ETX ten minutes prior to injection of 10 ng/g of ETX. Mouse#2 was injected with 10 ng/g of ETX alone at the same time that mouse 1 received dosing. Videos were taken 10 minutes after administration of ETX. ETX dose: 10 ng/g of mouse or approximately 5 nM (based on blood volume); Antibody dose: 100 microliters of antibody (1:20 dilution). Animals were then observed for neurological deficits. It was observed that mouse #1, was active, ambulates normally and demonstrates normal cage exploration. In contrast, mouse #2 was immobile, has marked motor and cerebellar deficits, and does not explore the cage. This experiment demonstrates that a neutralizing antibody directed against ε-toxin is sufficient to prevent the neurological consequences of ε-toxin in an animal. Clinically, NAB can be administered directly or generated in the host through vaccination.

Example 11

Vaccine Against ETX and/or C. perfringens Type B and D Bacterial Strain

Vaccination against ETX is designed to: prevent binding of ETX to its cellular receptor; prevent association of receptor monomers into oligomers and thus prevent pore formation; block the pore itself; or in anyway inhibit the cytotoxic effects of ETX. The immunogen component of the vaccine is derived from the entire ETX protein, the ETX protein harboring one or more site directed amino acid mutations, or one or more polypeptides from the protein. Mutant forms of ETX to be used in vaccine preparation include but are not limited to: mutant recombinant ETX H106P (histadine106 substituted by proline) (Oysten et al 1998); mutant recombinant ETX W190K (Oysten et al 1998); mutant recombinant ETX H149A (Oysten et al 1998); mutant recombinant ETX Y29E (Ivie and McClain, 2012); mutant recombinant ETX Y30E (Ivie and McClain, 2012); mutant recombinant ETX Y36E (Ivie and McClain, 2012); and mutant recombinant ETX Y196E (Ivie and McClain, 2012).

Mutant recombinant ETX harboring two or more of the cited mutations, (e.g.: mutant recombinant ETX harboring the H106P and the H149A mutations, mutant recombinant ETX harboring the H106P and the W190K mutations, mutant recombinant ETX harboring the W190K and the H149A mutations, and mutant recombinant ETX harboring the H106P, H149A and the W190K mutations) will be utilized. Mutant recombinant ETX proteins are expressed alone or as fusion proteins with glutathione S-transferase or another sequence designed to provide protein stability and/or rapid purification.

As C. perfringens beta-toxin is known to form pores in endothelial cells and therefore when present, beta-toxin may accentuate toxemia from ETX, vaccination against both ETX and beta-toxin can be useful. Non toxic fusions of ETX and beta-toxin will be generated as immunogens for vaccination (Langroudi et al 2013).

In another strategy, anti-idiotype antibodies will be used in vaccine strategies. The relevant idiotypic region within monoclonal or polyclonal antibodies that function to neutralize ETX are used to generate anti-idiotype antibodies. The anti-idiotype antibodies resemble the original immunogenic portion of ETX that resulted in protective immunity and thus are used in vaccine strategies to promote immunity against ETX without risk of administering toxin or toxoid. Examples include raising anti-idiotype antibodies to mAb A5C12 (Percival et al, 1990); mAb 4D7, mAb 5B7 (*Dev Biol Stand.* 1999; 101:85-94; McClain and Cover 2007)

Vaccination will also be accomplished by immunization with recognized amino acid sequences within epsilon toxin that are identified neutralization epitopes. These include but are not limited to the amino acid sequence 134-145 of epsilon toxin described previously (McClain and Cover 2007). Sequences representing the epitopes recognized by neutralizing antibodies are used as immunogens by themselves or conjugated to other peptide or protein sequences.

Epsilon toxoid is a traditional method for vaccination. Toxoid is prepared by chemical modification of active epsilon toxin or pro-toxin. Chemical modification can be achieved by treatment with formalin, formaldehyde, paraformaldehyde or through other chemical modification methodologies. Neutralizing epsilon toxin antibodies are then generated within the host following effective immunization with toxoid as previously described Uzal, Wong, et al, 1999; Bentancor et al, 2009; Titball, 2009; Chandran et al, 2010; Uzal et al, 1997; Blackwell et al, 1983; Mathur et al 2010; LoBato et al, 2010).

Example 12

Use of Bacteriophage Lysins to Combat Clostridium perfringens Colonization/Infection Endolysins are bacteriophage enzymes that target bonds in the peptidoglycan of bacteria. Endolysins are normally produced within the bacteriophage-infected bacterium and require a second protein, holing, to produce holes in the bacterial cell membrane thus allowing access of the endolysin to the cell wall. Endolysin mediated cleavage of peptidoglycan results in the destruction of the cell wall thus killing the bacterium. Endolysins specific to *clostridium perfringens* have demonstrated bactericidal effects against this organism (Allaart et al, 2013). Delivery of the endolysin to the MS patient is accomplished though either direct ingestion of the protein in a formulation that protects it against proteolytic degradation, via a bacteriophage, or by oral administration of a genetically engineered probiotic strain expressing the endolysin (Allaart et al 2013). The endolysins or relevant bacteriophages specific to *Clostridium perfringens* that are used include but are not limited to: endolysin CP25L (Gervasi et al, 2013); MurNAc-LAA (also known as peptidoglycan aminohydrolase, NAMLA amidase, NAMLAA, amidase 3, and peptidoglycan amidase; EC 3.5.1.28) and the isolated gene PlyCpAmi (Tillman et al, 2013); endolysin PF01520, an N-acetylmuramoyl-1-alanineamidase (Seal, 2013); lysins encoded by genes annotated in FIG. 1 of Schmitz et al, 2010; Acp (Camiade et al, 2010); Lysin Ply3626, a peptidoglycan hydrolase (Zimmer et al, 2002). *C. perfringens* bacteriophage strains include but are not limited to: ΦCPV4, φZP2, φCP7R (Volozhantsev et al, 2012); Φ3626 (Zimmer et al, 2002).

Discussion and Conclusion

Kurtzke and Hyllested reported a detailed analysis of MS epidemics on the Faroe Islands[26]. Prior to 1943, there were no documented cases of MS on the Faroes, an impressive absence considering that neighboring Iceland, Sweden and Denmark each reported a high annual MS incidence. With the common Norse ancestry of the Faroese, Icelandic, Swedish and Dane peoples, the absence of MS in the Faroes prior to 1943 strongly suggests the existence of an environmental initiator. During World War II, coincident with the arrival of British troops, the first of four documented MS epidemics within native Faroese were reported[26-28]. Since haplotypes, in that short time period, are undoubtedly stable, this information further argues that MS must begin with an environmental trigger. Kurtzke also identified a co-incident rise in gastrointestinal infections following British military occupation and postulated the trigger to be a pathogen spread by fecal-oral transmission[29]. T. C. G. Murrell noted that the prevalence of MS was high in regions where sheep were concentrated and speculated as to the possibility that ETX or other sheep associated pathogens may be responsible for causing MS[13].

Assuming that MS begins with an environmental trigger, and that the earliest lesions are characterized by BBB disruption and oligodendrocyte apoptosis, it seems probable the environmental trigger must target these two cells/structures. The data presented here shows that *C. perfringens* ETX fulfills the relevant criteria for a MS disease initiator. ETX binds to BBB endothelium, disrupts BBB function and binds to CNS white matter[15-17]. Immunoreactivity to ETX is identified in about 10% of people with MS. The low value of immunoreactivity to ETX in MS may be explained by the difficulty mammals have maintaining humoral immunity to ETX[22]. These studies also found that people with MS are less likely to harbor *C. perfringens* type A, a toxinotype thought to outcompete *C. perfringens* types B and D for resources in an ecological niche[24]. One case was identified in which a newly diagnosed patient harbored *C. perfringens* type B. Eight months after testing positive for *C. perfringens* type B, this patient reverted to negative for all *C. perfringens* toxinotypes, an example of the transient nature of bacillus growth and/or detection limits. Identification of *C. perfringens* types B or D in humans may be difficult, as *C. perfringens* forms endospores that are resistant to standard DNA extraction methods. Additionally, the organism is likely to exist in low abundance in the upper GI tract, only rarely entering growth phases that render it detectable.

Although ETX binds to peripheral nervous system (PNS) myelin, as it does CNS myelin[15], autoradiograph studies show that ETX only targets the CNS and not the PNS[30]. It seems likely that ETX fails to bind to PNS endothelial cells that comprise the blood nerve barrier; therefore PNS myelin is not exposed to the toxin. Further, binding of ETX to retinal veins that form the blood retinal barrier (BRB), a CNS barrier analogous to the BBB, may explain the enigmatic observation of periphlebitis retinae in people with MS. The human retina is typically devoid of myelin, yet vascular scarring occurs[31]. Primary ETX action on the BRB may result in retinal phlebitis that is independent of oligodendrocytes or myelin. Furthermore, serum protein leakage and the accumulation of perivenular monocytes in the absence of oligodendrocyte apoptosis or demyelination are often observed in pathologic MS brain specimens. These observations may similarly be due to subtle insult of the endothelium and a secondary innate immune response[6].

Therefore, the studies presented herewith identify *Clostridium perfringens* epsilon toxin (ETX) as a primary environmental trigger for Multiple Sclerosis (MS). In summary, nascent MS lesions are characterized by blood-brain barrier (BBB) permeability and oligodendrocyte cell death in the absence of an adaptive immune infiltrate. ETX targets brain vasculature and oligodendrocytes/myelin, key features of the nascent MS lesion. In a study of a well-characterized population of MS patients and healthy controls for *C. perfringens* carriage and humoral immunity to ETX, it was found that immunoreactivity to ETX is 10 times more prevalent in people with MS than in healthy controls, indicating prior exposure to ETX in the MS population. An exploration of carriage of the different *C. perfringens* toxinotypes in the gastrointestinal tract of MS patients and healthy controls showed that the human commensal *Clostridium perfringens* Type A was present in approximately 50% of healthy human controls compared to only 23% in MS patients. *C. perfringens* type A, which does not carry the plasmid encoding ETX, is known to outcompete *C. perfringens* types B and D, the epsilon toxin-producing toxinotypes. *Clostridium perfringens* type B, an epsilon toxin-secreting *bacillus*, was identified in a young woman at clinical presentation of MS with actively enhancing lesions on brain MRI. These findings represent the first time that *C. perfringens* type B has been detected in a human. Epsilon toxin's tropism for BBB and binding to oligodendrocytes/myelin makes it a provocative candidate for nascent lesion formation in MS, demonstrating how the human microbiome might influence susceptibility to MS by hindering carriage of pathogenic organisms.

REFERENCES

1. Adams R D, K. C. (1952). "The morbid anatomy of the demyelinative disease." *Am J Med* 12(5): 510-546.
2. Barnett, M. H., A. P. Henderson, et al. (2006). "The macrophage in MS: just a scavenger after all? Pathology and pathogenesis of the acute MS lesion." *Mult Scler* 12(2): 121-132.
3. Barnett, M. H., J. D. Parratt, et al. (2009). "Immunoglobulins and complement in postmortem multiple sclerosis tissue." *Annals of neurology* 65(1): 32-46.
4. Barnett, M. H., J. D. Parratt, et al. (2009). "MS: is it one disease?" *Int MS J* 16(2): 57-65.
5. Barnett, M. H. and J. W. Prineas (2004). "Relapsing and remitting multiple sclerosis: Pathology of the newly forming lesion." *Annals of Neurology* 55(4): 458-468.
6. Prineas, J. W. and J. D. Parratt (2012). "Oligodendrocytes and the early multiple sclerosis lesion." *Annals of neurology* 72(1): 18-31.
7. Henderson, A. P. D., M. H. Barnett, et al. (2009). "Multiple sclerosis: Distribution of inflammatory cells in newly forming lesions." *Annals of Neurology* 66(6): 739-753.
8. Lassmann, H. (2011). "Review: the architecture of inflammatory demyelinating lesions: implications for studies on pathogenesis." *Neuropathology and applied neurobiology* 37(7): 698-710.
9. Havard, H. L., S. E. Hunter, et al. (1992). "Comparison of the nucleotide sequence and development of a PCR test for the epsilon toxin gene of *Clostridium perfringens* type B and type D." *FEMS microbiology letters* 76(1-2): 77-81.
10. Meer, R. R. and J. G. Songer (1997). "Multiplex polymerase chain reaction assay for genotyping *Clostridium perfringens.*" *American journal of veterinary research* 58(7): 702-705.
11. Popoff, M. R. (2011). "Epsilon toxin: a fascinating pore-forming toxin." *FEBS Journal* 278(23): 4601-15.
12. Murrell, T. G., L. S. Harbige, et al. (1991). "A review of the aetiology of multiple sclerosis: an ecological approach." *Ann Hum Biol* 18(2): 95-112.
13. Murrell, T. G., P. J. O'Donoghue, et al. (1986). "A review of the sheep-multiple sclerosis connection." *Med Hypotheses* 19(1): 27-39.
14. Bokori-Brown, M., C. G. Savva, et al. (2011). "Molecular basis of toxicity of *Clostridium perfringens* epsilon toxin." *FEBS Journal* 278(23): 4589-601.
15. Dorca-Arévalo, J., A. Soler-Jover, et al. (2008). "Binding of ϵ-toxin from *Clostridium perfringens* in the nervous system." *Veterinary Microbiology* 131(1-2): 14-25.
16. Finnie, J. W. (1984). "Histopathological changes in the brain of mice given *Clostridium perfringens* type D epsilon toxin." *J Comp Pathol* 94(3): 363-370.
17. Finnie, J. W. (1984). "Ultrastructural changes in the brain of mice given *Clostridium perfringens* type D epsilon toxin." *J Comp Pathol* 94(3): 445-452.
18. Zhu, C., M. N. Ghabriel, et al. (2001). "*Clostridium perfringens* prototoxin-induced alteration of endothelial barrier antigen (EBA) immunoreactivity at the blood-brain barrier (BBB)." *Experimental neurology* 169(1): 72-82.
19. Dawson, J. (1916) The histology of multiple sclerosis. *Trans R Soc Edinburgh* 50: 517-578.
20. Dorca-Arevalo, J., M. Martin-Satue, et al. (2012). "Characterization of the high affinity binding of epsilon toxin from *Clostridium perfringens* to the renal system." *Veterinary Microbiology* 157(1-2): 179-189.
21. Erickson, J. E. and R. H. Deibel (1978). "New medium for rapid screening and enumeration of *Clostridium perfringens* in foods." *Appl Environ Microbiol* 36(4): 567-571.
22. Blackwell, T. E., D. G. Butler, et al. (1983). "Enterotoxemia in the goat: the humoral response and local tissue reaction following vaccination with two different bacterin-toxoids." *Canadian journal of comparative medicine. Revue canadienne de medecine comparee* 47(2): 127-132.
23. Knapp, O., E. Maier, et al. (2009). "Identification of the channel-forming domain of *Clostridium perfringens* Epsilon-toxin (ETX)." *Biochimica et Biophysica Acta (BBA)—Biomembranes* 1788(12): 2584-2593.
24. Itodo, A. E., A. A. Adesiyun, et al. (1986). "Toxin-types of *Clostridium perfringens* strains isolated from sheep, cattle and paddock soils in Nigeria." *Vet Microbiol* 12(1): 93-96.
25. Carman, R. J., S. Sayeed, et al. (2008). "*Clostridium perfringens* toxin genotypes in the feces of healthy North Americans." *Anaerobe* 14(2): 102-108.
26. Kurtzke, J. F. and K. Hyllested (1975). "Multiple sclerosis: an epidemic disease in the Faeroes." *Transactions of the American Neurological Association* 100: 213-215.
27. Kurtzke, J. F. (1993). "Epidemiologic evidence for multiple sclerosis as an infection." *Clinical microbiology reviews* 6(4): 382-427.
28. Kurtzke, J. F. and A. Heltberg (2001). "Multiple sclerosis in the Faroe Islands: an epitome." *Journal of clinical epidemiology* 54(1): 1-22.
29. Wallin, M. T., A. Heltberg, et al. (2010). "Multiple sclerosis in the Faroe Islands. 8. Notifiable diseases." *Acta Neurologica Scandinavica* 122(2): 102-9.
30. Tamai, E., T. Ishida, et al. (2003). "Accumulation of *Clostridium perfringens* Epsilon-Toxin in the Mouse Kidney and Its Possible Biological Significance." *Infection and Immunity* 71(9): 5371-5375.
31. Kerrison, J. B., T. Flynn, et al. (1994). "Retinal pathologic changes in multiple sclerosis." *Retina* 14(5): 445-451.
32. Schmitz J E, Ossiprandi M C, Rumah K R, Fischetti V A (2011) "Lytic enzyme discovery through multigenomic sequence analysis in *Clostridium perfringens*. Appl Microbiol Biotechnol. 89(6):1783-95.
33. McClain M S & Cover T L (2007) "Functional analysis of neutralizing antibodies against *Clostridium perfringens* epsilon-toxin." *Infect Immun* 75(4):1785-1793.
34. Hauer P J & Clough N E (1999). "Development of monoclonal antibodies suitable for use in antigen quantification potency tests for clostridial veterinary vaccines. *Dev. Biol. Stand.* 101:85-94.
35. Sayeed S, Fernandez-Miyakawa M E et al. (2005) "Epsilon-toxin is required for most *Clostridium perfrin-* gens type D vegetative culture supernatants to cause lethality in the mouse intravenous injection model." *Infect Immun.* 73(11):7413-21.

36. Martin T A, Harrison G M et al (2011) "HAVcR-1 reduces the integrity of human endothelial tight junctions." *Anticancer Res.* 31(2):467-73.
37. Ivie S E, McClain M S. (2012) "Identification of Amino Acids Important for Binding of *Clostridium perfringens* Epsilon Toxin to Host Cells and to HAVCR1." *Biochemistry.* 2012 Sep. 12. [Epub ahead of print]
38. Titball R W, Williamson E D et al (2002) "*Clostridium perfringens* Vaccines" U.S. Pat. No. 6,403,094.
39. Souza A M, Reis J K et al (2010) "Molecular cloning and expression of epsilon toxin from *Clostridium perfringens* type D and tests of animal immunization. *Genet Mol Res.* 18; 9(1):266-76.
40. Ivie S E, Fennessey C M, et al (2011) "Gene-Trap Mutagenesis Identifies Mammalian Genes Contributing to Intoxication by *Clostridium perfringens* ϵ-Toxin". *PLoS ONE* 6(3): e17787.doi:10.1371/journal.pone.0017787
41. Oyston P C, Payne D W, et al. (1998) "Production of a non-toxic site-directed mutant of *Clostridium perfringens* epsilon-toxin which induces protective immunity in mice." Microbiology. 144 (Pt 2):333-41.
42. Schaeren-Wiemers, N. Valenzuela, D. M. Frank, M. & Schwab, M. E. Characterization of a rat gene rMAL, encoding a protein with four hydrophobic domains in central and peripheral myelin. J Neorsci 15, 5753-5764 (1995).
43. Allart, et al. (2013) "Predisposing factors and prevention o *Clostridium perfringens*-associated enteritis," *Comparative Immunology, Microbiology and Infectious Diseases*, 36:449-464.
44. Gervasi et al. (2013) "Expression and delivery of an endolysin to combat *Clostridium perfringens*," *Appl. Microbiol. Biotechnol.*, DOI 10.1007/s00253-013-5128-y.
45. Seal (2013) "Characterization of bacteriophages virulent for *Clostridium perfringens* and identification of phage lytic enzymes as alternatives to antibiotics for potential control of the bacterium," *Tomorrow's Poultry: Sustainability and Safety Symposium*, 526-533
46. Tillman et al. (2013) "Expression of *Clostridium perfringens* genome-encoded putative N-acetylmuramoyl-L-alanine amidase as a potential antimicrobial to control the bacterium," *Arch Microbiol.*, 195:675-681.
47. Volozhantsev, et al. (2012) "Molecular characterization of podoviral bacteriophages virulent for *Clostridium perfringens* and their comparison with members of the Picovirinae," *PLoS ONE*, 7(5):1-12.
48. Camiade et al., (2010) "Characterization of Acp, a peptidoglycan hydrolase of *Clostridium perfringens* with N-acetylglucosaminidase activity that is implicated in cell separation and stress-induced autolysis," *J. Bacteriol.*, 192(9):2373-84.
49. Zimmer et al. (2002) "The murein hydrolase of the bacteriophage phi3626 dual lysis system is active against all tested *Clostridium perfringens* strains," *Appl. Environ. Microbiol.*, 68(11):5311-7.

The following statements are potential claims that may be converted to claims in a future application. No modifications of the following statements should be allowed to affect the interpretation of claims which may be drafted when this provisional application is converted into a regular utility application.

SEQUENCE LISTING

Amino Acid Sequence of ETX Peptide
SEQ ID NO: 1

```
MKKNLVKSLA IASAVISIYS IVNIVSPTNV IAKEISNTVS
NEMSKKASYD NVDTLIEKGR YNTKYNYLKR MEKYYPNAMA
YFDKVTINPQ GNDFYINNPK VELDGEPSMN YLEDVYVGKA
LLTNDTQQEQ KLKSQSFTCK NTDTVTATTT HTVGTSIQAT
AKFTVPFNET GVSLTTSYSF ANTNTNTNSK EITHNVPSQD
ILVPANTTVE VIAYLKKVNV KGNVKLVGQV SGSEWGEIPS
YLAFPRDGYK FSLSDTVNKS DLNEDGTINI NGKGNYSAVM
GDELIVKVRN LNTNNVQEYV IPVDKKEKSN DSNIVKYRSL
SIKAPGIK
```

Nucleotide Sequence encoding ETC Peptide
SEQ ID NO: 2

```
tatagaaaaa tatattaatg aaagggtggt tttatgaaaa
aaaatcttgt aaaaagttta gcaatcgcat cagcggtgat
atccatctat tcaatagtta atattgtttc gccaactaat
gtaatagcta aggaaatatc taatacagta tctaatgaaa
tgtccaaaaa agcttcttat gataatgtag atacattaat
tgagaaagga agatataata caaaatataa ttacttaaag
agaatggaaa aatattatcc taatgctatg gcatattttg
ataaggttac tataaatcca caaggaaatg atttttatat
taataatcct aaagttgaat tagatggaga accatcaatg
aattatcttg aagatgttta tgttggaaaa gctctcttaa
ctaatgatac tcaacaagaa caaaaattaa aatcacaatc
attcacttgt aaaaatactg atacagtaac tgcaactact
actcatactg tgggaacttc gatacaagca actgctaagt
ttactgttcc ttttaatgaa acaggagtat cattaactac
tagttatagt tttgcaaata caaatacaaa tactaattca
aaagaaatta ctcataatgt cccttcacaa gatatactag
taccagctaa tactactgta gaagtaatag catatttaaa
aaaagttaat gttaaaggaa atgtaaagtt agtaggacaa
gtaagtggaa gtgaatgggg agagatacct agttatttag
cttttcctag ggatggttat aaatttagtt tatcagatac
agtaaataag agtgatttaa atgaagatgg tactattaat
attaatggaa aaggaaatta tagtgcagtt atgggagatg
agttaatagt taaggttaga aatttaaata caaataatgt
acaagaatat gtaatacctg tagataaaaa agaaaaaagt
aatgattcaa atatagtaaa atataggagt ctttctatta
aggcaccagg aataaaataa gattatttat tagaagtaaa
aataagattt tagttttata gattaatatt aattctaata
```

```
aaaactctat atagatttgt atgtaatcta attttcctc
```

Myelin and Lymphocyte Protein isoform a
[Homo sapiens, NP_002362.1, GI 4505091]
SEQ ID NO: 3
```
MAPAAATGGS TLPSGFSVFT TLPDLLFIFE FIFGGLVWIL
VASSLVPWPL VQGWVMFVSV FCFVATTTLI ILYIIGAHGG
ETSWVTLDAA YHCTAALFYL SASVLEALAT ITMQDGFTYR
HYHENIAAVV FSYIATLLYV VHAVFSLIRW KSS
```

Myelin and Lymphocyte Protein isoform b
[Homo sapiens, NP_071885.1, GI 12408665]
SEQ ID NO: 4
```
MAPAAATGGS TLPSGFSVFT TLPDLLFIFE FIFGGLVWIL
VASSLVPWPL VQGWVMFVSV FCFVATTTLI ILYIIGAHGG
ETSWVTLVFS YIATLLYVVH AVFSLIRWKS S
```

Myelin and Lymphocyte Protein isoform c
[Homo sapiens, NP_071884.1, GI 12408663]
SEQ ID NO: 5
```
MAPAAATGGS TLPSGFSVFT TLPDLLFIFE FDAAYHCTAA
LFYLSASVLE ALATITMQDG FTYRHYHENI AAVVFSYIAT
LLYVVHAVFS LIRWKSS
```

Myelin and Lymphocyte Protein isoform d
[Homo sapiens, NP_071885.1, GI 12408665]
SEQ ID NO: 6
```
MAPAAATGGS TLPSGFSVFT TLPDLLFIFE FVFSYIATLL
YVVHAVFSLI RWKSS
```

Amino Acid Sequence of HAvR-1 Protein
[Homo sapiens, NP_001092884.1]
SEQ ID NO: 7
```
MHPQVVILSL ILHLADSVAG SVKVGGEAGP SVTLPCHYSG
AVTSMCWNRG SCSLFTCQNG IVWTNGTHVT YRKDTRYKLL
GDLSRRDVSL TIENTAVSDS GVYCCRVEHR GWFNDMKITV
SLEIVPPKVT TTPIVTTVPT VTTVRTSTTV PTTTTVPMTT
VPTTTVPTTM SIPTTTTVLT TMTVSTTTSV PTTTSIPTTT
SVPVTTTVST FVPPMPLPRQ NHEPVATSPS SPQPAETHPT
TLQGAIRREP TSSPLYSYTT DGNDTVTESS DGLWNNNQTQ
LFLEHSLLTA NTTKGIYAGV CISVLVLLAL LGVIIAKKYF
FKKEVQQLSV SFSSLQIKAL QNAVEKEVQA EDNIYIENSL
YATD
```

16S rRNA (positive control) fwd primer
SEQ ID NO: 8
```
AGAGTTTGATCCTGGCTCA
```
reverse primer
SEQ ID NO: 9
```
GGTTACCTTGTTACGACTT
```

Alpha toxin (pan C. perfringens marker) fwd primer
SEQ ID NO: 10
```
GCTAATGTTACTGCCGTTGA
```
reverse primer
SEQ ID NO: 11
```
CCTCTGATACATCGTGTAAG
```

Beta toxin fwd primer
SEQ ID NO: 12
```
GCGAATATGCTGAATCATCTA
```
reverse primer
SEQ ID NO: 13
```
GCAGGAACATTAGTATATCTTC
```

Epsilon toxin fwd primer
SEQ ID NO: 14
```
GCGGTGATATCCATCTATTC
```
reverse primer
SEQ ID NO: 15
```
CCACTTACTTGTCCTACTAAC
```

B1RBB5 phage gene fwd primer
SEQ ID NO: 16
```
AAATGGACAAGAGGGATAAGGAT
```
reverse primer
SEQ ID NO: 17
```
TTTTCATCACAAATACCAGCCTC
```

B1RAA6 phage gene fwd primer
SEQ ID NO: 18
```
TTACAATAAAACCACATGAGCTT
```
reverse primer
SEQ ID NO: 19
```
TTTTATTTAACATACTCCGTTTT
```

Q8SBN7 phage gene fwd primer
SEQ ID NO: 20
```
GGGTGTCAAAGAAGATTTTAAAG
```
reverse primer
SEQ ID NO: 21
```
TTCTATCTTGCAACATTATATTT
```

The invention claimed is:

1. A method for treating epsilon toxin induced neurologic symptoms of multiple sclerosis (MS) in a subject in need comprising: administering to said subject a composition comprising an effective amount of an antibody that inhibits epsilon toxin (ETX) receptor from binding to Epsilon or ETX oligomerization, wherein the epsilon toxin (ETX)-produced by *Clostridium perfringens* type B or type D bacterial strain, so as to inhibit or suppress ETX modulated receptor signaling activities, and wherein said ETX-binding receptor is a tetraspan integral membrane receptor MAL or HAVcR-1 receptor, thereby treating neurologic symptoms of MS in said subject.

2. The method of claim 1, wherein said antibody is selected from the group consisting of a monoclonal antibody, a polyclonal antibody, and a recombinant antibody.

3. The method of claim 2, wherein said antibody is human or humanized antibody.

4. The method of claim 1, wherein said antibody is a neutralizing antibody against ETA or a functional component thereof.

5. The method of claim 1, wherein said ETX-binding receptor is expressed on endothelial cells of blood brain barrier (BBB) for which ETX is a ligand.

* * * * *

SEQUENCE LISTING

<160> NUMBER OF SEQ ID NOS: 21

<210> SEQ ID NO 1
<211> LENGTH: 328
<212> TYPE: PRT
<213> ORGANISM: Clostridium perfringens

<400> SEQUENCE: 1

Met Lys Lys Asn Leu Val Lys Ser Leu Ala Ile Ala Ser Ala Val Ile

```
  1               5                  10                  15
Ser Ile Tyr Ser Ile Val Asn Ile Val Ser Pro Thr Asn Val Ile Ala
             20                  25                  30

Lys Glu Ile Ser Asn Thr Val Ser Asn Glu Met Ser Lys Lys Ala Ser
             35                  40                  45

Tyr Asp Asn Val Asp Thr Leu Ile Glu Lys Gly Arg Tyr Asn Thr Lys
 50                  55                  60

Tyr Asn Tyr Leu Lys Arg Met Glu Lys Tyr Tyr Pro Asn Ala Met Ala
 65                  70                  75                  80

Tyr Phe Asp Lys Val Thr Ile Asn Pro Gln Gly Asn Asp Phe Tyr Ile
             85                  90                  95

Asn Asn Pro Lys Val Glu Leu Asp Gly Glu Pro Ser Met Asn Tyr Leu
             100                 105                 110

Glu Asp Val Tyr Val Gly Lys Ala Leu Leu Thr Asn Asp Thr Gln Gln
             115                 120                 125

Glu Gln Lys Leu Lys Ser Gln Ser Phe Thr Cys Lys Asn Thr Asp Thr
             130                 135                 140

Val Thr Ala Thr Thr Thr His Thr Val Gly Thr Ser Ile Gln Ala Thr
145                  150                 155                 160

Ala Lys Phe Thr Val Pro Phe Asn Glu Thr Gly Val Ser Leu Thr Thr
                 165                 170                 175

Ser Tyr Ser Phe Ala Asn Thr Asn Thr Asn Ser Lys Glu Ile
                 180                 185                 190

Thr His Asn Val Pro Ser Gln Asp Ile Leu Val Pro Ala Asn Thr Thr
             195                 200                 205

Val Glu Val Ile Ala Tyr Leu Lys Lys Val Asn Val Lys Gly Asn Val
 210                 215                 220

Lys Leu Val Gly Gln Val Ser Gly Ser Glu Trp Gly Glu Ile Pro Ser
225                  230                 235                 240

Tyr Leu Ala Phe Pro Arg Asp Gly Tyr Lys Phe Ser Leu Ser Asp Thr
                 245                 250                 255

Val Asn Lys Ser Asp Leu Asn Glu Asp Gly Thr Ile Asn Ile Asn Gly
             260                 265                 270

Lys Gly Asn Tyr Ser Ala Val Met Gly Asp Glu Leu Ile Val Lys Val
             275                 280                 285

Arg Asn Leu Asn Thr Asn Asn Val Gln Glu Tyr Val Ile Pro Val Asp
 290                 295                 300

Lys Lys Glu Lys Ser Asn Asp Ser Asn Ile Val Lys Tyr Arg Ser Leu
305                  310                 315                 320

Ser Ile Lys Ala Pro Gly Ile Lys
                 325

<210> SEQ ID NO 2
<211> LENGTH: 1119
<212> TYPE: DNA
<213> ORGANISM: Clostridium perfringens

<400> SEQUENCE: 2
tatagaaaaa tatattaatg aaagggtggt tttatgaaaa aaaatcttgt aaaaagttta    60
gcaatcgcat cagcggtgat atccatctat tcaatagtta atattgtttc gccaactaat   120
gtaatagcta aggaaatatc taatacagta tctaatgaaa tgtccaaaaa agcttcttat   180
gataatgtag atacattaat tgagaaagga agatataata caaatataa ttacttaaag    240 agaatggaaa aatattatcc taatgctatg gcatattttg ataaggttac tataaatcca   300
```

-continued

```
caaggaaatg attttatat taataatcct aaagttgaat tagatggaga accatcaatg    360
aattatcttg aagatgttta tgttggaaaa gctctcttaa ctaatgatac tcaacaagaa    420
caaaaattaa aatcacaatc attcacttgt aaaaatactg atacagtaac tgcaactact    480
actcatactg tgggaacttc gatacaagca actgctaagt ttactgttcc ttttaatgaa    540
acaggagtat cattaactac tagttatagt tttgcaaata caaatacaaa tactaattca    600
aaagaaatta ctcataatgt cccttcacaa gatatactag taccagctaa tactactgta    660
gaagtaatag catatttaaa aaaagttaat gttaaaggaa atgtaaagtt agtaggacaa    720
gtaagtggaa gtgaatgggg agagatacct agttatttag cttttcctag ggatggttat    780
aaatttagtt tatcagatac agtaaataag agtgatttaa atgaagatgg tactattaat    840
attaatggaa aaggaaatta tagtgcagtt atgggagatg agttaatagt taaggttaga    900
aatttaaata caaataatgt acaagaatat gtaatacctg tagataaaaa agaaaaagt    960 aatgattcaa atatagtaaa atataggagt ctttctatta aggcaccagg aataaaataa   1020
gattatttat tagaagtaaa aataagatt tagttttata gattaatatt aattctaata   1080
aaaactctat atagatttgt atgtaatcta attttcctc                           1119
```

<210> SEQ ID NO 3
<211> LENGTH: 153
<212> TYPE: PRT
<213> ORGANISM: Homo sapiens

<400> SEQUENCE: 3

```
Met Ala Pro Ala Ala Ala Thr Gly Gly Ser Thr Leu Pro Ser Gly Phe
1               5                   10                  15

Ser Val Phe Thr Thr Leu Pro Asp Leu Leu Phe Ile Phe Glu Phe Ile
                20                  25                  30

Phe Gly Gly Leu Val Trp Ile Leu Val Ala Ser Ser Leu Val Pro Trp
            35                  40                  45

Pro Leu Val Gln Gly Trp Val Met Phe Val Ser Val Phe Cys Phe Val
        50                  55                  60

Ala Thr Thr Thr Leu Ile Ile Leu Tyr Ile Ile Gly Ala His Gly Gly
65                  70                  75                  80

Glu Thr Ser Trp Val Thr Leu Asp Ala Ala Tyr His Cys Thr Ala Ala
                85                  90                  95

Leu Phe Tyr Leu Ser Ala Ser Val Leu Glu Ala Leu Ala Thr Ile Thr
            100                 105                 110

Met Gln Asp Gly Phe Thr Tyr Arg His Tyr His Glu Asn Ile Ala Ala
        115                 120                 125

Val Val Phe Ser Tyr Ile Ala Thr Leu Leu Tyr Val Val His Ala Val
    130                 135                 140

Phe Ser Leu Ile Arg Trp Lys Ser Ser
145                 150
```

<210> SEQ ID NO 4
<211> LENGTH: 111
<212> TYPE: PRT
<213> ORGANISM: Homo sapiens

<400> SEQUENCE: 4

```
Met Ala Pro Ala Ala Ala Thr Gly Gly Ser Thr Leu Pro Ser Gly Phe
1               5                   10                  15

Ser Val Phe Thr Thr Leu Pro Asp Leu Leu Phe Ile Phe Glu Phe Ile
```

```
                20                  25                  30

Phe Gly Gly Leu Val Trp Ile Leu Val Ala Ser Ser Leu Val Pro Trp
            35                  40                  45

Pro Leu Val Gln Gly Trp Val Met Phe Val Ser Val Phe Cys Phe Val
 50                  55                  60

Ala Thr Thr Thr Leu Ile Ile Leu Tyr Ile Ile Gly Ala His Gly Gly
 65                  70                  75                  80

Glu Thr Ser Trp Val Thr Leu Val Phe Ser Tyr Ile Ala Thr Leu Leu
                 85                  90                  95

Tyr Val Val His Ala Val Phe Ser Leu Ile Arg Trp Lys Ser Ser
                100                 105                 110

<210> SEQ ID NO 5
<211> LENGTH: 97
<212> TYPE: PRT
<213> ORGANISM: Homo sapiens

<400> SEQUENCE: 5

Met Ala Pro Ala Ala Ala Thr Gly Gly Ser Thr Leu Pro Ser Gly Phe
 1               5                  10                  15

Ser Val Phe Thr Thr Leu Pro Asp Leu Leu Phe Ile Phe Glu Phe Asp
                20                  25                  30

Ala Ala Tyr His Cys Thr Ala Ala Leu Phe Tyr Leu Ser Ala Ser Val
            35                  40                  45

Leu Glu Ala Leu Ala Thr Ile Thr Met Gln Asp Gly Phe Thr Tyr Arg
 50                  55                  60

His Tyr His Glu Asn Ile Ala Ala Val Val Phe Ser Tyr Ile Ala Thr
 65                  70                  75                  80

Leu Leu Tyr Val Val His Ala Val Phe Ser Leu Ile Arg Trp Lys Ser
                 85                  90                  95

Ser

<210> SEQ ID NO 6
<211> LENGTH: 55
<212> TYPE: PRT
<213> ORGANISM: Homo sapiens

<400> SEQUENCE: 6

Met Ala Pro Ala Ala Ala Thr Gly Gly Ser Thr Leu Pro Ser Gly Phe
 1               5                  10                  15

Ser Val Phe Thr Thr Leu Pro Asp Leu Leu Phe Ile Phe Glu Phe Val
                20                  25                  30

Phe Ser Tyr Ile Ala Thr Leu Leu Tyr Val Val His Ala Val Phe Ser
            35                  40                  45

Leu Ile Arg Trp Lys Ser Ser
 50                  55

<210> SEQ ID NO 7
<211> LENGTH: 364
<212> TYPE: PRT
<213> ORGANISM: Homo sapiens

<400> SEQUENCE: 7

Met His Pro Gln Val Val Ile Leu Ser Leu Ile Leu His Leu Ala Asp
 1               5                  10                  15

Ser Val Ala Gly Ser Val Lys Val Gly Gly Glu Ala Gly Pro Ser Val
                20                  25                  30
```

```
Thr Leu Pro Cys His Tyr Ser Gly Ala Val Thr Ser Met Cys Trp Asn
             35                  40                  45

Arg Gly Ser Cys Ser Leu Phe Thr Cys Gln Asn Gly Ile Val Trp Thr
 50                  55                  60

Asn Gly Thr His Val Thr Tyr Arg Lys Asp Thr Arg Tyr Lys Leu Leu
 65                  70                  75                  80

Gly Asp Leu Ser Arg Arg Asp Val Ser Leu Thr Ile Glu Asn Thr Ala
                 85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
            115                 120                 125

Val Thr Thr Thr Pro Ile Val Thr Thr Val Pro Thr Val Thr Thr Val
        130                 135                 140

Arg Thr Ser Thr Thr Val Pro Thr Thr Thr Val Pro Met Thr Thr
145                 150                 155                 160

Val Pro Thr Thr Thr Val Pro Thr Thr Met Ser Ile Pro Thr Thr Thr
                165                 170                 175

Thr Val Leu Thr Thr Met Thr Val Ser Thr Thr Thr Ser Val Pro Thr
            180                 185                 190

Thr Thr Ser Ile Pro Thr Thr Thr Ser Val Pro Val Thr Thr Thr Val
        195                 200                 205

Ser Thr Phe Val Pro Pro Met Pro Leu Pro Arg Gln Asn His Glu Pro
    210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asn Asp Thr Val Thr Glu Ser Ser Asp Gly
            260                 265                 270

Leu Trp Asn Asn Asn Gln Thr Gln Leu Phe Leu Glu His Ser Leu Leu
            275                 280                 285

Thr Ala Asn Thr Thr Lys Gly Ile Tyr Ala Gly Val Cys Ile Ser Val
290                 295                 300

Leu Val Leu Leu Ala Leu Leu Gly Val Ile Ile Ala Lys Lys Tyr Phe
305                 310                 315                 320

Phe Lys Lys Glu Val Gln Gln Leu Ser Val Ser Phe Ser Ser Leu Gln
                325                 330                 335

Ile Lys Ala Leu Gln Asn Ala Val Glu Lys Glu Val Gln Ala Glu Asp
            340                 345                 350

Asn Ile Tyr Ile Glu Asn Ser Leu Tyr Ala Thr Asp
            355                 360

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agagtttgat cctggctca                                              19

<210> SEQ ID NO 9
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggttaccttg ttacgactt                                                  19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctaatgtta ctgccgttga                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctctgatac atcgtgtaag                                                 20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgaatatgc tgaatcatct a                                               21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcaggaacat tagtatatct tc                                              22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcggtgatat ccatctattc                                                 20

<210> SEQ ID NO 15
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 15
ccacttactt gtcctactaa c                                               21

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaatggacaa gagggataag gat                                             23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttttcatcac aaataccagc ctc                                             23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttacaataaa accacatgag ctt                                             23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttttatttaa catactccgt ttt                                             23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gggtgtcaaa gaagatttta aag                                             23

<210> SEQ ID NO 21
<211> LENGTH: 23
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 21
ttctatcttg caacattata ttt                                            23
```